(12) United States Patent
Foletti et al.

(10) Patent No.: US 8,715,673 B2
(45) Date of Patent: May 6, 2014

(54) STAPHYLOCOCCUS AUREUS SPECIFIC ANTIBODIES AND USES THEREOF

(71) Applicant: Rinat Neuroscience Corp., South San Francisco, CA (US)

(72) Inventors: Davide Luciano Foletti, Menlo Park, CA (US); Javier Fernando Chaparro Riggers, San Mateo, CA (US); Jacob Eli Gunn Glanville, San Francisco, CA (US); Lee Mary Beth Shaughnessy, Madison, WI (US); David Louis Shelton, Oakland, CA (US); Pavel Strop, San Mateo, CA (US); Wenwu Zhai, Redwood City, CA (US)

(73) Assignee: Rinat Neuroscience Corp., South San Francisco, CA (US)

( * ) Notice: Subject to any disclaimer, the term of this patent is extended or adjusted under 35 U.S.C. 154(b) by 0 days.

(21) Appl. No.: 13/719,214

(22) Filed: Dec. 18, 2012

(65) Prior Publication Data
US 2013/0164308 A1     Jun. 27, 2013

Related U.S. Application Data

(60) Provisional application No. 61/579,548, filed on Dec. 22, 2011, provisional application No. 61/692,626, filed on Aug. 23, 2012.

(51) Int. Cl.
*A61K 39/40* (2006.01)

(52) U.S. Cl.
USPC ...................................................... 424/165.1

(58) Field of Classification Search
None
See application file for complete search history.

(56) References Cited

U.S. PATENT DOCUMENTS

2011/0027265 A1   2/2011   Bubeck-Wardenburg et al.

FOREIGN PATENT DOCUMENTS

EP     2284193 A1     2/2011

OTHER PUBLICATIONS

Vajdos et al. (J Mol Biol. Jul. 5, 2002;320(2):415-28.*
Brown et al. (J Immunol. May 1996;156(9):3285-91.*
Heveker, N., et al., "Characterization of Neutralizing Monoclonal Antibodies Directed Against *Staphylococcus aureus* Alpha-Toxin," Hybridoma, 1994, 263-270, vol. 13, No. 4.
Blomqvist, L., et al., "Production and Characterization of Monoclonal Antibodies Against *Staphylococcus aureus* a-Toxin," Toxicon, 1988, 265-273, vol. 26, No. 3.
Ragle, B., et al., "Anti-Alpha-Hemolysin Monoclonal Antibodies Mediate Protection against *Staphylococcus aureus* Pneumonia," Infection and Immunity, 2009, 2712-2718, vol. 77, No. 7.
Heveker, N., et al., "Neutralizaing Monoclonal Antibodies against *Staphylococcus aureus* alpha toxin: A Structure-Function Study," Medical Microbiology and Immunology, 1993, 191, vol. 182, No. 4.
Heveker, N., et al., "A Human Monoclonal Antibody with the Capacity ot Neutralize *Staphylococcus aureus* Alpha-Toxin," Human Antibodies and Hybridomas, 1994, 18-24, vol. 5, No. 1-2.
The International Search Report for International Application No. PCT/IB2012/057085 dated Apr. 10, 2013.
The Written Opinion for International Application No. PCT/IB2012/057085 dated Apr. 10, 2013.
Bubeck Wardenburg, J., et al., "Vaccine Protection Against *Staphylococcus Aureus* Pneumonia," J Exp Med., 2008, 287-294, vol. 205, No. 2.

* cited by examiner

*Primary Examiner* — Brian J Gangle
(74) *Attorney, Agent, or Firm* — Susan L. Wang

(57) ABSTRACT

The present invention provides antagonizing antibodies that bind to *S. aureus* alpha-toxin. The invention further provides a method of obtaining such antibodies and antibody encoding nucleic acids. The invention further relates to therapeutic methods for use of these antibodies for the treatment and/or prevention of staphylococcal disease, including, for example, pneumonia, bacteremia, sepsis, eye infection, and abscess.

15 Claims, 10 Drawing Sheets

Table A: Amino Acid frequency (%) for each position in VH CDR3 of Alpha-toxin Antibodies

| | | Position According to Kabat Numbering | | | | | | | | | | | | | | | |
|---|---|---|---|---|---|---|---|---|---|---|---|---|---|---|---|---|---|
| | | 95 | 96 | 97 | 98 | 99 | 100 | 100A | 100B | 100C | 100D | 100E | 100F | 100G | 100H | 101 | 102 |
| CDR pos | | 1 | 2 | 3 | 4 | 5 | 6 | 7 | 8 | 9 | 10 | 11 | 12 | 13 | 14 | 15 | 16 |
| DF1 | | E | M | E | V | S | G | R | W | R | P | T | E | A | F | E | I |
| amino acid (1-letter code) | A | 0 | 0 | 0 | 8.1 | 2.7 | 0 | 0 | 0 | 0 | 0 | 2.7 | 0 | 86.4 | 0 | 0 | 0 |
| | C | 0 | 0 | 0 | 0 | 0 | 0 | 0 | 2.7 | 0 | 0 | 0 | 0 | 0 | 0 | 0 | 0 |
| | D | 5.4 | 0 | 0 | 0 | 0 | 0 | 5.4 | 2.7 | 0 | 0 | 0 | 21.6 | 0 | 0 | 16.2 | 0 |
| | E | 89.1 | 0 | 89.1 | 5.4 | 0 | 0 | 0 | 0 | 0 | 0 | 0 | 48.6 | 0 | 0 | 78.3 | 0 |
| | F | 0 | 0 | 0 | 0 | 0 | 0 | 0 | 0 | 0 | 0 | 0 | 0 | 0 | 97.2 | 0 | 5.4 |
| | G | 5.4 | 0 | 5.4 | 16.2 | 0 | 86.4 | 8.1 | 2.7 | 5.4 | 10.8 | 0 | 10.8 | 0 | 0 | 0 | 0 |
| | H | 0 | 2.7 | 0 | 0 | 0 | 0 | 0 | 0 | 0 | 0 | 5.4 | 5.4 | 0 | 0 | 0 | 0 |
| | I | 0 | 0 | 0 | 0 | 2.7 | 0 | 0 | 0 | 0 | 0 | 0 | 0 | 0 | 0 | 0 | 78.3 |
| | K | 0 | 0 | 0 | 0 | 0 | 0 | 0 | 0 | 0 | 0 | 0 | 5.4 | 0 | 0 | 0 | 0 |
| | L | 0 | 16.2 | 2.7 | 0 | 0 | 0 | 0 | 0 | 0 | 2.7 | 0 | 0 | 5.4 | 2.7 | 0 | 2.7 |
| | M | 0 | 43.2 | 0 | 0 | 0 | 0 | 0 | 0 | 0 | 0 | 0 | 0 | 0 | 0 | 0 | 0 |
| | N | 0 | 0 | 0 | 0 | 5.4 | 0 | 0 | 2.7 | 0 | 0 | 0 | 5.4 | 0 | 0 | 0 | 0 |
| | P | 0 | 0 | 0 | 0 | 0 | 0 | 0 | 0 | 0 | 81 | 5.4 | 0 | 5.4 | 0 | 0 | 0 |
| | Q | 0 | 0 | 0 | 0 | 0 | 0 | 43.2 | 0 | 2.7 | 0 | 5.4 | 0 | 0 | 0 | 0 | 0 |
| | R | 0 | 5.4 | 0 | 0 | 2.7 | 2.7 | 43.2 | 2.7 | 81 | 5.4 | 0 | 0 | 0 | 0 | 0 | 0 |
| | S | 0 | 0 | 0 | 0 | 51.3 | 5.4 | 0 | 5.4 | 5.4 | 0 | 0 | 2.7 | 0 | 0 | 5.4 | 0 |
| | T | 0 | 0 | 0 | 0 | 29.7 | 0 | 0 | 0 | 0 | 0 | 81 | 0 | 0 | 0 | 0 | 0 |
| | V | 0 | 29.7 | 0 | 64.8 | 0 | 0 | 0 | 0 | 0 | 0 | 0 | 0 | 2.7 | 0 | 0 | 13.5 |
| | W | 0 | 0 | 0 | 0 | 0 | 0 | 0 | 81 | 0 | 0 | 0 | 0 | 0 | 0 | 0 | 0 |
| | Y | 0 | 2.7 | 2.7 | 5.4 | 5.4 | 5.4 | 0 | 0 | 5.4 | 0 | 0 | 0 | 0 | 0 | 0 | 0 |

FIG. 1

Table B: Amino Acid frequency (%) for each position in VL CDR3 of Alpha-toxin Antibodies

| | | Position According to Kabat Numbering | | | | | | | |
|---|---|---|---|---|---|---|---|---|---|
| | | 90 | 91 | 92 | 93 | 94 | 95 | 96 | 97 |
| CDR pos | | 1 | 2 | 3 | 4 | 5 | 6 | 7 | 8 |
| Ref | | Q | Q | Y | G | S | S | P | T |
| amino acid (1-letter code) | A | 0 | 0 | 3.9 | 3.9 | 1.3 | 2.6 | 0 | 2.6 |
| | C | 0 | 0 | 0 | 0 | 0 | 0 | 0 | 0 |
| | D | 0 | 0 | 0 | 6.5 | 6.5 | 1.3 | 1.3 | 1.3 |
| | E | 0 | 1.3 | 0 | 1.3 | 0 | 2.6 | 0 | 0 |
| | F | 0 | 0 | 2.6 | 0 | 1.3 | 0 | 2.6 | 0 |
| | G | 0 | 0 | 1.3 | 55.2 | 6.5 | 0 | 2.6 | 1.3 |
| | H | 3.9 | 6.5 | 0 | 1.3 | 0 | 1.3 | 1.3 | 0 |
| | I | 0 | 0 | 0 | 0 | 2.6 | 0 | 3.9 | 0 |
| | K | 0 | 2.6 | 0 | 0 | 0 | 0 | 0 | 1.3 |
| | L | 1.3 | 1.3 | 0 | 3.9 | 0 | 6.5 | 14.4 | 2.6 |
| | M | 3.9 | 0 | 0 | 0 | 0 | 0 | 0 | 0 |
| | N | 0 | 0 | 0 | 5.2 | 7.8 | 0 | 0 | 0 |
| | P | 0 | 0 | 0 | 0 | 0 | 3.9 | 39.4 | 1.3 |
| | Q | 90.7 | 86.8 | 0 | 0 | 2.6 | 0 | 2.6 | 1.3 |
| | R | 0 | 1.3 | 3.9 | 0 | 11.8 | 0 | 6.5 | 0 |
| | S | 0 | 0 | 3.9 | 9.2 | 40.7 | 59.2 | 7.8 | 10.5 |
| | T | 0 | 0 | 1.3 | 1.3 | 17.1 | 11.8 | 0 | 75 |
| | V | 0 | 0 | 0 | 0 | 0 | 0 | 6.5 | 2.6 |
| | W | 0 | 0 | 0 | 0 | 0 | 6.5 | 7.8 | 0 |
| | Y | 0 | 0 | 82 | 11 | 1.3 | 3.9 | 2.6 | 0 |

FIG. 2

Table C: Amino Acid frequency (%) for each position in VL CDR3 of Alpha-toxin Antibodies

| | | Position According to Kabat Numbering | | | | | | | | |
|---|---|---|---|---|---|---|---|---|---|---|
| | | 90 | 91 | 92 | 93 | 94 | 95 | 95A | 96 | 97 |
| CDR pos | | 1 | 2 | 3 | 4 | 5 | 6 | 7 | 8 | 9 |
| Ref | | Q | Q | Y | G | S | S | P | L | T |
| amino acid (1-letter code) | A | 0 | 0 | 5.5 | 5.8 | 3 | 4.4 | 0.9 | 0.2 | 0.6 |
| | C | 0 | 0 | 0.2 | 0 | 0 | 0 | 0 | 0 | 0 |
| | D | 0 | 0 | 0.6 | 8.8 | 4.4 | 0.2 | 0.2 | 0 | 0 |
| | E | 0.2 | 0.2 | 0 | 0.2 | 1.1 | 0 | 0.4 | 0.9 | 0 |
| | F | 0 | 0 | 3 | 0.9 | 0.2 | 6.9 | 0.2 | 7.2 | 0 |
| | G | 0 | 0 | 0.4 | 36.5 | 6.5 | 0.4 | 0.4 | 1.1 | 0.2 |
| | H | 7.2 | 5.1 | 3.2 | 3.9 | 1.3 | 0 | 0.4 | 0.4 | 0 |
| | I | 0 | 0 | 0 | 1.3 | 2 | 1.3 | 0.2 | 8.8 | 0.4 |
| | K | 0 | 2 | 0 | 0.6 | 1.8 | 0.2 | 0 | 1.3 | 0.2 |
| | L | 2.3 | 0 | 2.7 | 5.1 | 0.4 | 4.1 | 4.4 | 28.1 | 0.2 |
| | M | 5.3 | 0 | 0 | 0.2 | 0.2 | 1.1 | 0.6 | 0.2 | 0 |
| | N | 0 | 0.4 | 0 | 11.8 | 11.1 | 0.4 | 0.2 | 1.3 | 0.6 |
| | P | 0 | 0 | 0.2 | 0 | 0 | 3 | 83.2 | 7.2 | 0.4 |
| | Q | 84.8 | 91.3 | 0 | 0 | 4.1 | 0.2 | 0.4 | 1.8 | 0 |
| | R | 0 | 0.2 | 3.2 | 1.1 | 3.2 | 0 | 0.9 | 10.9 | 0 |
| | S | 0 | 0.4 | 10.2 | 8.1 | 45.1 | 48.1 | 5.1 | 0.9 | 1.8 |
| | T | 0 | 0 | 2.3 | 1.1 | 13.2 | 12.5 | 0.9 | 0.6 | 94.4 |
| | V | 0 | 0 | 0.2 | 1.3 | 0.2 | 1.3 | 0.9 | 4.1 | 0.6 |
| | W | 0 | 0 | 0 | 0 | 0.2 | 6.9 | 0 | 8.8 | 0 |
| | Y | 0 | 0 | 67 | 12 | 1.1 | 8.1 | 0 | 15 | 0 |

FIG. 3

Table D: Amino Acid frequency (%) for each position in VL CDR3 of Alpha-toxin Antibodies

| | | Position According to Kabat Numbering | | | | | | | | | |
|---|---|---|---|---|---|---|---|---|---|---|---|
| | | 90 | 91 | 92 | 93 | 94 | 95 | 95A | 95B | 96 | 97 |
| CDR pos | | 1 | 2 | 3 | 4 | 5 | 6 | 7 | 8 | 9 | 10 |
| Ref | | Q | Q | Y | G | S | S | P | P | Y | T |
| amino acid (1-letter code) | A | 0 | 0 | 0 | 3 | 4.5 | 3 | 1.5 | 0 | 0 | 1.5 |
| | C | 0 | 0 | 0 | 0 | 0 | 0 | 0 | 0 | 0 | 0 |
| | D | 0 | 0 | 0 | 4.5 | 1.5 | 0 | 0 | 0 | 1.5 | 0 |
| | E | 0 | 0 | 0 | 0 | 1.5 | 0 | 0 | 1.5 | 0 | 0 |
| | F | 0 | 0 | 0 | 0 | 0 | 0 | 0 | 0 | 7.5 | 0 |
| | G | 0 | 0 | 0 | 72.7 | 12.1 | 0 | 0 | 4.5 | 1.5 | 0 |
| | H | 7.5 | 6 | 0 | 3 | 0 | 0 | 0 | 0 | 0 | 0 |
| | I | 0 | 0 | 0 | 0 | 0 | 0 | 4.5 | 0 | 16.6 | 4.5 |
| | K | 0 | 0 | 0 | 1.5 | 0 | 0 | 0 | 0 | 0 | 0 |
| | L | 0 | 0 | 0 | 0 | 0 | 0 | 6 | 10.6 | 16.6 | 0 |
| | M | 0 | 0 | 0 | 0 | 0 | 0 | 0 | 0 | 0 | 1.5 |
| | N | 0 | 0 | 0 | 6 | 15.1 | 0 | 0 | 0 | 3 | 0 |
| | P | 0 | 0 | 0 | 0 | 0 | 0 | 78.7 | 62.1 | 0 | 1.5 |
| | Q | 89.3 | 89.3 | 0 | 0 | 0 | 0 | 1.5 | 1.5 | 0 | 0 |
| | R | 0 | 0 | 6 | 0 | 3 | 1.5 | 0 | 10.6 | 1.5 | 0 |
| | S | 3 | 3 | 1.5 | 6 | 40.9 | 80.3 | 4.5 | 3 | 0 | 6 |
| | T | 0 | 0 | 0 | 3 | 16.6 | 1.5 | 1.5 | 6 | 1.5 | 81.8 |
| | V | 0 | 0 | 0 | 0 | 0 | 0 | 1.5 | 0 | 9 | 3 |
| | W | 0 | 0 | 0 | 0 | 0 | 13.6 | 0 | 0 | 7.5 | 0 |
| | Y | 0 | 1.5 | 92 | 0 | 4.5 | 0 | 0 | 0 | 33 | 0 |

FIG. 4

Table E: Amino Acid frequency (%) for each position in VL CDR3 of Alpha-toxin Antibodies

| | | Position According to Kabat Numbering | | | | | | | | | | |
|---|---|---|---|---|---|---|---|---|---|---|---|---|
| | | 90 | 91 | 92 | 93 | 94 | 95 | 95A | 95B | 95C | 96 | 97 |
| CDR pos | | 1 | 2 | 3 | 4 | 5 | 6 | 7 | 8 | 9 | 10 | 11 |
| Ref | | Q | Q | Y | G | S | S | P | P | G | V | T |
| amino acid (1-letter code) | A | 0 | 0 | 0 | 0 | 0 | 0 | 0 | 0 | 16.6 | 0 | 8.3 |
| | C | 0 | 0 | 0 | 0 | 0 | 0 | 0 | 0 | 0 | 0 | 0 |
| | D | 0 | 0 | 0 | 33.3 | 0 | 0 | 0 | 8.3 | 8.3 | 0 | 0 |
| | E | 0 | 0 | 0 | 0 | 0 | 0 | 0 | 0 | 0 | 0 | 0 |
| | F | 0 | 0 | 0 | 0 | 0 | 0 | 0 | 0 | 0 | 8.3 | 0 |
| | G | 8.3 | 0 | 0 | 50 | 16.6 | 0 | 8.3 | 0 | 33.3 | 0 | 0 |
| | H | 0 | 0 | 0 | 0 | 0 | 0 | 0 | 0 | 8.3 | 0 | 0 |
| | I | 0 | 0 | 0 | 0 | 0 | 0 | 0 | 0 | 0 | 8.3 | 0 |
| | K | 0 | 0 | 0 | 0 | 0 | 0 | 0 | 0 | 0 | 0 | 0 |
| | L | 0 | 0 | 0 | 0 | 0 | 0 | 25 | 8.3 | 8.3 | 25 | 0 |
| | M | 0 | 0 | 0 | 0 | 0 | 0 | 0 | 0 | 8.3 | 0 | 0 |
| | N | 0 | 0 | 0 | 0 | 8.3 | 0 | 0 | 0 | 0 | 0 | 0 |
| | P | 0 | 0 | 0 | 0 | 0 | 0 | 41.6 | 25 | 0 | 0 | 0 |
| | Q | 83.3 | 58.3 | 0 | 0 | 0 | 0 | 0 | 0 | 0 | 0 | 0 |
| | R | 0 | 0 | 8.3 | 0 | 0 | 0 | 0 | 25 | 8.3 | 0 | 0 |
| | S | 8.3 | 25 | 0 | 8.3 | 50 | 91.6 | 16.6 | 25 | 8.3 | 0 | 0 |
| | T | 0 | 8.3 | 0 | 8.3 | 25 | 0 | 8.3 | 8.3 | 0 | 0 | 50 |
| | V | 0 | 8.3 | 0 | 0 | 0 | 0 | 0 | 0 | 0 | 33.3 | 41.6 |
| | W | 0 | 0 | 16.6 | 0 | 0 | 8.3 | 0 | 0 | 0 | 0 | 0 |
| | Y | 0 | 0 | 75 | 0 | 0 | 0 | 0 | 0 | 0 | 25 | 0 |

FIG. 5

| S. aureus Strain | \multicolumn{20}{c|}{amino acid position indicating variability in mature alpha toxin sequence} |

| S. aureus Strain | 9 | 14 | 19 | 38 | 52 | 54 | 79 | 87 | 129 | 175 | 194 | 197 | 208 | 218 | 239 | 243 | 246 | 275 | 278 | 288 |
|---|---|---|---|---|---|---|---|---|---|---|---|---|---|---|---|---|---|---|---|---|
| USA300 - consensus sequence | T | I | T | V | L | V | A | Q | T | V | Q | M | D | S | S | T | D | I | S | K |
| PFESA0207 | T | I | I | V | I | V | A | Q | S | V | Q | M | D | S | T | T | D | T | S | K |
| PFESA0150 | T | I | I | V | I | V | A | Q | S | V | Q | M | D | S | T | S | D | T | S | K |
| PFESA0249 | T | I | T | V | I | V | A | Q | S | V | Q | M | D | S | T | T | D | T | S | K |
| PFESA0184 | T | I | T | V | I | V | A | Q | S | V | Q | M | D | S | T | T | D | T | C | K |
| PFESA0124 | T | I | T | V | I | V | A | stop | S | V | Q | M | E | S | T | T | D | T | S | K |
| PFESA0163 | T | I | T | V | I | V | A | Q | S | V | Q | M | E | S | T | T | N | T | S | K |
| PFESA0174 | T | I | T | V | I | V | A | Q | S | V | Q | M | E | S | T | T | D | T | S | K |
| PFESA0141 | P | I | T | V | I | V | A | Q | T | M | Q | M | E | S | S | T | D | T | S | K |
| PFESA0204 | P | I | T | I | I | F | A | Q | T | M | Q | M | E | S | S | T | D | I | S | K |
| PFESA0009 | T | I | T | V | I | V | A | Q | T | V | Q | M | E | S | S | T | D | T | S | K |
| PFESA0140 | T | I | T | V | I | V | A | Q | T | V | Q | M | E | S | S | T | D | T | S | K |
| PFESA0102 | T | I | T | V | I | V | A | Q | T | V | K | M | E | F | S | T | D | T | S | N |
| PFESA0125 | T | I | T | V | I | V | A | Q | T | V | Q | M | E | S | S | T | D | T | S | K |
| PFESA0181 | T | I | T | V | I | V | A | Q | T | V | Q | M | D | S | S | T | D | T | S | K |
| PFESA0146 | T | F | T | V | I | V | A | Q | T | V | Q | M | D | S | S | T | D | T | S | K |
| PFESA0067 | T | I | T | V | I | V | A | Q | T | V | Q | M | D | S | S | T | D | I | S | K |
| PFESA0218 | T | I | T | V | I | V | T | Q | T | V | Q | M | D | S | S | T | D | I | S | K |

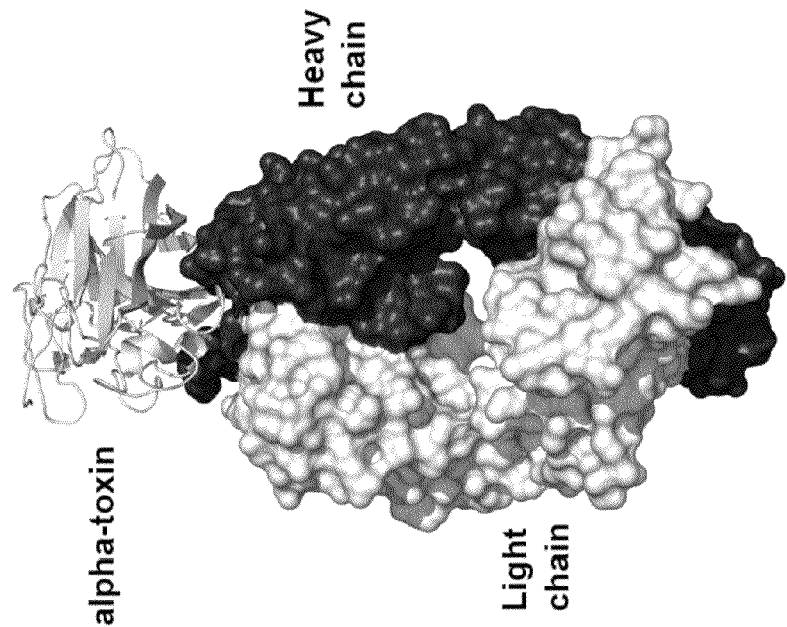
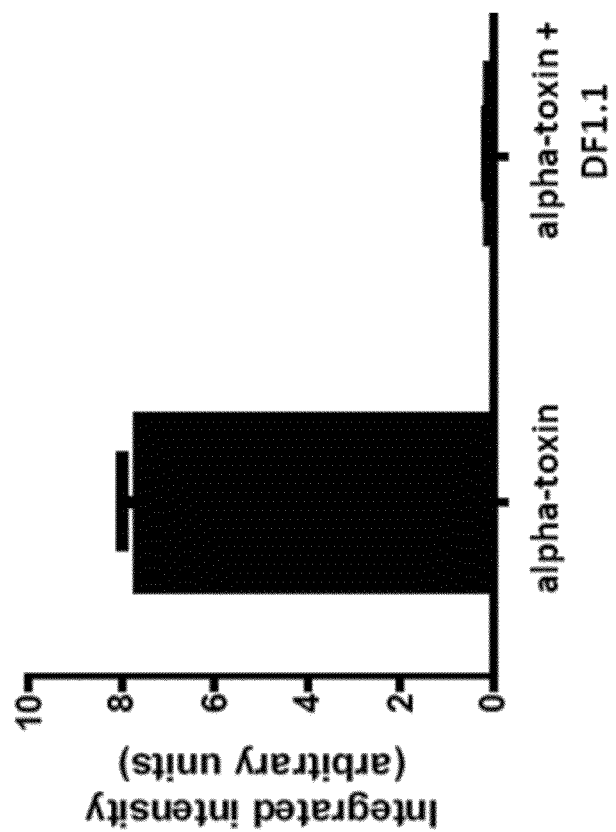
FIG. 8A
FIG. 8B

SEQUENCE LISTING

<160> NUMBER OF SEQ ID NOS: 74

<210> SEQ ID NO 1
<211> LENGTH: 108
<212> TYPE: PRT
<213> ORGANISM: Homo sapiens

<400> SEQUENCE: 1

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Ser Asn Asn
            20                  25                  30

Phe Val Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Val Asp Ile Lys
            100                 105

<210> SEQ ID NO 2
<211> LENGTH: 125
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Lys Ser Thr Thr Ser Thr Tyr
65                  70                  75                  80

Leu Glu Leu Ser Ser Leu Arg Ser Asp Asp Thr Ala Val Tyr Tyr Cys
                85                  90                  95

Ala Arg Glu Met Glu Val Ser Gly Arg Trp Arg Pro Thr Glu Ala Phe
            100                 105                 110

Glu Ile Trp Gly Gln Gly Thr Met Val Thr Val Ser Ser
        115                 120                 125

<210> SEQ ID NO 3
<211> LENGTH: 108
<212> TYPE: PRT
<213> ORGANISM: Homo sapiens

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Ser Asn Asn
            20                  25                  30

Phe Val Ala Trp Tyr Gln Gln Lys Pro Gly Gln Ala Pro Arg Leu Leu

```
            35                  40                  45
Ile Tyr Gly Ala Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Tyr Thr Phe Gly Gln Gly Thr Lys Leu Glu Ile Lys
            100                 105
```

<210> SEQ ID NO 4
<211> LENGTH: 125
<212> TYPE: PRT
<213> ORGANISM: Homo sapiens

<400> SEQUENCE: 4

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Asn Asn Val
                20                  25                  30

Ala Ile Asn Trp Val Arg Gln Ala Pro Gly Gln Gly Leu Glu Trp Met
            35                  40                  45

Gly Gly Ile Ile Pro Gly Leu Asp Thr Pro Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Met Glu Val Ser Gly Arg Trp Arg Pro Thr Glu Ala Phe
            100                 105                 110

Glu Ile Trp Gly Gln Gly Thr Leu Val Thr Val Ser Ser
            115                 120                 125
```

<210> SEQ ID NO 5
<211> LENGTH: 10
<212> TYPE: PRT
<213> ORGANISM: Homo sapiens

<400> SEQUENCE: 5

```
Gly Gly Thr Phe Asn Asn Val Ala Ile Asn
 1               5                  10
```

<210> SEQ ID NO 6
<211> LENGTH: 10
<212> TYPE: PRT
<213> ORGANISM: Homo sapiens

<400> SEQUENCE: 6

```
Gly Gly Thr Phe Asn Asn Val Ala Ile Asn
 1               5                  10
```

<210> SEQ ID NO 7
<211> LENGTH: 5
<212> TYPE: PRT
<213> ORGANISM: Homo sapiens

<400> SEQUENCE: 7

```
Asn Val Ala Ile Asn
 1               5
```

```
<210> SEQ ID NO 8
<211> LENGTH: 6
<212> TYPE: PRT
<213> ORGANISM: Homo sapiens

<400> SEQUENCE: 8

Ile Pro Gly Leu Asp Thr
1               5

<210> SEQ ID NO 9
<211> LENGTH: 17
<212> TYPE: PRT
<213> ORGANISM: Homo sapiens

<400> SEQUENCE: 9

Gly Ile Ile Pro Gly Leu Asp Thr Pro Asn Tyr Ala Gln Lys Phe Gln
1               5                   10                  15

Gly

<210> SEQ ID NO 10
<211> LENGTH: 16
<212> TYPE: PRT
<213> ORGANISM: Homo sapiens

<400> SEQUENCE: 10

Glu Met Glu Val Ser Gly Arg Trp Arg Pro Thr Glu Ala Phe Glu Ile
1               5                   10                  15

<210> SEQ ID NO 11
<211> LENGTH: 16
<212> TYPE: PRT
<213> ORGANISM: Homo sapiens

<400> SEQUENCE: 11

Glu Trp Glu Val Ser Gly Arg Trp Arg Pro Thr Glu Ala Phe Glu Ile
1               5                   10                  15

<210> SEQ ID NO 12
<211> LENGTH: 16
<212> TYPE: PRT
<213> ORGANISM: Homo sapiens

<400> SEQUENCE: 12

Glu Thr Glu Val Ser Gly Arg Trp Arg Pro Thr Glu Ala Phe Glu Ile
1               5                   10                  15

<210> SEQ ID NO 13
<211> LENGTH: 375
<212> TYPE: DNA
<213> ORGANISM: Homo sapiens

<400> SEQUENCE: 13
caggtgcagc tggttcagag tggcgccgag gttaagaagc cgggatcgtc cgtgaaggtg      60
tcctgtaagg catcaggcgg gactttcaac aatgtggcaa ttaattgggt tagacaggcc     120
ccagggcagg ggctggaatg gatgggcggc attattcccg gacttgatac cccaaattac     180
gcccagaagt ttcagggccg cgtgaccata accgccgacg aatctactag cactgcatac     240
atggagctta gcagtctgcg gagcgaggac accgccgtgt attactgcgc cagggagatg     300
gaggtgagcg gcaggtggag gcctaccgaa gccttcgaaa tctggggcca ggcaccctg      360 gtcaccgtct cttca                                                      375

<210> SEQ ID NO 14
```

```
<211> LENGTH: 324
<212> TYPE: PRT
<213> ORGANISM: Homo sapiens

<400> SEQUENCE: 14

Gly Ala Ala Ala Thr Ala Gly Thr Gly Cys Thr Ala Ala Cys Ala Cys
1               5                   10                  15

Ala Ala Thr Cys Cys Cys Thr Gly Gly Cys Ala Cys Cys Cys Cys Thr
            20                  25                  30

Gly Ala Gly Cys Cys Thr Gly Ala Gly Thr Cys Cys Cys Gly Gly Cys
        35                  40                  45

Gly Ala Ala Cys Gly Gly Gly Cys Thr Ala Cys Thr Cys Thr Gly Ala
50                  55                  60

Gly Cys Thr Gly Cys Ala Gly Ala Gly Cys Ala Ala Gly Thr Cys Ala
65                  70                  75                  80

Gly Ala Cys Ala Ala Thr Ala Ala Gly Cys Ala Ala Cys Ala Ala Cys
                85                  90                  95

Thr Thr Thr Gly Thr Cys Gly Cys Gly Thr Gly Gly Thr Ala Cys Cys
                100                 105                 110

Ala Gly Cys Ala Gly Ala Ala Gly Cys Cys Thr Gly Gly Cys Cys Ala
            115                 120                 125

Gly Gly Cys Ala Cys Cys Cys Gly Gly Cys Thr Gly Cys Thr Cys Cys
        130                 135                 140

Ala Thr Cys Thr Ala Thr Gly Gly Ala Gly Cys Cys Thr Cys Cys Ala
145                 150                 155                 160

Cys Cys Cys Gly Gly Cys Cys Ala Cys Thr Gly Gly Cys Ala Thr Cys
                165                 170                 175

Ala Cys Cys Ala Gly Ala Cys Ala Gly Ala Thr Thr Cys Thr Cys Thr
            180                 185                 190

Gly Gly Ala Ala Gly Cys Gly Gly Ala Gly Thr Gly Gly Cys Thr Ala
        195                 200                 205

Cys Gly Gly Ala Cys Thr Thr Cys Ala Cys Cys Cys Thr Gly Ala Cys
    210                 215                 220

Gly Ala Thr Cys Ala Gly Thr Ala Gly Gly Cys Thr Cys Gly Ala Gly
225                 230                 235                 240

Cys Cys Cys Gly Ala Ala Gly Ala Thr Thr Thr Thr Gly Cys Ala Gly
                245                 250                 255

Thr Gly Thr Ala Cys Thr Ala Cys Thr Gly Cys Cys Ala Ala Cys Ala
            260                 265                 270

Gly Thr Ala Thr Gly Gly Cys Ala Gly Thr Ala Gly Cys Cys Cys Cys
        275                 280                 285

Thr Ala Cys Ala Cys Ala Thr Thr Cys Gly Gly Thr Cys Ala Gly Gly
    290                 295                 300

Gly Gly Ala Cys Cys Ala Ala Gly Cys Thr Thr Gly Ala Gly Ala Thr
305                 310                 315                 320

Thr Ala Ala Ala

<210> SEQ ID NO 15
<211> LENGTH: 12
<212> TYPE: PRT
<213> ORGANISM: Homo sapiens

<400> SEQUENCE: 15

Arg Ala Ser Gln Thr Ile Ser Asn Asn Phe Val Ala
1               5                   10
```

<210> SEQ ID NO 16
<211> LENGTH: 7
<212> TYPE: PRT
<213> ORGANISM: Homo sapiens

<400> SEQUENCE: 16

Gly Ala Ser Thr Arg Ala Thr
1               5

<210> SEQ ID NO 17
<211> LENGTH: 9
<212> TYPE: PRT
<213> ORGANISM: Homo sapiens

<400> SEQUENCE: 17

Gln Gln Tyr Gly Ser Ser Pro Tyr Thr
1               5

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide linker

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 375
<212> TYPE: DNA
<213> ORGANISM: Homo sapiens

<400> SEQUENCE: 19
caggtgcagc tggtgcaatc tggggctgag gtgaagaagc ctgggtcctc ggtgaaagtc    60
tcctgcaaga cttctggagg cacctthcaac aatgttgcta tcaactgggt gcgccaagcc   120
cctggacaag gcttgagtg gatgggaggg atcatccctg ccttgacac accaaactac     180 gcacagaagt tccagggcag agtcactatt accgcgaca aatccacgac ttcgacctac    240
ttggagttga gtagcctgag atctgacgac acggccgtgt attactgtag cgagagatg    300 gaagtcagtg gcggtggcg gccgacagaa gcttttgaaa tctggggcca agggacaatg    360
gtcaccgtct cctca                                                    375

<210> SEQ ID NO 20
<211> LENGTH: 324
<212> TYPE: DNA
<213> ORGANISM: Homo sapiens

<400> SEQUENCE: 20
gaaacgacac tcacgcagtc tccaggcacc ctgtctttgt ctccagggga aagagccacc    60
ctctcctgca gggccagtca gactattagc aacaactttg tagcctggta tcagcagaaa   120
cctggccagg ctcccaggct cctcatctat ggtgcatcca ccaggccac tggcatccca    180 gacaggttca gtggcagtgg gtctgggaca gacttcactc tcaccatcag cagcctagag   240
cctgaagatt ttgcagtgta ttactgtgcc cagtatggta gctcaccgta cacttttggc   300
caggggacca aagtggatat caaa                                          324

<210> SEQ ID NO 21
<211> LENGTH: 451
<212> TYPE: PRT

<213> ORGANISM: Homo sapiens

<400> SEQUENCE: 21

```
Gln Val Gln Leu Val Gln Ser Gly Ala Glu Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Met Glu Val Ser Gly Arg Trp Arg Pro Thr Glu Ala Phe
            100                 105                 110

Glu Ile Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
```

-continued

```
                   405                 410                 415
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 22
<211> LENGTH: 450
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Met Glu Val Ser Gly Arg Trp Arg Pro Thr Glu Ala Phe
            100                 105                 110

Glu Ile Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ser Ser Ile
```

```
                        325                 330                 335
Glu Lys Thr Ile Ser Lys Thr Lys Gly Gln Pro Arg Glu Pro Gln Val
                    340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 23
<211> LENGTH: 215
<212> TYPE: PRT
<213> ORGANISM: Homo sapiens

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Ser Asn Asn
                20                  25                  30

Phe Val Ala Trp Tyr Gln Gln Lys Pro Gly Gln Ala Pro Arg Leu Leu
            35                  40                  45

Ile Tyr Gly Ala Ser Thr Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 24
<211> LENGTH: 16
<212> TYPE: PRT
```

-continued

<213> ORGANISM: Homo sapiens

<400> SEQUENCE: 24

Glu Met Glu Val Ser Gly Gln Trp Arg Pro Thr Glu Ala Phe Glu Ile
1               5                   10                  15

<210> SEQ ID NO 25
<211> LENGTH: 16
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be D, E or G
<220> FEATURE:
<221> NAME/KEY: MISC_FEATURE
<222> LOCATION: (2)..(2)
<223> OTHER INFORMATION: Xaa can be H, L, M, R, V or Y
<220> FEATURE:
<221> NAME/KEY: MISC_FEATURE
<222> LOCATION: (3)..(3)
<223> OTHER INFORMATION: Xaa can be E, G, L or Y
<220> FEATURE:
<221> NAME/KEY: MISC_FEATURE
<222> LOCATION: (4)..(4)
<223> OTHER INFORMATION: Xaa can be A, E, G, V or Y
<220> FEATURE:
<221> NAME/KEY: MISC_FEATURE
<222> LOCATION: (5)..(5)
<223> OTHER INFORMATION: Xaa can be A, I, N, R, S, T or Y
<220> FEATURE:
<221> NAME/KEY: MISC_FEATURE
<222> LOCATION: (6)..(6)
<223> OTHER INFORMATION: Xaa can be G, R, S or Y
<220> FEATURE:
<221> NAME/KEY: MISC_FEATURE
<222> LOCATION: (7)..(7)
<223> OTHER INFORMATION: Xaa can be D, G, Q or R
<220> FEATURE:
<221> NAME/KEY: MISC_FEATURE
<222> LOCATION: (8)..(8)
<223> OTHER INFORMATION: Xaa can be C, D, G, N, R, S, or W
<220> FEATURE:
<221> NAME/KEY: MISC_FEATURE
<222> LOCATION: (9)..(9)
<223> OTHER INFORMATION: Xaa can be G, Q, R, S or Y
<220> FEATURE:
<221> NAME/KEY: MISC_FEATURE
<222> LOCATION: (10)..(10)
<223> OTHER INFORMATION: Xaa can be G, L, P or R
<220> FEATURE:
<221> NAME/KEY: MISC_FEATURE
<222> LOCATION: (11)..(11)
<223> OTHER INFORMATION: Xaa can be A, H, P, Q or T
<220> FEATURE:
<221> NAME/KEY: MISC_FEATURE
<222> LOCATION: (12)..(12)
<223> OTHER INFORMATION: Xaa can be D, E, G, H, K, N or S
<220> FEATURE:
<221> NAME/KEY: MISC_FEATURE
<222> LOCATION: (13)..(13)
<223> OTHER INFORMATION: Xaa can be A, L, P or V
<220> FEATURE:
<221> NAME/KEY: MISC_FEATURE
<222> LOCATION: (14)..(14)
<223> OTHER INFORMATION: Xaa can be F or L
<220> FEATURE:
<221> NAME/KEY: MISC_FEATURE
<222> LOCATION: (15)..(15)
<223> OTHER INFORMATION: Xaa can be D, E or S
<220> FEATURE:
<221> NAME/KEY: MISC_FEATURE
<222> LOCATION: (16)..(16)
<223> OTHER INFORMATION: Xaa can be F, I, L or V

<400> SEQUENCE: 25

Xaa Xaa Xaa Xaa Xaa Xaa Xaa Xaa Xaa Xaa Xaa Xaa Xaa Xaa Xaa Xaa

```
<210> SEQ ID NO 26
<211> LENGTH: 8
<212> TYPE: PRT
<213> ORGANISM: Homo sapiens

<400> SEQUENCE: 26

Gln Gln Tyr Gly Ser Ser Pro Thr
1               5

<210> SEQ ID NO 27
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be H, L, M or Q
<220> FEATURE:
<221> NAME/KEY: MISC_FEATURE
<222> LOCATION: (2)..(2)
<223> OTHER INFORMATION: Xaa can be E, H, K, L, Q or R
<220> FEATURE:
<221> NAME/KEY: MISC_FEATURE
<222> LOCATION: (3)..(3)
<223> OTHER INFORMATION: Xaa can be A, F, G, R, S, T or Y
<220> FEATURE:
<221> NAME/KEY: MISC_FEATURE
<222> LOCATION: (4)..(4)
<223> OTHER INFORMATION: Xaa can be A, D, E, G, H, L, N, S, T or Y
<220> FEATURE:
<221> NAME/KEY: MISC_FEATURE
<222> LOCATION: (5)..(5)
<223> OTHER INFORMATION: Xaa can be A, D, F, H, I, N, Q, R, S, T or Y
<220> FEATURE:
<221> NAME/KEY: MISC_FEATURE
<222> LOCATION: (6)..(6)
<223> OTHER INFORMATION: Xaa can be A, D, E, H, L, P, S, T, W or Y
<220> FEATURE:
<221> NAME/KEY: MISC_FEATURE
<222> LOCATION: (7)..(7)
<223> OTHER INFORMATION: Xaa can be D, F, G, H, I, L, P, Q, R, S, V, W
    or Y
<220> FEATURE:
<221> NAME/KEY: MISC_FEATURE
<222> LOCATION: (8)..(8)
<223> OTHER INFORMATION: Xaa can be A, D, G, K, L, P, Q, S, T or V

<400> SEQUENCE: 27

Xaa Xaa Xaa Xaa Xaa Xaa Xaa Xaa
1               5

<210> SEQ ID NO 28
<211> LENGTH: 9
<212> TYPE: PRT
<213> ORGANISM: Homo sapiens

<400> SEQUENCE: 28

Gln Gln Tyr Gly Ser Ser Pro Leu Thr
1               5

<210> SEQ ID NO 29
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be E, H, L, M or Q
<220> FEATURE:
<221> NAME/KEY: MISC_FEATURE
<222> LOCATION: (2)..(2)
```

```
<223> OTHER INFORMATION: Xaa can be E, H, N, Q, R or S
<220> FEATURE:
<221> NAME/KEY: MISC_FEATURE
<222> LOCATION: (3)..(3)
<223> OTHER INFORMATION: Xaa can be A, C, D, F, G, H, L, P, R, S, T, V
      or Y
<220> FEATURE:
<221> NAME/KEY: MISC_FEATURE
<222> LOCATION: (4)..(4)
<223> OTHER INFORMATION: Xaa can be A, D, E, F, G, H, I, K, L, M, N, R,
      S, T, V or Y
<220> FEATURE:
<221> NAME/KEY: MISC_FEATURE
<222> LOCATION: (5)..(5)
<223> OTHER INFORMATION: Xaa can be A, D, E, F, G, H, I, K, L, M, N, Q,
      R, S, T, V, W or Y
<220> FEATURE:
<221> NAME/KEY: MISC_FEATURE
<222> LOCATION: (6)..(6)
<223> OTHER INFORMATION: Xaa can be A, D, F, G, I, K, L, M, N, P, Q, S,
      T, V, W or Y
<220> FEATURE:
<221> NAME/KEY: MISC_FEATURE
<222> LOCATION: (7)..(7)
<223> OTHER INFORMATION: Xaa can be A, D, E, F, G, H, I, L, M, N, P, Q,
      R, S, T or V
<220> FEATURE:
<221> NAME/KEY: MISC_FEATURE
<222> LOCATION: (8)..(8)
<223> OTHER INFORMATION: Xaa can be A, E, F, G, H, I, K, L, M, N, P, Q,
      R, S, T, V, W or Y
<220> FEATURE:
<221> NAME/KEY: MISC_FEATURE
<222> LOCATION: (9)..(9)
<223> OTHER INFORMATION: Xaa can be A, G, I, K, L, N, P, S, T or Y

<400> SEQUENCE: 29

Xaa Xaa Xaa Xaa Xaa Xaa Xaa Xaa Xaa
1               5

<210> SEQ ID NO 30
<211> LENGTH: 10
<212> TYPE: PRT
<213> ORGANISM: Homo sapiens

<400> SEQUENCE: 30

Gln Gln Tyr Gly Ser Ser Pro Pro Tyr Thr
1               5                   10

<210> SEQ ID NO 31
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be H or Q
<220> FEATURE:
<221> NAME/KEY: MISC_FEATURE
<222> LOCATION: (2)..(2)
<223> OTHER INFORMATION: Xaa can be H, Q or Y
<220> FEATURE:
<221> NAME/KEY: MISC_FEATURE
<222> LOCATION: (3)..(3)
<223> OTHER INFORMATION: Xaa can be R, S or Y
<220> FEATURE:
<221> NAME/KEY: MISC_FEATURE
<222> LOCATION: (4)..(4)
<223> OTHER INFORMATION: Xaa can be A, D, G, H, K, N, S or T
<220> FEATURE:
<221> NAME/KEY: MISC_FEATURE
<222> LOCATION: (5)..(5)
<223> OTHER INFORMATION: Xaa can be A, D, E, G, N, R, S, T or Y
<220> FEATURE:
<221> NAME/KEY: MISC_FEATURE
<222> LOCATION: (6)..(6)
```

```
<223> OTHER INFORMATION: Xaa can be A, R, S, T or W
<220> FEATURE:
<221> NAME/KEY: MISC_FEATURE
<222> LOCATION: (7)..(7)
<223> OTHER INFORMATION: Xaa can be A, I, L, P, Q, S, T or V
<220> FEATURE:
<221> NAME/KEY: MISC_FEATURE
<222> LOCATION: (8)..(8)
<223> OTHER INFORMATION: Xaa can be E, G, L, P, Q, R, S or T
<220> FEATURE:
<221> NAME/KEY: MISC_FEATURE
<222> LOCATION: (9)..(9)
<223> OTHER INFORMATION: Xaa can be D, F, G, I, L, N, R, T, V, W or Y
<220> FEATURE:
<221> NAME/KEY: MISC_FEATURE
<222> LOCATION: (10)..(10)
<223> OTHER INFORMATION: Xaa can be A, I, M, P, S, T or V

<400> SEQUENCE: 31

Xaa Xaa Xaa Xaa Xaa Xaa Xaa Xaa Xaa Xaa
1               5                   10

<210> SEQ ID NO 32
<211> LENGTH: 11
<212> TYPE: PRT
<213> ORGANISM: Homo sapiens

<400> SEQUENCE: 32

Gln Gln Tyr Gly Ser Ser Pro Pro Gly Val Thr
1               5                   10

<210> SEQ ID NO 33
<211> LENGTH: 11
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be G, Q or S
<220> FEATURE:
<221> NAME/KEY: MISC_FEATURE
<222> LOCATION: (2)..(2)
<223> OTHER INFORMATION: Xaa can be Q, S, T or V
<220> FEATURE:
<221> NAME/KEY: MISC_FEATURE
<222> LOCATION: (3)..(3)
<223> OTHER INFORMATION: Xaa can be R, W or Y
<220> FEATURE:
<221> NAME/KEY: MISC_FEATURE
<222> LOCATION: (4)..(4)
<223> OTHER INFORMATION: Xaa can be D, G, S or T
<220> FEATURE:
<221> NAME/KEY: MISC_FEATURE
<222> LOCATION: (5)..(5)
<223> OTHER INFORMATION: Xaa can be G, N, S or T
<220> FEATURE:
<221> NAME/KEY: MISC_FEATURE
<222> LOCATION: (6)..(6)
<223> OTHER INFORMATION: Xaa can be S or W
<220> FEATURE:
<221> NAME/KEY: MISC_FEATURE
<222> LOCATION: (7)..(7)
<223> OTHER INFORMATION: Xaa can be G, L, P, S or T
<220> FEATURE:
<221> NAME/KEY: MISC_FEATURE
<222> LOCATION: (8)..(8)
<223> OTHER INFORMATION: Xaa can be D, L, P, R, S or T
<220> FEATURE:
<221> NAME/KEY: MISC_FEATURE
<222> LOCATION: (9)..(9)
<223> OTHER INFORMATION: Xaa can be A, D, G, H, L, M, R or S
<220> FEATURE:
<221> NAME/KEY: MISC_FEATURE
<222> LOCATION: (10)..(10)
<223> OTHER INFORMATION: Xaa can be F, I, L, V or Y
<220> FEATURE:
```

```
<221> NAME/KEY: MISC_FEATURE
<222> LOCATION: (11)..(11)
<223> OTHER INFORMATION: Xaa can be A, T or V

<400> SEQUENCE: 33

Xaa Xaa Xaa Xaa Xaa Xaa Xaa Xaa Xaa Xaa
1               5                   10

<210> SEQ ID NO 34
<211> LENGTH: 16
<212> TYPE: PRT
<213> ORGANISM: Homo sapiens

<400> SEQUENCE: 34

Glu Ser Glu Val Ser Gly Arg Trp Arg Pro Thr Glu Ala Phe Glu Ile
1               5                   10                  15

<210> SEQ ID NO 35
<211> LENGTH: 125
<212> TYPE: PRT
<213> ORGANISM: Homo sapiens

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 36
<211> LENGTH: 125
<212> TYPE: PRT
<213> ORGANISM: Homo sapiens

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Leu Glu Val Ser Gly Arg Trp Arg Pro Thr Glu Ala Phe
            100                 105                 110
```

```
Glu Ile Trp Gly Gln Gly Thr Leu Val Thr Val Ser Ser
        115                 120                 125

<210> SEQ ID NO 37
<211> LENGTH: 125
<212> TYPE: PRT
<213> ORGANISM: Homo sapiens

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 38
<211> LENGTH: 125
<212> TYPE: PRT
<213> ORGANISM: Homo sapiens

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 39
<211> LENGTH: 125
<212> TYPE: PRT
<213> ORGANISM: Homo sapiens

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
```

```
                 20                  25                  30
Ala Ile Asn Trp Val Arg Gln Ala Pro Gly Gln Gly Leu Glu Trp Met
                 35                  40                  45

Gly Gly Ile Ile Pro Gly Leu Asp Thr Pro Asn Tyr Ala Gln Lys Phe
             50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Glu Val Ser Gly Arg Trp Arg Pro Thr Glu Ala Phe
                100                 105                 110

Glu Ile Trp Gly Gln Gly Thr Leu Val Thr Val Ser Ser
                115                 120                 125

<210> SEQ ID NO 40
<211> LENGTH: 125
<212> TYPE: PRT
<213> ORGANISM: Homo sapiens

<400> SEQUENCE: 40

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Asn Asn Val
                 20                  25                  30

Ala Ile Asn Trp Val Arg Gln Ala Pro Gly Gln Gly Leu Glu Trp Met
                 35                  40                  45

Gly Gly Ile Ile Pro Gly Leu Asp Thr Pro Asn Tyr Ala Gln Lys Phe
             50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Ala Glu Val Ser Gly Arg Trp Arg Pro Thr Glu Ala Phe
                100                 105                 110

Glu Ile Trp Gly Gln Gly Thr Leu Val Thr Val Ser Ser
                115                 120                 125

<210> SEQ ID NO 41
<211> LENGTH: 125
<212> TYPE: PRT
<213> ORGANISM: Homo sapiens

<400> SEQUENCE: 41

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Asn Asn Val
                 20                  25                  30

Ala Ile Asn Trp Val Arg Gln Ala Pro Gly Gln Gly Leu Glu Trp Met
                 35                  40                  45

Gly Gly Ile Ile Pro Gly Leu Asp Thr Pro Asn Tyr Ala Gln Lys Phe
             50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Cys Glu Val Ser Gly Arg Trp Arg Pro Thr Glu Ala Phe
                100                 105                 110
```

-continued

Glu Ile Trp Gly Gln Gly Thr Leu Val Thr Val Ser Ser
        115                 120                 125

<210> SEQ ID NO 42
<211> LENGTH: 125
<212> TYPE: PRT
<213> ORGANISM: Homo sapiens

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 43
<211> LENGTH: 125
<212> TYPE: PRT
<213> ORGANISM: Homo sapiens

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 44
<211> LENGTH: 125
<212> TYPE: PRT
<213> ORGANISM: Homo sapiens

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val

```
              20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Phe Glu Val Ser Gly Arg Trp Arg Pro Thr Glu Ala Phe
            100                 105                 110

Glu Ile Trp Gly Gln Gly Thr Leu Val Thr Val Ser Ser
            115                 120                 125

<210> SEQ ID NO 45
<211> LENGTH: 125
<212> TYPE: PRT
<213> ORGANISM: Homo sapiens

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Val Ser Gly Arg Trp Arg Pro Thr Glu Ala Phe
            100                 105                 110

Glu Ile Trp Gly Gln Gly Thr Leu Val Thr Val Ser Ser
            115                 120                 125

<210> SEQ ID NO 46
<211> LENGTH: 125
<212> TYPE: PRT
<213> ORGANISM: Homo sapiens

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ile Glu Val Ser Gly Arg Trp Arg Pro Thr Glu Ala Phe
            100                 105                 110
```

Glu Ile Trp Gly Gln Gly Thr Leu Val Thr Val Ser Ser
        115                 120                 125

<210> SEQ ID NO 47
<211> LENGTH: 125
<212> TYPE: PRT
<213> ORGANISM: Homo sapiens

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Lys Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 48
<211> LENGTH: 125
<212> TYPE: PRT
<213> ORGANISM: Homo sapiens

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asn Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 49
<211> LENGTH: 125
<212> TYPE: PRT
<213> ORGANISM: Homo sapiens

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val

```
                    20                  25                  30

Ala Ile Asn Trp Val Arg Gln Ala Pro Gly Gln Gly Leu Glu Trp Met
            35                  40                  45

Gly Gly Ile Ile Pro Gly Leu Asp Thr Pro Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Pro Glu Val Ser Gly Arg Trp Arg Pro Thr Glu Ala Phe
            100                 105                 110

Glu Ile Trp Gly Gln Gly Thr Leu Val Thr Val Ser Ser
            115                 120                 125

<210> SEQ ID NO 50
<211> LENGTH: 125
<212> TYPE: PRT
<213> ORGANISM: Homo sapiens

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
            35                  40                  45

Gly Gly Ile Ile Pro Gly Leu Asp Thr Pro Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gln Glu Val Ser Gly Arg Trp Arg Pro Thr Glu Ala Phe
            100                 105                 110

Glu Ile Trp Gly Gln Gly Thr Leu Val Thr Val Ser Ser
            115                 120                 125

<210> SEQ ID NO 51
<211> LENGTH: 125
<212> TYPE: PRT
<213> ORGANISM: Homo sapiens

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
            35                  40                  45

Gly Gly Ile Ile Pro Gly Leu Asp Thr Pro Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Glu Val Ser Gly Arg Trp Arg Pro Thr Glu Ala Phe
            100                 105                 110
```

```
Glu Ile Trp Gly Gln Gly Thr Leu Val Thr Val Ser Ser
        115                 120                 125

<210> SEQ ID NO 52
<211> LENGTH: 125
<212> TYPE: PRT
<213> ORGANISM: Homo sapiens

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 53
<211> LENGTH: 125
<212> TYPE: PRT
<213> ORGANISM: Homo sapiens

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Trp Glu Val Ser Gly Arg Trp Arg Pro Thr Glu Ala Phe
            100                 105                 110

Glu Ile Trp Gly Gln Gly Thr Leu Val Thr Val Ser Ser
        115                 120                 125

<210> SEQ ID NO 54
<211> LENGTH: 16
<212> TYPE: PRT
<213> ORGANISM: Homo sapiens

<400> SEQUENCE: 54

Glu Val Glu Val Ser Gly Arg Trp Arg Pro Thr Glu Ala Phe Glu Ile
1               5                   10                  15
```

```
<210> SEQ ID NO 55
<211> LENGTH: 16
<212> TYPE: PRT
<213> ORGANISM: Homo sapiens

<400> SEQUENCE: 55

Glu Leu Glu Val Ser Gly Arg Trp Arg Pro Thr Glu Ala Phe Glu Ile
1               5                   10                  15

<210> SEQ ID NO 56
<211> LENGTH: 16
<212> TYPE: PRT
<213> ORGANISM: Homo sapiens

<400> SEQUENCE: 56

Glu Arg Glu Val Ser Gly Arg Trp Arg Pro Thr Glu Ala Phe Glu Ile
1               5                   10                  15

<210> SEQ ID NO 57
<211> LENGTH: 16
<212> TYPE: PRT
<213> ORGANISM: Homo sapiens

<400> SEQUENCE: 57

Glu His Glu Val Ser Gly Arg Trp Arg Pro Thr Glu Ala Phe Glu Ile
1               5                   10                  15

<210> SEQ ID NO 58
<211> LENGTH: 16
<212> TYPE: PRT
<213> ORGANISM: Homo sapiens

<400> SEQUENCE: 58

Glu Tyr Glu Val Ser Gly Arg Trp Arg Pro Thr Glu Ala Phe Glu Ile
1               5                   10                  15

<210> SEQ ID NO 59
<211> LENGTH: 16
<212> TYPE: PRT
<213> ORGANISM: Homo sapiens

<400> SEQUENCE: 59

Glu Ala Glu Val Ser Gly Arg Trp Arg Pro Thr Glu Ala Phe Glu Ile
1               5                   10                  15

<210> SEQ ID NO 60
<211> LENGTH: 16
<212> TYPE: PRT
<213> ORGANISM: Homo sapiens

<400> SEQUENCE: 60

Glu Cys Glu Val Ser Gly Arg Trp Arg Pro Thr Glu Ala Phe Glu Ile
1               5                   10                  15

<210> SEQ ID NO 61
<211> LENGTH: 16
<212> TYPE: PRT
<213> ORGANISM: Homo sapiens

<400> SEQUENCE: 61

Glu Asp Glu Val Ser Gly Arg Trp Arg Pro Thr Glu Ala Phe Glu Ile
1               5                   10                  15

<210> SEQ ID NO 62
<211> LENGTH: 16
<212> TYPE: PRT
```

<213> ORGANISM: Homo sapiens

<400> SEQUENCE: 62

Glu Glu Glu Val Ser Gly Arg Trp Arg Pro Thr Glu Ala Phe Glu Ile
1               5                   10                  15

<210> SEQ ID NO 63
<211> LENGTH: 16
<212> TYPE: PRT
<213> ORGANISM: Homo sapiens

<400> SEQUENCE: 63

Glu Phe Glu Val Ser Gly Arg Trp Arg Pro Thr Glu Ala Phe Glu Ile
1               5                   10                  15

<210> SEQ ID NO 64
<211> LENGTH: 16
<212> TYPE: PRT
<213> ORGANISM: Homo sapiens

<400> SEQUENCE: 64

Glu Gly Glu Val Ser Gly Arg Trp Arg Pro Thr Glu Ala Phe Glu Ile
1               5                   10                  15

<210> SEQ ID NO 65
<211> LENGTH: 16
<212> TYPE: PRT
<213> ORGANISM: Homo sapiens

<400> SEQUENCE: 65

Glu Ile Glu Val Ser Gly Arg Trp Arg Pro Thr Glu Ala Phe Glu Ile
1               5                   10                  15

<210> SEQ ID NO 66
<211> LENGTH: 16
<212> TYPE: PRT
<213> ORGANISM: Homo sapiens

<400> SEQUENCE: 66

Glu Lys Glu Val Ser Gly Arg Trp Arg Pro Thr Glu Ala Phe Glu Ile
1               5                   10                  15

<210> SEQ ID NO 67
<211> LENGTH: 16
<212> TYPE: PRT
<213> ORGANISM: Homo sapiens

<400> SEQUENCE: 67

Glu Asn Glu Val Ser Gly Arg Trp Arg Pro Thr Glu Ala Phe Glu Ile
1               5                   10                  15

<210> SEQ ID NO 68
<211> LENGTH: 16
<212> TYPE: PRT
<213> ORGANISM: Homo sapiens

<400> SEQUENCE: 68

Glu Pro Glu Val Ser Gly Arg Trp Arg Pro Thr Glu Ala Phe Glu Ile
1               5                   10                  15

<210> SEQ ID NO 69
<211> LENGTH: 16
<212> TYPE: PRT
<213> ORGANISM: Homo sapiens

<400> SEQUENCE: 69

Glu Gln Glu Val Ser Gly Arg Trp Arg Pro Thr Glu Ala Phe Glu Ile
1               5                   10                  15

<210> SEQ ID NO 70
<211> LENGTH: 16
<212> TYPE: PRT
<213> ORGANISM: Homo sapiens

<400> SEQUENCE: 70

Glu Ser Glu Val Ser Gly Arg Trp Arg Pro Thr Glu Ala Phe Glu Ile
1               5                   10                  15

<210> SEQ ID NO 71
<211> LENGTH: 319
<212> TYPE: PRT
<213> ORGANISM: Staphylococcus aureus (strain USA300 / TCH1516)

<400> SEQUENCE: 71

Met Lys Thr Arg Ile Val Ser Ser Val Thr Thr Thr Leu Leu Leu Gly
1               5                   10                  15

Ser Ile Leu Met Asn Pro Val Ala Asn Ala Ala Asp Ser Asp Ile Asn
                20                  25                  30

Ile Lys Thr Gly Thr Thr Asp Ile Gly Ser Asn Thr Thr Val Lys Thr
            35                  40                  45

Gly Asp Leu Val Thr Tyr Asp Lys Glu Asn Gly Met His Lys Lys Val
    50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
            100                 105                 110

Gln Leu Gln Leu Pro Asp Asn Glu Val Ala Gln Ile Ser Asp Tyr Tyr
    115                 120                 125

Pro Arg Asn Ser Ile Asp Thr Lys Glu Tyr Met Ser Thr Leu Thr Tyr
130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
    195                 200                 205

Asp Arg Asp Ser Trp Asn Pro Val Tyr Gly Asn Gln Leu Phe Met Lys
210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
    275                 280                 285

Thr Asn Trp Lys Gly Thr Asn Thr Lys Asp Lys Trp Ile Asp Arg Ser
290                 295                 300

```
Ser Glu Arg Tyr Lys Ile Asp Trp Glu Lys Glu Met Thr Asn
305                 310                 315
```

<210> SEQ ID NO 72
<211> LENGTH: 451
<212> TYPE: PRT
<213> ORGANISM: Homo sapiens

<400> SEQUENCE: 72

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Glu Val Ser Gly Arg Trp Arg Pro Thr Glu Ala Phe
            100                 105                 110

Glu Ile Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 73
<211> LENGTH: 450
<212> TYPE: PRT
<213> ORGANISM: Homo sapiens

<400> SEQUENCE: 73

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Val
            20                  25                  30

Ala Ile Asn Trp Val Arg Gln Ala Pro Gly Gln Gly Leu Glu Trp Met
        35                  40                  45

Gly Gly Ile Ile Pro Gly Leu Asp Thr Pro Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Glu Val Ser Gly Arg Trp Arg Pro Thr Glu Ala Phe
            100                 105                 110

Glu Ile Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

```
His Asn Ala Lys Thr Lys Pro Arg Glu Glu Gln Phe Asn Ser Thr Phe
            290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly
    450

<210> SEQ ID NO 74
<211> LENGTH: 293
<212> TYPE: PRT
<213> ORGANISM: Staphylococcus aureus

<400> SEQUENCE: 74

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205
```

-continued

```
Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290
```

STAPHYLOCOCCUS AUREUS SPECIFIC ANTIBODIES AND USES THEREOF

This application claims priority, under 35 USC §119(e), to U.S. Provisional Application Ser. No. 61/579,548, filed Dec. 22, 2011, and U.S. Provisional Application Ser. No. 61/692,626, filed Aug. 23, 2012, hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "SequenceListingPC71803A.txt" created on Nov. 16, 2012 and having a size of 65 KB. The sequence listing contained in this .txt file is part of the specification and is herein incorporated by reference in its entirety.

FIELD

The present invention relates to antibodies, e.g., full length antibodies that bind *Staphylococcus aureus* (*S. aureus*) alpha-toxin. The invention further relates to compositions comprising antibodies to alpha-toxin, and methods of using alpha-toxin antibodies as a medicament. The alpha-toxin antibodies are useful for treating and preventing staphylococcal disease.

BACKGROUND

Most pathogens in humans are Gram-positive organisms. One important member of the Gram-positive pathogens is *S. aureus*. About 20% of the population is a long-term carrier of *S. aureus*. *S. aureus* can cause a range of illnesses from minor skin infections, such as pimples, impetigo, boils, cellulitis folliculitis, furuncles, carbuncles, scalded skin syndrome, atopic dermatitis, and abscesses, to life-threatening diseases such as pneumonia, meningitis, osteomyelitis, endocarditis, and septicemia. *S. aureus* is capable of infecting all kinds of organs and tissues. *S. aureus* infections occur in immunocompetent as well as immune compromised people. About 50% of the infections in US intensive care units are caused by this pathogen. Three hundred thousand *S. aureus* infections per year, resulting in 12,000 deaths, are reported in the US (see, e.g., Moran et al., 2006, NEJM 355, 666-674).

*S. aureus* strains produce many secreted toxins important for virulence. One important virulence factor in the pathogenesis of *S. aureus* infection is alpha-toxin. Alpha-toxin is a member of a family of bacterial cytotoxins that is secreted by *S. aureus* and is capable of inserting into the cell membrane of a multitude of eukaryotic cells. The protein is secreted as a monomer; however, it assembles into a ring structure on the surface of eukaryotic cells. The assembled toxin inserts into the host cell membrane, forming a pore that contributes to cellular injury and death by disrupting the integrity of the membrane. Several biochemical studies have defined the amino acid residues within the alpha-toxin monomer that facilitate binding to the host cell, ring formation and host cell lysis. Recent work investigated the impact of alpha-toxin antibodies on the outcome of pneumonia (Bubeck Wardenburg and Schneewind, 2008, J. Exp. Med. 205:287-294; Ragle and Bubeck Wardenburg, 2009, Infect. Immun. 77:2712-2718). It has been reported that passive immunization with monoclonal antibodies to the N-terminus of alpha-toxin substantially reduced mortality in a mouse model for *S. aureus* pneumonia (Ragle and Bubeck Wardenburg, 2009, Infect. Immun. 77:2712-2718).

The clinical complexity of *S. aureus* infection and the fact that there is no single virulence factor central to the progression of all disease manifestations pose a challenge for development of therapeutics. There remains a need in the art for compositions and methods for preventing and/or treating *S. aureus* infection, as well as the attenuation or amelioration of the secondary effects of such an infection.

SUMMARY

Antibodies that selectively interact with *S. aureus* alpha-toxin are provided. It is demonstrated that certain alpha-toxin antibodies are effective in vivo to prevent and/or treat staphylococcal diseases. Advantageously, the alpha-toxin antibodies provided herein are effective against different strains of *S. aureus*, including methicillin-resistant *S. aureus* (MRSA) and methicillin-sensitive *S. aureus* strains (MSSA), including strains producing variant alpha-toxin sequences.

Isolated antibodies that specifically bind to *S. aureus* alpha-toxin and bind to an epitope that is the same as or overlaps with the epitope on *S. aureus* alpha-toxin recognized by monoclonal antibody DF2 are provided herein. The antagonist antibody can be, for example, a human, humanized, or chimeric antibody.

In some embodiments, the antibody binds to alpha-toxin with an equilibrium dissociation constant of about 250 nM or less. In some embodiments, the antibody binds to alpha-toxin with an equilibrium dissociation constant of about 100 nM or less. In some embodiments, the antibody binds to alpha-toxin with an equilibrium dissociation constant of about 1 nM or less. In some embodiments, the antibody binds to alpha-toxin with an equilibrium dissociation constant of about 100 pM or less. In some embodiments, the antibody binds to alpha-toxin with an equilibrium dissociation constant of about 40 pM or less. In some embodiments, the antibody binds to alpha-toxin with an equilibrium dissociation constant of about 20 pM or less. In some embodiments, the antibody binds to alpha-toxin with an equilibrium dissociation constant of about 10 pM or less. In some embodiments, the antibody binds to alpha-toxin with an equilibrium dissociation constant of about 2 pM or less. In some embodiments, the antibody binds to alpha-toxin from MRSA strains and to alpha-toxin from MSSA strains.

In some embodiments, the antibody blocks alpha-toxin from binding to a cell membrane. In some embodiments, the antibody blocks alpha-toxin-induced ADAM10 activity.

In some embodiments, the invention provides an antibody that recognizes a first epitope of *S. aureus* alpha-toxin that is the same as, or overlaps with, a second epitope that is recognized by monoclonal antibody DF1.1.

In some embodiments, the invention provides an antibody to *S. aureus* alpha-toxin, wherein the antibody recognizes an epitope comprising amino acid residues 30-32, 64-72, 78-79, 205, 207-208, 210-213, 253, 274, and 276 of the alpha-toxin amino acid sequence shown in SEQ ID NO: 74. In some embodiments, the antibody recognizes an epitope comprising amino acid residues R66, E70, and D276 of alpha-toxin.

In some embodiments, the antibody comprises a heavy chain variable region (VH) complementarity determining region three (CDR3) sequence of SEQ ID NO: 54 and variants thereof wherein the amino acid at position 1 is D, E or G; the amino acid at position 2 is H, L, M, R, V or Y; the amino acid at position 3 is E, G, L or Y; the amino acid at position 4 is A, E, G, V or Y; the amino acid at position 5 is A, I, N, R, S, T or Y; the amino acid at position 6 is G, R, S or Y; the amino acid at position 7 is D, G, Q or R; the amino acid at position 8 is C, D, G, N, R, S, or W; the amino acid at position 9 is G, Q, R, S or Y; the amino acid at position 10 is G, L, P or R; the amino acid at position 11 is A, H, P, Q or T; the amino acid at position 12 is D, E, G, H, K, N or S; the amino acid at position 13 is A, L, P or V; the amino acid at position 14 is F or L; the amino acid at position 15 is D, E or S; and the amino acid at position 16 is F, I, L or V.

In some embodiments, the antibody can comprise a VH CDR1 comprising the amino acid sequence of SEQ ID NO: 5, 6 or 7; and a VH CDR2 comprising the amino acid sequence of SEQ ID NO: 8 or 9.

In some embodiments, the antibody can comprise a light chain variable region (VL) derived from a human germline Vκ sequence selected from the group consisting of IGKV3-20, IGKV3-15, IGKV1-39, IGKV3-11, IGKV2-28, IGKV1-12, IGKV1-9, IGKV4-1, IGKV3D-20, IGLV1-40, IGKV1-5, IGKV3-NL5, IGKV1-17, IGKV3-NL1, IGKV1-6, IGKV2-40, IGKV1-33, IGKV1-27, IGLV2-14, IGLV6-57, IGLV1-51, IGKV6-21, IGLV1-47, IGLV3-21, IGLV1-44, IGKV1D-16, IGKV1-13, IGKV3-NL4, IGKV2-24, and IGKV1-8.

In some embodiments, the isolated antibody comprises a light chain variable region (VL) complementarity determining region three (CDR3) sequence of SEQ ID NO: 17 and variants thereof wherein the amino acid at position 1 is E, H, L, M or Q; the amino acid at position 2 is E, H, N, Q, R or S; the amino acid at position 3 is A, C, D, F, G, H, L, P, R, S, T, V or Y; the amino acid at position 4 is A, D, E, F, G, H, I, K, L, M, N, R, S, T, V or Y; the amino acid at position 5 is A, D, E, F, G, H, I, K, L, M, N, Q, R, S, T, V, W or Y; the amino acid at position 6 is A, D, F, G, I, K, L, M, N, P, Q, S, T, V, W or Y; the amino acid at position 7 is A, D, E, F, G, H, I, L, M, N, P, Q, R, S, T or V; the amino acid at position 8 is A, E, F, G, H, I, K, L, M, N, P, Q, R, S, T, V, W or Y; and the amino acid at position 9 is A, G, I, K, L, N, P, S, T or Y.

In some embodiments, the isolated antibody specifically binds to alpha-toxin and comprises: a heavy chain variable region (VH) comprising a VH complementarity determining region one (CDR1), VH CDR2, and VH CDR3 of the VH sequence of SEQ ID NO: 35; and a light chain variable region (VL) comprising a VL CDR1, VL CDR2, and VL CDR3. In some emdodiments, the VL comprises a VL CDR1, VL CDR2, and VL CDR3 of the VL sequence of SEQ ID NO: 3. In some embodiments the VH CDR1 comprises the amino acid sequence of SEQ ID NO: 5, 6 or 7, the VH CDR2 comprises the amino acid sequence of SEQ ID NO: 8 or 9, the VH CDR3 comprises the amino acid sequence of SEQ ID NO: 54, the VL CDR1 comprises the amino acid sequence of SEQ ID NO: 15, the VL CDR2 comprises the amino acid sequence of SEQ ID NO: 16, and the VL CDR3 comprises the amino acid sequence of SEQ ID NO: 17. In some embodiments the VH comprises the amino acid sequence of SEQ ID NO: 35 or a variant thereof with one or several conservative amino acid substitutions in residues that are not within a CDR. In some embodiments the VL comprises the amino acid sequence of SEQ ID NO: 3 or a variant thereof with one or several amino acid substitutions in amino acids that are not within a CDR.

In some embodiments, the antibody comprises three CDRs of SEQ ID NO: 35. In some embodiments, the antibody comprises three CDRs of SEQ ID NO: 3. In some embodiments, the antibody comprises three CDRs of SEQ ID NO: 35 and three CDRs of SEQ ID NO: 3.

In some embodiments, the antibody can further comprise an immunologically inert constant region. In some embodiments, the antibody can have an isotype that is selected from the group consisting of $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P and $IgG_{4\Delta c}$ S228P. In some embodiments, the constant region can be aglycosylated Fc. In some embodiments the antibody can comprise a heavy chain comprising the amino acid sequence of SEQ ID NO: 72 or 73 and a light chain comprising the amino acid sequence of SEQ ID NO: 23.

The invention also provides pharmaceutical compositions comprising any of the alpha-toxin antagonist antibodies described herein.

The invention also provides cell lines that recombinantly produce any of the alpha-toxin antagonist antibodies described herein.

The invention also provides nucleic acids encoding any of the alpha-toxin antagonist antibodies described herein. The invention also provides nucleic acids encoding a heavy chain variable region and/or a light chain variable region of any of the alpha-toxin antagonist antibodies described herein.

The invention also provides kits comprising an effective amount of any of the alpha-toxin antagonist antibodies described herein.

Also provided are methods of protecting an individual from a staphylococcal disease. In some embodiments, the method comprises administering to an individual suffering from a staphylococcal disease an effective amount of an alpha-toxin antagonist antibody described herein. In some embodiments, the method comprises administering to an individual at risk for a staphylococcal disease an effective amount of an alpha-toxin antagonist antibody described herein. In some embodiments, the method comprises administering to an individual infected by S. aureas an effective amount of an alpha-toxin antagonist antibody described herein. In some embodiments, the method comprises administering an effective amount of one or more alpha-toxin antagonist antibodies to the individual.

Also provided are alpha-toxin antagonist antibodies for use in the treatment or prevention of a staphylococcal disease.

In some embodiments, the individual can be a human. In some embodiments, the individual can be a mammal, such as, e.g., a cow, a pig, a cat, or a dog.

The staphylococcal disease can be, for example, staphylococcal abscess, staphylococcal bacteremia, staphylococcal sepsis, staphylococcal eye infection, staphylococcal skin infection, staphylococcal soft tissue infection, staphylococcal mastitis, staphylococcal osteomyelitis, staphylococcal arthritis, and staphylococcal lung disease. The staphylococcal lung disease can be, for example, pneumonia. The staphylococcal eye infection can be, for example, keratitis. The staphylococcal abscess can be, for example, skin abscess.

In some embodiments, the individual can be a dairy cow, and the staphylococcal disease can be mastitis.

The staphylococcal disease can be cause by, for example, a MRSA or MSSA strain.

In some embodiments, the method can further comprise administering an effective amount of an antiinfective agent, an antibiotic agent, and an antimicrobial agent. The agent can be, for example, linezolid, vancomycin, methicillin, doxycycline, lysostaphin, clindamycin, and penicillin.

In some embodiments, the antibody can be administered parenterally. In some embodiments, the antibody can be administered topically.

BRIEF DESCRIPTION OF THE
FIGURES/DRAWINGS

FIG. 1 depicts a table summarizing heavy chain variable region CDR3 (VH CDR3) results of deep sequencing analysis of alpha-toxin antibodies identified by panning a phage library.

FIG. 2 depicts a table summarizing light chain variable region CDR3 (VL CDR3) results of deep sequencing analysis of alpha-toxin antibodies identified by panning a phage library.

FIG. 3 depicts a table summarizing VL CDR3 results of deep sequencing analysis of alpha-toxin antibodies identified by panning a phage library.

FIG. 4 depicts a table summarizing VL CDR3 results of deep sequencing analysis of alpha-toxin antibodies identified by panning a phage library.

FIG. 5 depicts a table summarizing VL CDR3 results of deep sequencing analysis of alpha-toxin antibodies identified by panning a phage library.

FIG. 6 depicts a table summarizing results of sequencing analysis of alpha-toxin from various S. aureus strains.

Figures 7A, 7B:
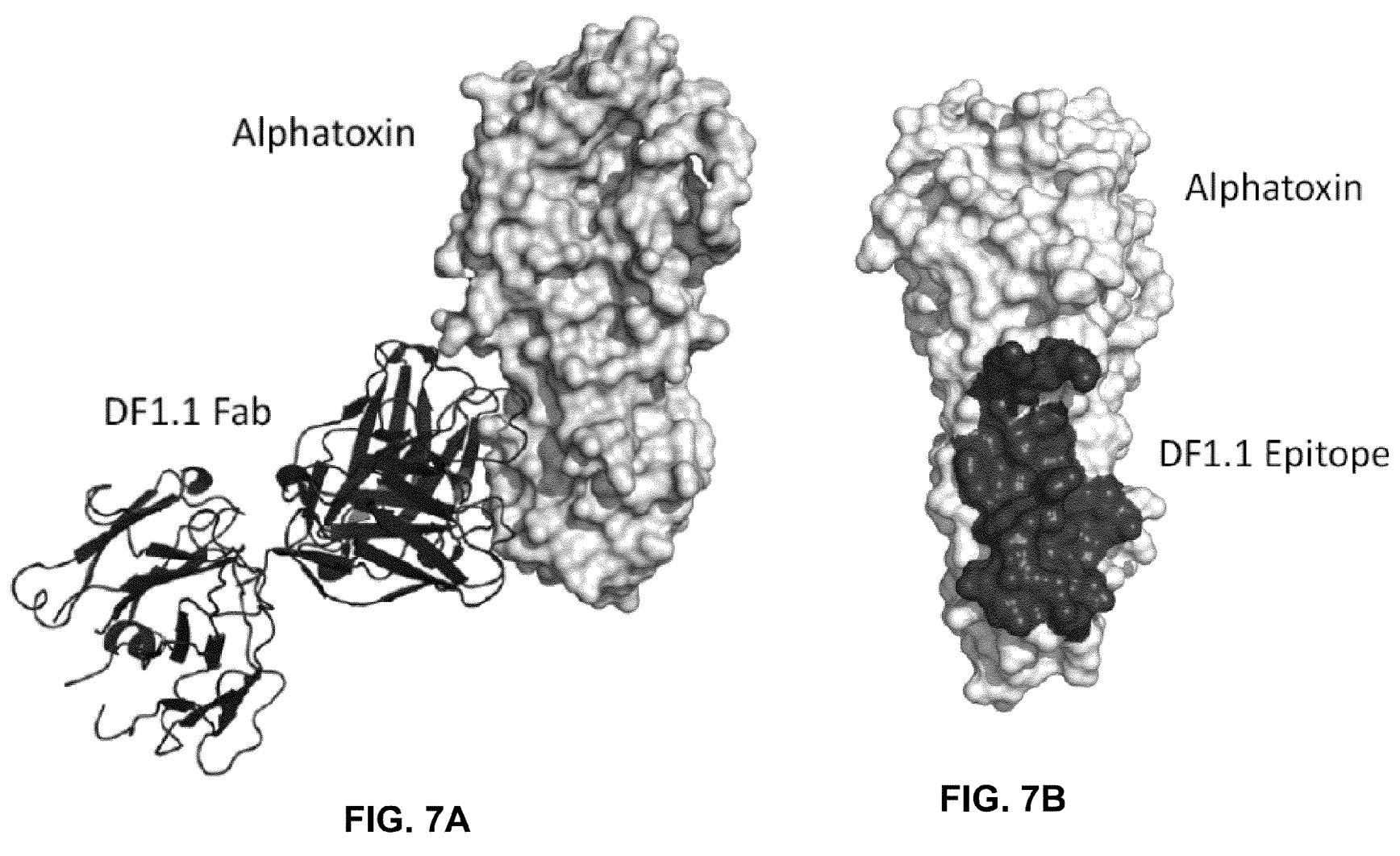

FIG. 7A depicts the crystal structure of the alpha-toxin ("Alphatoxin"—light gray surface representation) bound to the DF1.1 antibody (black cartoon representation). FIG. 7B depicts the surface area representation of alpha-toxin with the DF1.1 epitope shown in dark gray.

FIG. 8A depicts a graph summarizing results of a membrane binding assay. FIG. 8B depicts the contribution of the DF1.1 heavy and light chains to alpha-toxin binding. DF1.1 Fab is shown in surface representation with heavy chain shown in black and light chain is in white. Alpha-toxin is shown as gray ribbon representation.

Figure 9:
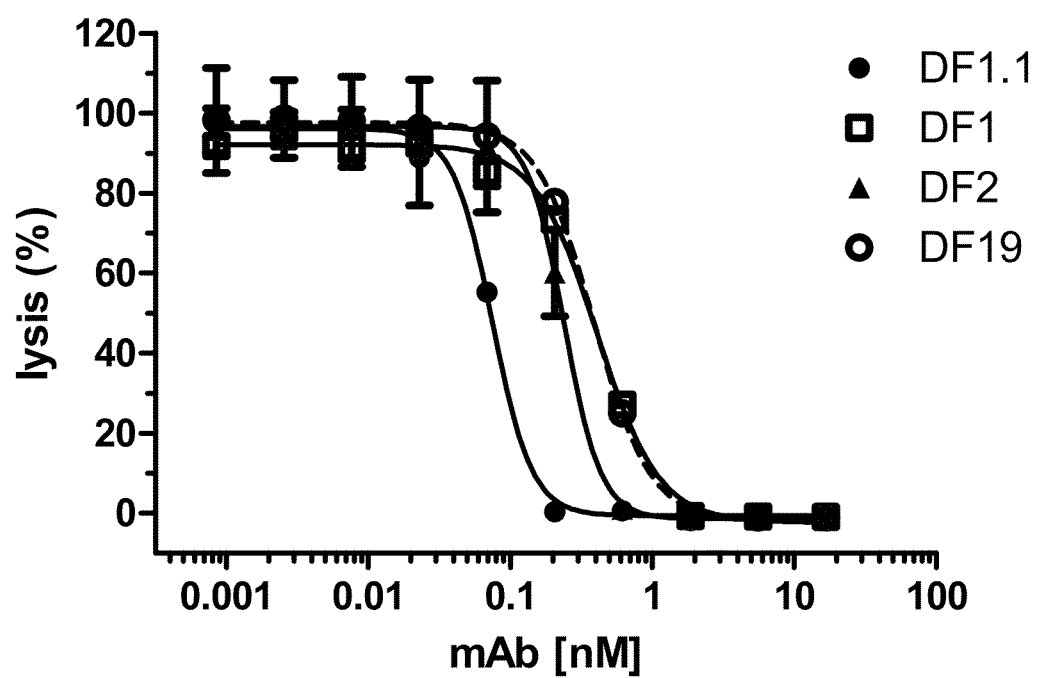

FIG. 9 depicts a graph summarizing results of an in vitro rabbit erythrocyte lysis assay.

Figure 10:
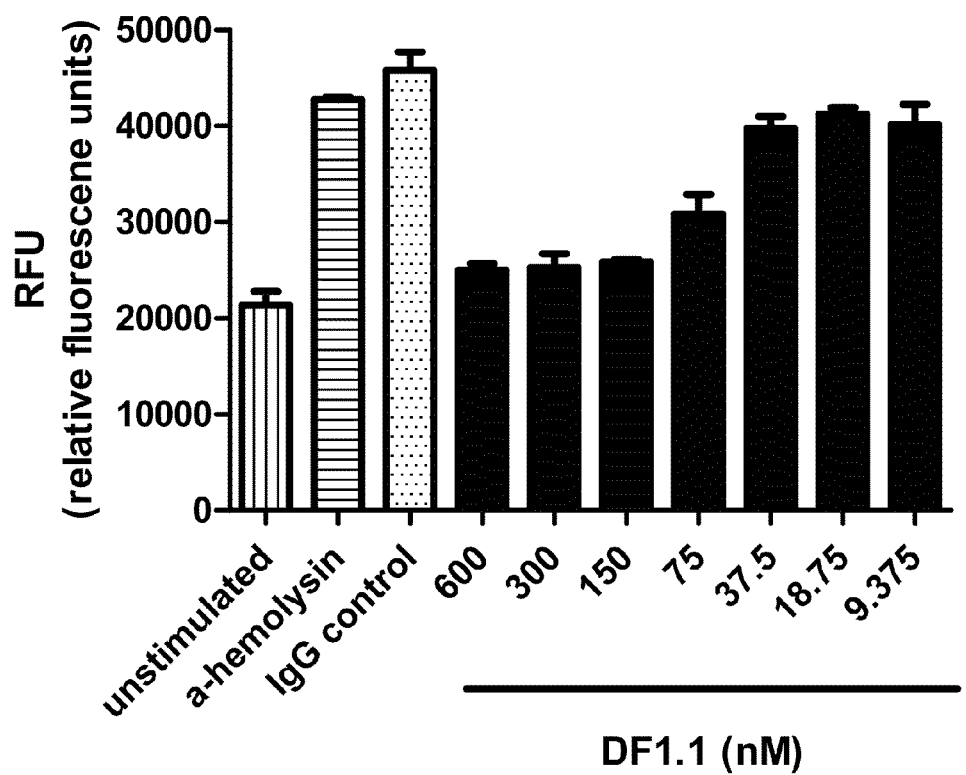

FIG. 10 depicts a graph summarizing results of an ADAM10 metalloprotease assay.

DETAILED DESCRIPTION

Disclosed herein are antibodies that specifically bind to alpha-toxin. Methods of making alpha-toxin antibodies, compositions comprising these antibodies, and methods of using these antibodies as a medicament are provided. Alpha-toxin antibodies can be used in the prevention and/or treatment of illnesses caused by S. aureus, including, e.g., bacteremia, dermonecrosis, meningitis, osteomyelitis, endocarditis, TSS, septicemia, septic arthritis, mastitis, pimples, impetigo, boils, cellulitis folliculitis, furuncles, carbuncles, abscesses, eye infections, and lung diseases, including, e.g., pneumonia.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DEFINITIONS

The following terms, unless otherwise indicated, shall be understood to have the following meanings: the term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also, unless otherwise specified, any antigen binding portion thereof that competes with the intact antibody for specific binding, fusion proteins comprising an antigen binding portion, and any other modified configuration of the immunoglobulin molecule that comprises an antigen recognition site. Antigen binding portions include, for example, Fab, Fab', F(ab')$_2$, Fd, Fv, domain antibodies (dAbs, e.g., shark and camelid antibodies), fragments including complementarity determining regions (CDRs), single chain variable fragment antibodies (scFv), maxibodies, minibodies, intrabodies, diabodies, triabodies, tetrabodies, v-NAR and bis-scFv, and polypeptides that contain at least a portion of an immunoglobulin that is sufficient to confer specific antigen binding to the polypeptide. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$ and IgA$_2$. The heavy-chain constant regions that correspond to the different classes of immunoglobulins are called alpha, delta, epsilon, gamma, and mu, respectively. The subunit structures and three-dimensional configurations of different classes of immunoglobulins are well known.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4): 901-917, 1987).

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. In certain embodiments, various methods of analysis can be employed to identify or approximate the CDR regions. Examples of such methods include, but are not limited to, the Kabat definition, the Chothia definition, the AbM definition, the contact definition, and the conformational definition.

The Kabat definition is a standard for numbering the residues in an antibody and is typically used to identify CDR regions. See, e.g., Johnson & Wu, 2000, Nucleic Acids Res., 28: 214-8. The Chothia definition is similar to the Kabat definition, but the Chothia definition takes into account positions of certain structural loop regions. See, e.g., Chothia et al., 1986, J. Mol. Biol., 196: 901-17; Chothia et al., 1989, Nature, 342: 877-83. The AbM definition uses an integrated suite of computer programs produced by Oxford Molecular Group that model antibody structure. See, e.g., Martin et al., 1989, Proc Natl Acad Sci (USA), 86:9268-9272; "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As known in the art, a "constant region" of an antibody refers to the constant region of the antibody light chain or the constant region of the antibody heavy chain, either alone or in combination.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example. As used herein, "humanized" antibody refers to forms of non-human (e.g. murine) antibodies that are chimeric immunoglobulins, immunoglobulin chains, or fragments thereof (such as Fv, Fab, Fab', $F(ab')_2$ or other antigen-binding subsequences of antibodies) that contain minimal sequence derived from non-human immunoglobulin. Preferably, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. The humanized antibody may comprise residues that are found neither in the recipient antibody nor in the imported CDR or framework sequences, but are included to further refine and optimize antibody performance.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "epitope" refers to that portion of a molecule capable of being recognized by and bound by an antibody at one or more of the antibody's antigen-binding regions. Epitopes often consist of a surface grouping of molecules such as amino acids or sugar side chains and have specific three-dimensional structural characteristics as well as specific charge characteristics. In some embodiments, the epitope can be a protein epitope. Protein epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds. The term "antigenic epitope" as used herein, is defined as a portion of an antigen to which an antibody can specifically bind as determined by any method well known in the art, for example, by conventional immunoassays. Once a desired epitope on an antigen is determined, it is possible to generate antibodies to that epitope, e.g., using the techniques described in the present specification. Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to alpha-toxin, e.g., the antibodies compete for binding to the antigen.

As used herein, the term "alpha-toxin" (interchangeably termed "α-toxin", "a-toxin", "α-hemolysin", "Hla", "a-hemolysin" or "alpha-hemolysin") refers to any form of alpha-toxin and variants thereof that retain at least part of the activity of alpha-toxin. Unless indicated differently, such as by specific reference to a specific strain of S. aureus alpha-toxin, alpha-toxin includes native sequences of all S. aureus strains, for example, USA300 (LAC), PFESA0140, USA300 (FPR3757), PFESA0181, PFESA0158, PFESA0124, PFESA0207, PFESA0150, and PFESA0249, PFESA0184, PFESA0163, PFESA0174, PFESA0141, PFESA0204, PFESA0009, PFESA0102, PFESA0125, PFESA0146, PFESA0067, PFESA0218, USA100, USA500, EMRSA-15 EMRSA-16, ST5, ST75, ST152, ST239, ST398, ST425, and TW20. One exemplary alpha-toxin is found as UniProt accession number: A8Z1U4 (SEQ ID NO: 71).

The term "antagonist antibody" refers to an antibody that binds to a target and prevents or reduces the biological effect of that target. In some embodiments, the term can denote an antibody that prevents the target, e.g., alpha-toxin, to which it is bound from performing a biological function.

As used herein, an "alpha-toxin antagonist antibody" refers to an antibody that is able to inhibit alpha-toxin biological activity and/or downstream events(s) mediated by alpha-toxin. Alpha-toxin antagonist antibodies encompass antibodies that block, antagonize, suppress or reduce (to any degree including significantly) alpha-toxin biological activity, including downstream events mediated by alpha-toxin, such as cell surface interaction, receptor binding and downstream signaling, pore formation, and cell lysis. For purposes of the present invention, it will be explicitly understood that the term "alpha-toxin antagonist antibody" (interchangeably termed "antagonist alpha-toxin antibody", "antagonist anti-alpha-toxin antibody" or "anti-alpha-toxin antagonist antibody") encompasses all the previously identified terms, titles, and functional states and characteristics whereby the alpha-toxin itself, an alpha-toxin biological activity (including but not limited to its ability to bind a cell, bind a receptor, form a pore, and lyse cells), or the consequences of the biological activity, are substantially nullified, decreased, or neutralized in any meaningful degree. In some embodiments, an alpha-toxin antibody binds alpha-toxin and prevents pore formation. In some embodiments, the antagonist ability is characterized and/or described via a cell lysis or viability assay. In some embodiments, the antagonist ability is described in terms of an $IC_{50}$ or $EC_{50}$ value. Examples of alpha-toxin antibodies are provided herein.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O) OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, an antibody "interacts with" alpha-toxin when the equilibrium dissociation constant is equal to or less than 20 nM, preferably less than about 6 nM, more preferably less than about 1 nM, most preferably less than about 0.2 nM, as measured by the methods disclosed herein in Example 3.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an alpha-toxin epitope is an antibody that binds this epitope with greater affinity, avidity, more readily, and/or with greater duration than it binds to other alpha-toxin epitopes or non-alpha-toxin epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

A "functional Fc region" possesses at least one effector function of a native sequence Fc region. Exemplary "effector functions" include Clq binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

As used herein, "staphylococcal disease" refers to a disease, infection or condition caused by S. aureus. Examples of staphylococcal disease include, without limitation, staphylococcal bloodstream infections, including, e.g., bacteremia and septicemia; staphylococcal lung disease, including, e.g., staphylococcal pneumonia; staphylococcal abscess, including, e.g., skin abscess, abdominal abscess, breast abscess, kidney abscess, heart abscess, liver abscess, lung abscess, brain abscess, and spleen abscess; staphylococcal skin infections, including, e.g., pimples, abscess, impetigo, boils, furuncles, cellulitis, atopic dermatitis, and dermonecrosis; staphylococcal eye infections, including, e.g., keratitis, blepharitis, conjunctivitis, and endophthalmitis; staphylococcal sepsis; septic arthritis, staphylococcal central nervous system (CNS) infections; mastitis; endocarditis; osteomyelitis; chorioamnionitis; neonatal sepsis; staphylococcal food poisoning; urinary tract infection; mastitis; TSS and meningitis.

As used herein, "treatment" is an approach for obtaining beneficial or desired clinical results. For purposes of this invention, beneficial or desired clinical results include, but are not limited to, one or more of the following: improved survival rate (reduced mortality), reduction in proinflammatory response to the disease, reduction in size of abscess, improvement in the appearance of the disease lesions, limitation of the pathological lesions to focal sites, decreased extent of damage from the disease, decreased duration of the disease, decreased number of bacteria recoverable from the site of infection, reduction in the number of days spent in an intensive care unit, reduction in the number of days spent on a mechanical ventilator, and/or reduction in the number, extent, or duration of symptoms related to the disease.

As used herein, the phrase "protecting an individual" refers to preventing, treating, reducing the severity of, and/or ameliorating a staphylococcal disease in an individual. Unless otherwise indicated, it also refers to preventing or delaying mortality attributable to the disease, decreasing the number of bacteria recoverable from the affected site (e.g., lung, skin, breast, etc.), limiting the pathological lesions to focal sites, decreasing the extent of damage from the disease, decreasing the duration of the disease, and/or reducing the number, extent, or duration of symptoms related to the disease. Embodiments of the invention that are implemented in the context of a human patient may also be implemented with respect to any mammalian subject, including, for example, a cow (e.g., a dairy cow, a beef cow, etc.), a pig, a cat, or a dog. In some embodiments, an individual has or is at risk of developing a disease associated with S. aureus.

"Reducing incidence" means any of reducing severity (which can include reducing need for and/or amount of (e.g., exposure to) other drugs and/or therapies generally used for this condition), reducing duration, and/or reducing frequency. As is understood by those skilled in the art, individuals may vary in terms of their response to treatment, and, as such, for example, a "method of reducing incidence" reflects administering the alpha-toxin antagonist antibody based on a reasonable expectation that such administration may likely cause such a reduction in incidence in that particular individual.

"Ameliorating" means a lessening or improvement of one or more symptoms as compared to not administering an alpha-toxin antagonist antibody. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. In more specific aspects, an effective amount prevents, alleviates or ameliorates symptoms of disease or infection, and/or prolongs the survival of the subject being treated. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing one or more symptoms of staphylococcal disease, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals (e.g., cows, pigs, horses, chickens, etc.), sport animals, pets, primates, horses, dogs, cats, mice and rats. In some embodiments, the individual is considered to be at risk for a staphylococcal disease. Such individuals include, but are not limited to, an individual who is hospitalized or will be hospitalized, an individual who is or will be put in an intensive care unit, an individual who will undergo surgery, an individual who will be anesthetized or under general anesthesia, an individual on dialysis, an individual with an indwelling catheter, an individual over the age of 65, an individual with a compromised immune system, a pediatric individual, an individual who is or may be put on a respirator or other mechanical ventilator, an individual in whom an endotracheal tube will or has been placed, an individual who is or will be immobilized, an individual who will undergo, is undergoing, or has undergone chemotherapy or myeloablative therapy, and an individual who will take, is taking, or has taken one or more immunosuppressants, particularly for a significant period of time (longer than a month).

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, refers to the rate constant for association of an antibody to an antigen. Specifically, the rate constants ($k_{on}$ and $k_{off}$) and equilibrium dissociation constants are measured using full-length antibodies and/or Fab antibody fragments (i.e. univalent) and alpha-toxin.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

Exemplary methods and materials are described herein, although methods and materials similar or equivalent to those described herein can also be used in the practice or testing of the present invention. The materials, methods, and examples are illustrative only and not intended to be limiting.

Methods for Preventing or Treating Staphylococcal Disease

In one aspect, the invention provides a method for treating or preventing staphylococcal disease in an individual, the method comprising administering to the individual an effective amount of an alpha-toxin antagonist antibody. In some embodiments, the staphylococcal disease is staphylococcal abscess, including, e.g., skin abscess, abdominal abscess, breast abscess, kidney abscess, heart abscess, liver abscess, lung abscess, brain abscess, and spleen abscess. In other embodiments, the staphylococcal disease is staphylococcal bacteremia. In other embodiments, the staphylococcal disease is staphylococcal sepsis. In other embodiments, the staphylococcal disease is staphylococcal pneumonia. In other embodiments, the staphylococcal disease is staphylococcal osteomyelitis. In other embodiments, the staphylococcal disease is staphylococcal endocarditis. In other embodiments, the staphylococcal disease is staphylococcal keratitis, blepharitis, conjunctivitis, or endophthalmitis. In other embodiments, the staphylococcal disease is septic arthritis. In other embodiments, the staphylococcal disease is staphylococcal CNS infection.

In some embodiments, the individual involved in methods of the invention is considered to be at risk for a staphylococcal disease. Such individuals include, but are not limited to, an individual who is hospitalized or will be hospitalized, an individual who is or will be put in an intensive care unit, an individual who will undergo surgery, an individual who will be anesthetized or under general anesthesia, an individual over the age of 65, an individual with a compromised immune system, a pediatric individual, an individual who is or may be put on a respirator or other mechanical ventilator, an individual in whom an endotracheal tube will or has been placed, an individual who is or will be immobilized, an individual who will undergo, is undergoing, or has undergone chemotherapy or radiation/myeloablative therapy, an individual who will take, is taking, or has taken one or more immunosuppressants, particularly for a significant period of time (longer than a month), an individual with an infected wound, an individual with a minor injury, an individual who has an existing infection anywhere in the body, an individual who is or will be catheterized (e.g., with a urinary or indwelling IV catheter), an individual who will undergo a dental procedure, an individual who has an incised boil, an individual who has had his spleen removed, an individual taking steroids, an individual with diabetes, an individual with AIDS, and individual with cirrhosis, an individual with burns, and individual with severe injuries, and an individual with an infection such as, for example, pneumonia, meningitis, cellulitis, or urinary tract infection.

In some embodiments, methods may involve identifying an individual at risk for a staphylococcal disease. Additionally, methods may include evaluating an individual for risk factors for a staphylococcal disease, evaluating an individual for symptoms of a staphylococcal disease, or diagnosing the individual with a staphylococcal disease. In certain embodiments, methods may involve implementing steps in which the disease is staphylococcal pneumonia, staphylococcal abscess, bacteremia, sepsis, osteomyelitis, endocarditis, or keratitis.

In some embodiments, therapeutic administration of the alpha-toxin antagonist antibody advantageously results in reduced incidence and/or amelioration of one or more symptoms of staphylococcal pneumonia including, for example, cough, difficulty breathing, fever, fatigue, coughing up yellow and/or bloody mucus, chest pain that worsens with breathing, malaise, headache, earache, sore throat, rash, chills, and shortness of breath.

An individual suffering from or at risk for staphylococcal pneumonia can be treated with an alpha-toxin antagonist antibody. An individual suitable for alpha-toxin antagonist antibody therapy is selected using clinical criteria and prognostic indicators of staphylococcal pneumonia that are well known in the art. Assessment of staphylococcal pneumonia severity may be performed based on tests known in the art, including, for example, chest X-ray, examination of sputum, pulse oximetry, chest radiography, complete blood count, serum electrolyte count, c-reactive protein test, tests to specifically identify an *S. aureus* strain, microbiological cultures of sputum, analysis of protected brush bronchial specimens, liver function tests, lung biopsy, immunochromatographic assay, and immunohistochemistry. In some embodiments, ameliorating, controlling, reducing incidence of, or delaying the development or progression of staphylococcal pneumonia is measured by a combination of physical signs and a chest X-ray.

In some embodiments, therapeutic administration of the alpha-toxin antagonist antibody advantageously results in reduced incidence and/or amelioration of one or more symptoms of staphylococcal abscess including, for example, pain, swelling, tenderness, nodule, lump, pus, mastalgia (breast abscess), and nipple discharge (breast abscess), fever, chills, abdominal pain, nausea, vomiting, dermonecrosis, and diarrhea.

An individual suffering from or at risk for staphylococcal abscess can be treated with an alpha-toxin antagonist antibody. An individual suitable for alpha-toxin antagonist antibody therapy is selected using clinical criteria and prognostic indicators of staphylococcal abscess that are well known in the art. Assessment of staphylococcal abscess severity may be performed based on tests known in the art. In some embodiments, ameliorating, controlling, reducing incidence of, or delaying the development or progression of staphylococcal abscess and/or symptoms of staphylococcal abscess is measured by examination of the lesion.

In some embodiments, therapeutic administration of the alpha-toxin antagonist antibody advantageously results in reduced incidence and/or amelioration of one or more symptoms of staphylococcal bacteremia including, for example, fever, chills, malaise, abdominal pain, nausea, vomiting, diarrhea, anxiety, shortness of breath and confusion.

An individual suffering from or at risk for staphylococcal bacteremia can be treated with an alpha-toxin antagonist antibody. An individual suitable for alpha-toxin antagonist antibody therapy is selected using clinical criteria and prognostic indicators of staphylococcal bacteremia that are well known in the art, including blood culture to check for presence of bacteria. Assessment of staphylococcal bacteremia severity may be performed based on tests known in the art.

In some embodiments, therapeutic administration of the alpha-toxin antagonist antibody advantageously results in reduced incidence and/or amelioration of one or more symptoms of staphylococcal sepsis including, for example, fever, chills, shaking, rapid heart beat, rapid breathing, low blood pressure, confusion, disorientation, agitation, dizziness, decreased urination, rash, and joint pain.

An individual suffering from or at risk for staphylococcal sepsis can be treated with an alpha-toxin antagonist antibody. An individual suitable for alpha-toxin antagonist antibody therapy is selected using clinical criteria and prognostic indicators of staphylococcal sepsis that are well known in the art. Assessment of staphylococcal sepsis severity may be performed based on tests known in the art, including blood culture to detect bacteria, sampling of sputum, urine, spinal fluid and/or abscess contents to detect bacteria, chest X-ray, and CT scan. In some embodiments, ameliorating, controlling, reducing incidence of, or delaying the development or progression of staphylococcal sepsis and/or symptoms of staphylococcal sepsis is measured by blood culture analysis.

With respect to all methods described herein, reference to alpha-toxin antagonist antibodies also includes compositions comprising one or more additional agents. These compositions may further comprise suitable excipients, such as pharmaceutically acceptable excipients including buffers, which are well known in the art. The present invention can be used alone or in combination with other methods of treatment.

The alpha-toxin antagonist antibody can be administered to an individual via any suitable route. It should be apparent to a person skilled in the art that the examples described herein are not intended to be limiting but to be illustrative of the techniques available. Accordingly, in some embodiments, the alpha-toxin antagonist antibody is administered to an individual in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, alpha-toxin antagonist antibody can be aerosolized using a fluorocarbon formulation and a metered dose inhaler, or inhaled as a lyophilized and milled powder.

In some embodiments, an alpha-toxin antagonist antibody is administered via site-specific or targeted local delivery techniques. Examples of site-specific or targeted local delivery techniques include various implantable depot sources of the alpha-toxin antagonist antibody or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an alpha-toxin antagonist antibody may be used for administration. In some embodiments, the alpha-toxin antagonist antibody may be administered neat. In some embodiments, alpha-toxin antagonist antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An alpha-toxin antagonist antibody can be administered using any suitable method, including by injection (e.g., intraperitoneally, intravenously, subcutaneously, intramuscularly, etc.). Alpha-toxin antibodies can also be administered topically or via inhalation, as described herein. Generally, for administration of alpha-toxin antibodies, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce symptoms associated with staphylococcal disease. The progress of this therapy is easily monitored by conventional techniques and assays. The dosing regimen (including the alpha-toxin antagonist antibody used) can vary over time.

For the purpose of the present invention, the appropriate dosage of an alpha-toxin antagonist antibody will depend on the alpha-toxin antagonist antibody (or compositions thereof) employed, the type and severity of symptoms to be treated, whether the agent is administered for preventive or therapeutic purposes, previous therapy, the patient's clinical history and response to the agent, the amount of S. aureus present at the disease site, the patient's clearance rate for the administered agent, and the discretion of the attending physician. Typically the clinician will administer an alpha-toxin antagonist antibody until a dosage is reached that achieves the desired result. Dose and/or frequency can vary over course of treatment. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms. Alternatively, sustained continuous release formulations of alpha-toxin antagonist antibodies may be appropriate. Various formulations and devices for achieving sustained release are known in the art.

In one embodiment, dosages for an antagonist antibody may be determined empirically in individuals who have been given one or more administration(s) of an antagonist antibody. Individuals are given incremental dosages of an alpha-toxin antagonist antibody. To assess efficacy, an indicator of the disease can be followed.

Administration of an alpha-toxin antagonist antibody in accordance with the method in the present invention can be continuous or intermittent, depending, for example, upon the recipient's physiological condition, whether the purpose of the administration is therapeutic or prophylactic, and other factors known to skilled practitioners. The administration of an alpha-toxin antagonist antibody may be essentially continuous over a preselected period of time or may be in a series of spaced doses.

In some embodiments, more than one alpha-toxin antagonist antibody may be present. At least one, at least two, at least three, at least four, at least five different, or more antagonist antibodies can be present. Generally, those alpha-toxin antagonist antibodies may have complementary activities that do not adversely affect each other. An alpha-toxin antagonist antibody can also be used in conjunction with other antibodies to S. aureas, and/or other therapies. An alpha-toxin antagonist antibody can also be used in conjunction with other agents that serve to enhance and/or complement the effectiveness of the agents.

In some embodiments, the alpha-toxin antagonist antibody may be administered in combination with the administration of traditional therapies. These include, but are not limited to, the administration of antibiotics such as methicillin, linezolid, torezolid, eperezolid, posizolid, radezolid, streptomycin, neomycin, kanamycin, spectinomycin, paromomycin, gentamycin, verdamicin, astromicin, ciprofloxacin, daptomycin, doxycycline, chlortetracycline, clomocycline, demeclocycline, lymecycline, meclocycline, metacycline, minocycline, oxytetracycline, penimepicycline, rolitetracycline, tetracycline, tigecycline, chloramphenicol, azidamfenicol, thiamphenicol, florfenicol, retapamulin, tiamulin, valnemulin, erythromycin, azithromycin, spiramycin, midecamycin, oleandomycin, roxithromycin, josamycin, troleandomycin, clarithromycin, miocamycin, rokitamycin, dirithromycin, flurithromycin, ketolide (e.g., telithromycin, cethromycin, and solithromycin), clindamycin, lincomycin, pristinamycin, ampicillin, oxacillin, fusidic acid, virginiamycin, quinupristin, dalfopristin, vancomycin, penicillin, trimethoprim, sulfamethoxazole, or various combinations of antibiotics. Administration of alpha-toxin antagonist antibodies to an individual may be used in combination with the administration of antivirulence agents, such as the RNAIII-inhibiting heptapeptide (RIP).

In some embodiments, an alpha-toxin antagonist antibody is used in conjunction with antibacterial and/or antivirulence treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Therapeutic formulations of the alpha-toxin antagonist antibody used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing, 2000), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the alpha-toxin antagonist antibody are prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic alpha-toxin antagonist antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing an alpha-toxin antagonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Alpha-Toxin Antagonist Antibodies

The methods of the invention use an alpha-toxin antagonist antibody that blocks, suppresses or reduces (including significantly reduces) alpha-toxin biological activity, including downstream events mediated by alpha-toxin. An alpha-toxin antagonist antibody should exhibit any one or more of the following characteristics: (a) bind to alpha-toxin; (b) block alpha-toxin oligomerization; (c) block alpha-toxin interaction with a cell surface receptor and downstream signaling events; (d) block alpha-toxin interaction with the cell surface; (e) block pore formation; (f) block alpha-toxin mediated cell lysis; and (g) block alpha-toxin mediated cell death.

For purposes of this invention, the antibody preferably reacts with alpha-toxin in a manner that blocks alpha-toxin interaction with a cell surface. In some embodiments, the alpha-toxin antagonist antibody specifically recognizes alpha-toxin from a methicillin-resistant *S. aureus* strain (e.g., USA300) and alpha-toxin from a methicillin sensitive *S. aureus* strain (e.g., PFESA0140). In some embodiments, the alpha-toxin antagonist antibody binds USA300 alpha-toxin and PFESA0140 alpha-toxin. Preferably, the alpha-toxin antagonist antibody binds one or more different alpha-toxin variants.

The antibodies useful in the present invention can encompass monoclonal antibodies, polyclonal antibodies, antibody fragments (e.g., Fab, Fab', F(ab')$_2$, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, the alpha-toxin antagonist antibody is a monoclonal antibody. In some embodiments, the antibody is a human or humanized antibody.

The alpha-toxin antagonist antibodies may be made by any method known in the art. General techniques for production of human and mouse antibodies are known in the art and/or are described herein.

Alpha-toxin antagonist antibodies can be identified or characterized using methods known in the art, whereby reduction, amelioration, or neutralization of alpha-toxin biological activity is detected and/or measured. In some embodiments, an alpha-toxin antagonist antibody is identified by incubating a candidate agent with alpha-toxin and monitoring binding and/or attendant reduction or neutralization of a biological activity of alpha-toxin. The binding assay may be performed with, e.g., purified alpha-toxin polypeptide(s), or with cells naturally expressing (e.g., various S. aureus strains), or transfected to express, alpha-toxin polypeptide(s). In one embodiment, the binding assay is a competitive binding assay, where the ability of a candidate antibody to compete with a known alpha-toxin antagonist antibody for alpha-toxin binding is evaluated. The assay may be performed in various formats, including the ELISA format. In some embodiments, an alpha-toxin antagonist antibody is identified by incubating a candidate antibody with alpha-toxin and monitoring binding.

Following initial identification, the activity of a candidate alpha-toxin antagonist antibody can be further confirmed and refined by bioassays, known to test the targeted biological activities. In some embodiments, an in vitro cell or cytotoxicity assay is used to further characterize a candidate alpha-toxin antagonist antibody. For example, a candidate antibody is incubated with alpha-toxin, rabbit erythrocytes are added, and attendant cell lysis is monitored. Alternatively, bioassays can be used to screen candidates directly. Some of the methods for identifying and characterizing alpha-toxin antagonist antibody are described in detail in the Examples.

The alpha-toxin antagonist antibodies of the invention exhibit one or more of the following characteristics: (a) bind to alpha-toxin; (b) block alpha-toxin oligomerization; (c) block alpha-toxin interaction with a cell surface receptor (e.g., ADAM10) and the downstream signaling events; (d) block alpha-toxin interaction with the cell surface (e.g., block alpha-toxin from binding to a cell membrane); (e) block pore formation; (f) block alpha-toxin mediated cell lysis; and (g) block alpha-toxin mediated cell death. Preferably, alpha-toxin antibodies have two or more of these features. More preferably, the antibodies have three or more of the features. More preferably, the antibodies have four or more of the features. More preferably, the antibodies have five or more of the features. More preferably, the antibodies have six or more of the features. Most preferably, the antibodies have all seven characteristics.

Alpha-toxin antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an alpha-toxin antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an alpha-toxin antagonist antibody. In another example, the epitope to which the alpha-toxin antagonist antibody binds can be determined in a systematic screening by using overlapping peptides derived from the alpha-toxin sequence and determining binding by the alpha-toxin antagonist antibody. According to the gene fragment expression assays, the open reading frame encoding alpha-toxin is fragmented either randomly or by specific genetic constructions and the reactivity of the expressed fragments of alpha-toxin with the antibody to be tested is determined. The gene fragments may, for example, be produced by PCR and then transcribed and translated into protein in vitro, in the presence of radioactive amino acids. The binding of the antibody to the radioactively labeled alpha-toxin fragments is then determined by immunoprecipitation and gel electrophoresis. Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding. For example, alanine scanning mutagenesis experiments can be performed using a mutant alpha-toxin in which various residues of the alpha-toxin polypeptide have been replaced with alanine. By assessing binding of the antibody to the mutant alpha-toxin, the importance of the particular alpha-toxin residues to antibody binding can be assessed.

Yet another method which can be used to characterize an alpha-toxin antagonist antibody is to use competition assays with other antibodies known to bind to the same antigen, i.e., various fragments on alpha-toxin, to determine if the alpha-toxin antagonist antibody binds to the same epitope as other antibodies. Competition assays are well known to those of skill in the art.

The binding affinity ($K_D$) of an alpha-toxin antagonist antibody to alpha-toxin can be about 0.001 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, about 2 pM, or about 1 pM. In some embodiments, the binding affinity is less than any of about 250 nM, about 200 nM, about 100 nM, about 50 nM, about 10 nM, about 1 nM, about 500 pM, about 100 pM, about 50 pM, about 20 pM, about 10 pM, about 5 pM, or about 2 pM.

Accordingly, the invention provides any of the following, or compositions (including pharmaceutical compositions) comprising an antibody having a partial light chain sequence and a partial heavy chain sequence as found in Table 1, or variants thereof. In Table 1, the underlined sequences are CDR sequences according to Kabat, and the sequences in bold are CDR sequences according to Chothia. The KD values shown in Table 1 were calculated by Log 2 divided by $k_{off}$ ($T_{1/2}$=Log 2/$K_{off}$). $K_{off}$ of each antibody (measured as full length IgG2ΔA) was measured at 37° C. on a Biacore™ T200.

TABLE 1

| mAb | Light Chain | Heavy Chain | KD (1/M) |
|---|---|---|---|
| DF1.1 | ETTLTQSPGTLSLSPGERATLS CRASQTISNNFVAWYQQKPG QAPRLLIYGASTRATGIPDRFS GSGSGTDFTLTISSLEPEDFAV YYCQQYGSSPYTFGQGTKVDI K (SEQ ID NO: 1) | QVQLVQSGAEVKKPGSSVKVSC KTSGGTFNNVAINWVRQAPGQG LEWMGGIIPGLDTPNYAQKFQGR VTITADKSTTSTYLELSSLRSDDT AVYYCAREMEVSGRWRPTEAFEI WGQGTMVTVSS (SEQ ID NO: 2) | |
| DF1 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREMEVSGRWRPTEAFEI WGQGTLVTVSS (SEQ ID NO: 4) | 1.60E-09 |
| DF2 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREVEVSGRWRPTEAFEI WGQGTLVTVSS (SEQ ID NO: 35) | 7.70E-10 |
| DF3 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCARELEVSGRWRPTEAFEI WGQGTLVTVSS (SEQ ID NO: 36) | 1.50E-09 |
| DF4 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREREVSGRWRPTEAFEI WGQGTLVTVSS (SEQ ID NO: 37) | 2.40E-08 |
| DF5 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREHEVSGRWRPTEAFEI WGQGTLVTVSS (SEQ ID NO: 38) | |
| DF6 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREYEVSGRWRPTEAFEI WGQGTLVTVSS (SEQ ID NO: 39) | 1.50E-09 |
| DF7 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREAEVSGRWRPTEAFEI WGQGTLVTVSS (SEQ ID NO: 40) | 1.10E-09 |
| DF8 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCARECEVSGRWRPTEAFEI WGQGTLVTVSS (SEQ ID NO: 41) | |
| DF9 | EIVLTQSPGTLSLSPGERATLS CRASQTISNNFVAWYQQKPG | QVQLVQSGAEVKKPGSSVKVSC KASGGTFNNVAINWVRQAPGQG | 4.10E-08 |

TABLE 1-continued

| mAb | Light Chain | Heavy Chain | KD (1/M) |
|---|---|---|---|
| | QAPRLLIYGASTRATGIPDRFS GSGSGTDFTLTISRLEPEDFAV YYCQQYGSSPYTFGQGTKLEI K (SEQ ID NO: 3) | LEWMGGIIPGLDTPNYAQKFQGR VTITADESTSTAYMELSSLRSEDT AVYYCAREDEVSGRWRPTEAFEI WGQGTLVTVSS (SEQ ID NO: 42) | |
| DF10 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREEEVSGRWRPTEAFEI WGQGTLVTVSS (SEQ ID NO: 43) | 3.60E-09 |
| DF11 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREFEVSGRWRPTEAFEI WGQGTLVTVSS (SEQ ID NO: 44) | 3.20E-09 |
| DF12 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREGEVSGRWRPTEAFEI WGQGTLVTVSS (SEQ ID NO: 45) | 9.40E-09 |
| DF13 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREIEVSGRWRPTEAFEI WGQGTLVTVSS (SEQ ID NO: 46) | 1.60E-09 |
| DF14 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREKEVSGRWRPTEAFEI WGQGTLVTVSS (SEQ ID NO: 47) | |
| DF15 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCARENEVSGRWRPTEAFEI WGQGTLVTVSS (SEQ ID NO: 48) | 2.90E-09 |
| DF16 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREPEVSGRWRPTEAFEI WGQGTLVTVSS (SEQ ID NO: 49) | 2.30E-08 |
| DF17 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCAREQEVSGRWRPTEAFEI WGQGTLVTVSS (SEQ ID NO: 50) | 4.30E-09 |
| DF18 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCARESEVSGRWRPTEAFEI WGQGTLVTVSS (SEQ ID NO: 51) | 1.50E-09 |
| DF19 | EIVLTQSPGTLSLSPGERATLS CRASQTISNNFVAWYQQKPG QAPRLLIYGASTRATGIPDRFS GSGSGTDFTLTISRLEPEDFAV YYCQQYGSSPYTFGQGTKLEI K (SEQ ID NO: 3) | QVQLVQSGAEVKKPGSSVKVSC KASGGTFNNVAINWVRQAPGQG LEWMGGIIPGLDTPNYAQKFQGR VTITADESTSTAYMELSSLRSEDT AVYYCARETEVSGRWRPTEAFEI WGQGTLVTVSS (SEQ ID NO: 52) | 1.40E-09 |
| DF20 | EIVLTQSPGTLSLSPGERATLS CRASQTISNNFVAWYQQKPG | QVQLVQSGAEVKKPGSSVKVSC KASGGTFNNVAINWVRQAPGQG | 9.30E-09 |

TABLE 1-continued

| mAb | Light Chain | Heavy Chain | KD (1/M) |
|---|---|---|---|
| | QAPRLLIYGASTRATGIPDRFS GSGSGTDFTLTISRLEPEDFAV YYCQQYGSSPYTFGQGTKLEI K (SEQ ID NO: 3) | LEWMGGIIPGLDTPNYAQKFQGR VTITADESTSTAYMELSSLRSEDT AVYYCAREWEVSGRWRPTEAFEI WGQGTLVTVSS (SEQ ID NO: 53) | |

The invention also provides CDR portions of antibodies to alpha-toxin. Determination of CDR regions is well within the skill of the art. It is understood that in some embodiments, CDRs can be a combination of the Kabat and Chothia CDR (also termed "combined CDRs" or "extended CDRs"). In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. In general, "conformational CDRs" include the residue positions in the Kabat CDRs and Vernier zones which are constrained in order to maintain proper loop structure for the antibody to bind a specific antigen. Determination of conformational CDRs is well within the skill of the art. In some embodiments, the CDRs are the Kabat CDRs. In other embodiments, the CDRs are the Chothia CDRs. In other embodiments, the CDRs are the extended, AbM, conformational, or contact CDRs. In other words, in embodiments with more than one CDR, the CDRs may be any of Kabat, Chothia, extended, AbM, conformational, contact CDRs or combinations thereof.

In some embodiments, the antibody comprises three CDRs of any one of the heavy chain variable regions shown in Table 1. In some embodiments, the antibody comprises three CDRs of any one of the light chain variable regions shown in Table 1. In some embodiments, the antibody comprises three CDRs of any one of the heavy chain variable regions shown in Table 1, and three CDRs of any one of the light chain variable regions shown in Table 1.

Table 2 provides examples of CDR sequences of alpha-toxin antagonist antibodies provided herein. Additional examples of CDR sequences are described in Example 2 below.

TABLE 2

Alpha-toxin antagonist antibodies and antigen-binding CDR sequences according to Kabat (underlined) and Chothia (bold)

| MAb | | CDR1 | CDR2 | CDR3 |
|---|---|---|---|---|
| DF1.1 | HC | GGTFNNNVAIN (SEQ ID NOs: 5 (whole), 6 and 7) | GIIPGLDTPNYAQKF QG (SEQ ID NOs: 8 and 9) | EMEVSGRWRPTEAF EI (SEQ ID NO: 10) |
| | LC | RASQTISNNFVA (SEQ ID NO: 15) | GASTRAT (SEQ ID NO: 16) | QQYGSSPYT (SEQ ID NO: 17) |
| DF1 | HC | GGTFNNNVAIN (SEQ ID NOs: 5 (whole), 6 and 7) | GIIPGLDTPNYAQKF QG (SEQ ID NOs: 8 and 9) | EMEVSGRWRPTEAF EI (SEQ ID NO: 10) |
| | LC | RASQTISNNFVA (SEQ ID NO: 15) | GASTRAT (SEQ ID NO: 16) | QQYGSSPYT (SEQ ID NO: 17) |
| DF1.2 | HC | GGTFNNNVAIN (SEQ ID NOs: 5 (whole), 6 and 7) | GIIPGLDTPNYAQKF QG (SEQ ID NOs: 8 and 9) | EMEVSGQWRPTEA FEI (SEQ ID NO: 24) |
| | LC | RASQTISNNFVA (SEQ ID NO: 15) | GASTRAT (SEQ ID NO: 16) | QQYGSSPYT (SEQ ID NO: 17) |
| DF2 | HC | GGTFNNNVAIN (SEQ ID NOs: 5 (whole), 6 and 7) | GIIPGLDTPNYAQKF QG (SEQ ID NOs: 8 and 9) | EVEVSGRWRPTEAF EI (SEQ ID NO: 54) |
| | LC | RASQTISNNFVA (SEQ ID NO: 15) | GASTRAT (SEQ ID NO: 16) | QQYGSSPYT (SEQ ID NO: 17) |
| DF3 | HC | GGTFNNNVAIN (SEQ ID NOs: 5 (whole), 6 and 7) | GIIPGLDTPNYAQKF QG (SEQ ID NOs: 8 and 9) | ELEVSGRWRPTEAF EI (SEQ ID NO: 55) |
| | LC | RASQTISNNFVA (SEQ ID NO: 15) | GASTRAT (SEQ ID NO: 16) | QQYGSSPYT (SEQ ID NO: 17) |
| DF4 | HC | GGTFNNNVAIN (SEQ ID NOs: 5 (whole), 6 and 7) | GIIPGLDTPNYAQKF QG (SEQ ID NOs: 8 and 9) | EREVSGRWRPTEAF EI (SEQ ID NO: 56) |
| | LC | RASQTISNNFVA (SEQ ID NO: 15) | GASTRAT (SEQ ID NO: 16) | QQYGSSPYT (SEQ ID NO: 17) |
| DF5 | HC | GGTFNNNVAIN (SEQ ID NOs: 5 (whole), 6 and 7) | GIIPGLDTPNYAQKF QG (SEQ ID NOs: 8 and 9) | EHEVSGRWRPTEAF EI (SEQ ID NO: 57) |
| | LC | RASQTISNNFVA (SEQ ID NO: 15) | GASTRAT (SEQ ID NO: 16) | QQYGSSPYT (SEQ ID NO: 17) |

TABLE 2 -continued

Alpha-toxin antagonist antibodies and antigen-binding CDR
sequences according to Kabat (underlined) and Chothia (bold)

| MAb | | CDR1 | CDR2 | CDR3 |
|---|---|---|---|---|
| DF6 | HC | GGTFNNVAIN (SEQ ID NOs: 5 (whole), 6 and 7) | GIIPGLDTPNYAQKFQG (SEQ ID NOs: 8 and 9) | EYEVSGRWRPTEAF EI (SEQ ID NO: 58) |
| | LC | RASQTISNNFVA (SEQ ID NO: 15) | GASTRAT (SEQ ID NO: 16) | QQYGSSPYT (SEQ ID NO: 17) |
| DF7 | HC | GGTFNNVAIN (SEQ ID NOs: 5 (whole), 6 and 7) | GIIPGLDTPNYAQKFQG (SEQ ID NOs: 8 and 9) | EAEVSGRWRPTEAF EI (SEQ ID NO: 59) |
| | LC | RASQTISNNFVA (SEQ ID NO: 15) | GASTRAT (SEQ ID NO: 16) | QQYGSSPYT (SEQ ID NO: 17) |
| DF8 | HC | GGTFNNVAIN (SEQ ID NOs: 5 (whole), 6 and 7) | GIIPGLDTPNYAQKFQG (SEQ ID NOs: 8 and 9) | ECEVSGRWRPTEAF EI (SEQ ID NO: 60) |
| | LC | RASQTISNNFVA (SEQ ID NO: 15) | GASTRAT (SEQ ID NO: 16) | QQYGSSPYT (SEQ ID NO: 17) |
| DF9 | HC | GGTFNNVAIN (SEQ ID NOs: 5 (whole), 6 and 7) | GIIPGLDTPNYAQKFQG (SEQ ID NOs: 8 and 9) | EDEVSGRWRPTEAF EI (SEQ ID NO: 61) |
| | LC | RASQTISNNFVA (SEQ ID NO: 15) | GASTRAT (SEQ ID NO: 16) | QQYGSSPYT (SEQ ID NO: 17) |
| DF10 | HC | GGTFNNVAIN (SEQ ID NOs: 5 (whole), 6 and 7) | GIIPGLDTPNYAQKFQG (SEQ ID NOs: 8 and 9) | EEEVSGRWRPTEAF EI (SEQ ID NO: 62) |
| | LC | RASQTISNNFVA (SEQ ID NO: 15) | GASTRAT (SEQ ID NO: 16) | QQYGSSPYT (SEQ ID NO: 17) |
| DF11 | HC | GGTFNNVAIN (SEQ ID NOs: 5 (whole), 6 and 7) | GIIPGLDTPNYAQKFQG (SEQ ID NOs: 8 and 9) | EFEVSGRWRPTEAF EI (SEQ ID NO: 63) |
| | LC | RASQTISNNFVA (SEQ ID NO: 15) | GASTRAT (SEQ ID NO: 16) | QQYGSSPYT (SEQ ID NO: 17) |
| DF12 | HC | GGTFNNVAIN (SEQ ID NOs: 5 (whole), 6 and 7) | GIIPGLDTPNYAQKFQG (SEQ ID NOs: 8 and 9) | EGEVSGRWRPTEAF EI (SEQ ID NO: 64) |
| | LC | RASQTISNNFVA (SEQ ID NO: 15) | GASTRAT (SEQ ID NO: 16) | QQYGSSPYT (SEQ ID NO: 17) |
| DF13 | HC | GGTFNNVAIN (SEQ ID NOs: 5 (whole), 6 and 7) | GIIPGLDTPNYAQKFQG (SEQ ID NOs: 8 and 9) | EIEVSGRWRPTEAF EI (SEQ ID NO: 65) |
| | LC | RASQTISNNFVA (SEQ ID NO: 15) | GASTRAT (SEQ ID NO: 16) | QQYGSSPYT (SEQ ID NO: 17) |
| DF14 | HC | GGTFNNVAIN (SEQ ID NOs: 5 (whole), 6 and 7) | GIIPGLDTPNYAQKFQG (SEQ ID NOs: 8 and 9) | EKEVSGRWRPTEAF EI (SEQ ID NO: 66) |
| | LC | RASQTISNNFVA (SEQ ID NO: 15) | GASTRAT (SEQ ID NO: 16) | QQYGSSPYT (SEQ ID NO: 17) |
| DF15 | HC | GGTFNNVAIN (SEQ ID NOs: 5 (whole), 6 and 7) | GIIPGLDTPNYAQKFQG (SEQ ID NOs: 8 and 9) | ENEVSGRWRPTEAF EI (SEQ ID NO: 67) |
| | LC | RASQTISNNFVA (SEQ ID NO: 15) | GASTRAT (SEQ ID NO: 16) | QQYGSSPYT (SEQ ID NO: 17) |
| DF16 | HC | GGTFNNVAIN (SEQ ID NOs: 5 (whole), 6 and 7) | GIIPGLDTPNYAQKFQG (SEQ ID NOs: 8 and 9) | EPEVSGRWRPTEAF EI (SEQ ID NO: 68) |
| | LC | RASQTISNNFVA (SEQ ID NO: 15) | GASTRAT (SEQ ID NO: 16) | QQYGSSPYT (SEQ ID NO: 17) |
| DF17 | HC | GGTFNNVAIN (SEQ ID NOs: 5 (whole), 6 and 7) | GIIPGLDTPNYAQKFQG (SEQ ID NOs: 8 and 9) | EQEVSGRWRPTEAF EI (SEQ ID NO: 69) |
| | LC | RASQTISNNFVA (SEQ ID NO: 15) | GASTRAT (SEQ ID NO: 16) | QQYGSSPYT (SEQ ID NO: 17) |

TABLE 2 -continued

Alpha-toxin antagonist antibodies and antigen-binding CDR
sequences according to Kabat (underlined) and Chothia (bold)

| MAb | | CDR1 | CDR2 | CDR3 |
|---|---|---|---|---|
| DF18 | HC | GGTFNNVAIN (SEQ ID NOs: 5 (whole), 6 and 7) | GIIPGLDTPNYAQKF QG (SEQ ID NOs: 8 and 9) | ESEVSGRWRPTEAF EI (SEQ ID NO: 34) |
| | LC | RASQTISNNFVA (SEQ ID NO: 15) | GASTRAT (SEQ ID NO: 16) | QQYGSSPYT (SEQ ID NO: 17) |
| DF19 | HC | GGTFNNVAIN (SEQ ID NOs: 5 (whole), 6 and 7) | GIIPGLDTPNYAQKF QG (SEQ ID NOs: 8 and 9) | ETEVSGRWRPTEAF EI (SEQ ID NO: 12) |
| | LC | RASQTISNNFVA (SEQ ID NO: 15) | GASTRAT (SEQ ID NO: 16) | QQYGSSPYT (SEQ ID NO: 17) |
| DF20 | HC | GGTFNNVAIN (SEQ ID NOs: 5 (whole), 6 and 7) | GIIPGLDTPNYAQKF QG (SEQ ID NOs: 8 and 9) | EWEVSGRWRPTEA FEI (SEQ ID NO: 11) |
| | LC | RASQTISNNFVA (SEQ ID NO: 15) | GASTRAT (SEQ ID NO: 16) | QQYGSSPYT (SEQ ID NO: 17) |

The invention also provides methods of generating, selecting, and making alpha-toxin antagonist antibodies. The antibodies of this invention can be made by procedures known in the art. In some embodiments, antibodies may be made recombinantly and expressed using any method known in the art.

In some embodiments, antibodies may be prepared and selected by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S, and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from human donors can be constructed and antibodies to a diverse array of antigens (including self-antigens) can be isolated essentially following the techniques described by Mark et al., J. Mol. Biol. 222: 581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

In some embodiments, antibodies may be made using hybridoma technology. It is contemplated that any mammalian subject including humans or antibody producing cells therefrom can be manipulated to serve as the basis for production of mammalian, including human, hybridoma cell lines. The route and schedule of immunization of the host animal are generally in keeping with established and conventional techniques for antibody stimulation and production, as further described herein. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., 1975, Nature 256:495-497 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the alpha-toxin monoclonal antibodies of the subject invention. The hybridomas or other immortalized B-cells are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for alpha-toxin, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with an alpha-toxin polypeptide, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the alpha-toxin antagonist antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329, 112; U.S. Pat. No. 7,314,622.

In some embodiments, the polynucleotide sequence may be used for genetic manipulation to "humanize" the antibody or to improve the affinity, or other characteristics of the antibody. Antibodies may also be customized for use, for example, in dogs, cats, primate, equines and bovines.

In some embodiments, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., domain, single chain, etc. are known in the art.

Immunoassays and flow cytometry sorting techniques such as fluorescence activated cell sorting (FACS) can also be employed to isolate antibodies that are specific for alpha-toxin.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of an alpha-toxin monoclonal antibody herein.

Antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In some embodiments, a polynucleotide comprises a sequence encoding the heavy chain and/or the light chain variable regions of antibody DF1.1, DF1, DF2, DF3, DF4, DF5, DF6, DF7, DFB, DF9, DF10, DF11, DF12, DF13, DF14, DF15, DF16, DF17, DF18, DF19 or DF20. The sequence encoding the antibody of interest may be maintained in a vector in a host cell and the host cell can then be expanded and frozen for future use. Vectors (including expression vectors) and host cells are further described herein.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and PCT Publication No. WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using, for example, Biacore™ surface plasmon resonance analysis, which detects differences in binding affinity of about 2-fold or greater, Kinexa® Biosensor, scintillation proximity assays, ELISA, ORIGEN® immunoassay, fluorescence quenching, fluorescence transfer, and/or yeast display. Binding affinity may also be screened using a suitable bioassay. Biacore™ is particularly useful when the starting antibody already binds with a relatively high affinity, for example a $K_D$ of about 10 nM or lower.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., 1993, Gene 137(1):109-18.

The CDR may be heavy chain variable region (VH) CDR3 and/or light chain variable region (VL) CDR3. The CDR may be one or more of VH CDR1, VH CDR2, VH CDR3, VL CDR1, VL CDR2, and/or VL CDR3. The CDR may be a Kabat CDR, a Chothia CDR, an extended CDR, an AbM CDR, a contact CDR, or a conformational CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Kinexa™ biosensor analysis, and selection using any method known in the art for selection, including phage display, yeast display, and ribosome display.

To express the alpha-toxin antibodies of the present invention, DNA fragments encoding VH and VL regions can first be obtained using any of the methods described above. Various modifications, e.g. mutations, deletions, and/or additions can also be introduced into the DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

The invention encompasses modifications to the variable regions shown in Table 1 and the CDRs shown in Table 2. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to alpha-toxin. Examples of variants of the CDRs shown in Table 2 are described in Example 2 below. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 3 under the heading of "conservative substitutions." If such substitutions result in a change in biological activity, then more substantial changes, denominated "exemplary substitutions" in Table 3, or as further described below in reference to amino acid classes, may be introduced and the products screened.

TABLE 3

Amino Acid Substitutions

| Original Residue | Conservative Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:
  (1) Non-polar: Norleucine, Met, Ala, Val, Leu, Ile;
  (2) Polar without charge: Cys, Ser, Thr, Asn, Gln;
  (3) Acidic (negatively charged): Asp, Glu;
  (4) Basic (positively charged): Lys, Arg;
  (5) Residues that influence chain orientation: Gly, Pro; and
  (6) Aromatic: Trp, Tyr, Phe, His.
Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for alpha-toxin, to increase or decrease $k_{off}$, or to alter the binding specificity of the antibody. Techniques in site-directed mutagenesis are well-known in the art. See, e.g., Sambrook et al. and Ausubel et al., supra.

In some embodiments the VH comprises the amino acid sequence of SEQ ID NO: 35 or a variant thereof with one or several (e.g., 2, 3, 4, 5, 6, 7, 8, 9, 10, 11 or 12) conservative amino acid substitutions in residues that are not within a CDR. In some embodiments the VL comprises the amino acid sequence of SEQ ID NO: 3 or a variant thereof with one or several amino acid substitutions in amino acids that are not within a CDR.

A modification or mutation may also be made in a framework region or constant region to increase the half-life of an alpha-toxin antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides are made using established procedures in the art and can be screened using standard assays known in the art, some of which are described below and in the Examples.

In some embodiments, the antibody comprises a modified constant region that has increased or decreased binding affinity to a human Fc gamma receptor, is immunologically inert or partially inert, e.g., does not trigger complement mediated lysis, does not stimulate antibody-dependent cell mediated cytotoxicity (ADCC), or does not activate microglia; or has reduced activities (compared to the unmodified antibody) in any one or more of the following: triggering complement mediated lysis, stimulating ADCC, or activating microglia. Different modifications of the constant region may be used to achieve optimal level and/or combination of effector functions. See, for example, Morgan et al., Immunology 86:319-324, 1995; Lund et al., J. Immunology 157:4963-9 157:4963-4969, 1996; Idusogie et al., J. Immunology 164:4178-4184, 2000; Tao et al., J. Immunology 143: 2595-2601, 1989; and Jefferis et al., Immunological Reviews 163:59-76, 1998. In some embodiments, the constant region is modified as described in Eur. J. Immunol., 1999, 29:2613-2624; PCT Application No. PCT/GB99/01441; and/or UK Patent Application No. 9809951.8.

In some embodiments, an antibody constant region can be modified to avoid interaction with Fc gamma receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In some embodiments, the constant region is modified as described in Eur. J. Immunol., 1999, 29:2613-2624; PCT Application No. PCT/GB99/01441; and/or UK Patent Application No. 9809951.8. In such embodiments, the Fc can be human $IgG_2$ or human $IgG_4$. The Fc can be human $IgG_2$ containing the mutation A330P331 to S330S331 ($IgG_{2\Delta a}$), in which the amino acid residues are numbered with reference to the wild type $IgG_2$ sequence. Eur. J. Immunol., 1999, 29:2613-2624. In some embodiments, the antibody comprises a constant region of $IgG_4$ comprising the following mutations (Armour et al., 2003, Molecular Immunology 40 585-593): E233F234L235 to P233V234A235 ($IgG_{4\Delta c}$), in which the numbering is with reference to wild type IgG4. In yet another embodiment, the Fc is human $IgG_4$ E233F234L235 to P233V234A235 with deletion G236 ($IgG_{4\Delta b}$). In another embodiment the Fc is any human $IgG_4$ Fc ($IgG_4$, $IgG_{4\Delta b}$ or $IgG_{4\Delta c}$) containing hinge stabilizing mutation S228 to P228 (Aalberse et al., 2002, Immunology 105, 9-19).

In some embodiments, the antibody comprises a human heavy chain $IgG_2$ constant region comprising the following mutations: A330P331 to S330S331 (amino acid numbering with reference to the wild type $IgG_2$ sequence). Eur. J. Immunol., 1999, 29:2613-2624. In still other embodiments, the constant region is aglycosylated for N-linked glycosylation. In some embodiments, the constant region is aglycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143: 2595-2601, 1989; and Jefferis et al., Immunological Reviews 163:59-76, 1998. In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

In some embodiments, the antibody comprises a modified constant region that has increased binding affinity for FcRn and/or an increased serum half-life as compared with the unmodified antibody.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., 1992, J. Mol. Biol. 227:776-798; and Cox et al., 1994, Eur. J. Immunol. 24:827-836).

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an alpha-toxin antibody of the invention can be cleaved. In various embodiments of the invention, the heavy and light chains of the alpha-toxin antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but most preferably is an $IgG_1$ or $IgG_2$ constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. An example of a linking peptide is $(GGGGS)_3$ (SEQ ID NO: 18), which bridges approximately 3.5 nm between the carboxy terminus of one variable region and the amino terminus of the other variable region. Linkers of other sequences have been designed and used (Bird et al., 1988, supra). Linkers can in turn be modified for additional functions, such as attachment of drugs or attachment to solid supports. The single chain antibody may be monovalent, if only a single VH and VL are used, bivalent, if two VH and VL are used, or polyvalent, if more than two VH and VL are used. Bispecific or polyvalent antibodies may be generated that bind specifically to alpha-toxin and to another molecule. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies, are also encompassed. Diabodies are bivalent, bispecific antibodies in which VH and VL are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. USA 90:6444-6448; Poljak, R. J., et al., 1994, Structure 2:1121-1123).

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

The invention also encompasses fusion proteins comprising one or more fragments or regions from the antibodies disclosed herein. In some embodiments, a fusion antibody may be made that comprises all or a portion of an alpha-toxin antibody of the invention linked to another polypeptide. In another embodiment, only the variable domains of the alpha-toxin antibody are linked to the polypeptide. In another embodiment, the VH domain of an alpha-toxin antibody is linked to a first polypeptide, while the VL domain of an alpha-toxin antibody is linked to a second polypeptide that associates with the first polypeptide in a manner such that the VH and VL domains can interact with one another to form an antigen binding site. In another preferred embodiment, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

In some embodiments, a fusion polypeptide is provided that comprises at least 10 contiguous amino acids of the variable light chain region shown in SEQ ID NOs: 1 or 3 and/or at least 10 amino acids of the variable heavy chain region shown in SEQ ID NOs: 2 or 4. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, as shown in any of the sequence pairs selected from among SEQ ID NOs: 1 and 2, and 3 and 4. In another embodiment, the fusion polypeptide comprises one or more CDR(s). In still other embodiments, the fusion polypeptide comprises VH CDR3 and/or VL CDR3. For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6H is tag. Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

In other embodiments, other modified antibodies may be prepared using alpha-toxin antibody encoding nucleic acid molecules. For instance, "Kappa bodies" (Ill et al., 1997, Protein Eng. 10:949-57), "Minibodies" (Martin et al., 1994, EMBO J. 13:5303-9), "Diabodies" (Holliger et al., supra), or "Janusins" (Traunecker et al., 1991, EMBO J. 10:3655-3659 and Traunecker et al., 1992, Int. J. Cancer (Suppl.) 7:51-52) may be prepared using standard molecular biological techniques following the teachings of the specification.

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). For example, bispecific antibodies or antigen-binding fragments can be produced by fusion of hybridomas or linking of Fab' fragments. See, e.g., Songsivilai & Lachmann, 1990, Clin. Exp. Immunol. 79:315-321, Kostelny et al., 1992, J. Immunol. 148:1547-1553. Traditionally, the recombinant production of bispecific antibodies was based on the coexpression of two immunoglobulin heavy chain-light chain pairs, with the two heavy chains having different specificities (Millstein and Cuello, 1983, Nature 305, 537-539). In addition, bispecific antibodies may be formed as "diabodies" or "Janusins." In some embodiments, the bispecific antibody binds to two different epitopes of alpha-toxin. In some embodiments, the modified antibodies described above are prepared using one or more of the variable domains or CDR regions from an alpha-toxin antibody provided herein.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the alpha-toxin binding and/or antagonist embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the lung, heart, or heart valve.

An antibody or polypeptide of this invention may be linked to a labeling agent such as a fluorescent molecule, a radioactive molecule or any others labels known in the art. Labels are known in the art which generally provide (either directly or indirectly) a signal.

Polynucleotides, Vectors, and Host Cells

The invention also provides polynucleotides encoding any of the antibodies, including antibody fragments and modified antibodies described herein, such as, e.g., antibodies having impaired effector function. In another aspect, the invention provides a method of making any of the polynucleotides described herein. Polynucleotides can be made and expressed by procedures known in the art. Accordingly, the invention provides polynucleotides or compositions, including pharmaceutical compositions, comprising polynucleotides, encoding any of the following: the antibodies DF1.1, DF1, DF2, DF3, DF4, DF5, DF6, DF7, DF8, DF9, DF10, DF11, DF12, DF13, DF14, DF15, DF16, DF17, DF18, DF19 or DF20, or any fragment or part thereof having the ability to antagonize alpha-toxin.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a fragment thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a fragment thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors are further provided. Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as E. coli or B. subtillis) and yeast (such as S. cerevisae, S. pombe; or K. lactis). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to alpha-toxin or an alpha-toxin domain is effected by an immunoassay or FACS. A cell overexpressing the antibody or protein of interest can be identified.

An expression vector can be used to direct expression of an alpha-toxin antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:

338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell. Biol., 1994, 14:2411, and in Woffendin, Proc. Natl. Acad. Sci., 1994, 91:1581.

Compositions

The invention also provides pharmaceutical compositions comprising an effective amount of an alpha-toxin antibody described herein. Examples of such compositions, as well as how to formulate, are also described herein. In some embodiments, the composition comprises one or more alpha-toxin antibodies. In other embodiments, the alpha-toxin antibody recognizes alpha-toxin. In other embodiments, the alpha-toxin antibody is a human antibody. In other embodiments, the alpha-toxin antibody is a humanized antibody. In some embodiments, the alpha-toxin antibody comprises a constant region that is capable of triggering a desired immune response, such as antibody-mediated lysis or ADCC. In other embodiments, the alpha-toxin antibody comprises a constant region that does not trigger an unwanted or undesirable immune response, such as antibody-mediated lysis or ADCC. In other embodiments, the alpha-toxin antibody comprises one or more CDR(s) of the antibody (such as one, two, three, four, five, or, in some embodiments, all six CDRs).

It is understood that the compositions can comprise more than one alpha-toxin antibody (e.g., a mixture of alpha-toxin antibodies that recognize different epitopes of alpha-toxin). Other exemplary compositions comprise more than one alpha-toxin antibody that recognize the same epitope(s), or different species of alpha-toxin antibodies that bind to different epitopes of alpha-toxin. In some embodiments, the compositions comprise a mixture of alpha-toxin antibodies that recognize different variants of alpha-toxin.

The composition used in the present invention can further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The alpha-toxin antibody and compositions thereof can also be used in conjunction with other agents that serve to enhance and/or complement the effectiveness of the agents.

The invention also provides compositions, including pharmaceutical compositions, comprising any of the polynucleotides of the invention. In some embodiments, the composition comprises an expression vector comprising a polynucleotide encoding the antibody as described herein. In other embodiment, the composition comprises an expression vector comprising a polynucleotide encoding any of the antibodies described herein. In still other embodiments, the composition comprises either or both of the polynucleotides shown in SEQ ID NO: 13 and SEQ ID NO: 14 below, or either or both of the polynucleotides shown in SEQ ID NO: 19 and SEQ ID NO: 20 below:

```
DF1 heavy chain variable region
                                           (SEQ ID NO: 13)
CAGGTGCAGCTGGTTCAGAGTGGCGCCGAGGTTAAGAAGCCGGGATCGT

CCGTGAAGGTGTCCTGTAAGGCATCAGGCGGGACTTTCAACAATGTGGC

AATTAATTGGGTTAGACAGGCCCCAGGGCAGGGGCTGGAATGGATGGGC

GGCATTATTCCCGGACTTGATACCCCAAATTACGCCCAGAAGTTTCAGG

GCCGCGTGACCATAACCGCCGACGAATCTACTAGCACTGCATACATGGA
```

```
GCTTAGCAGTCTGCGGAGCGAGGACACCGCCGTGTATTACTGCGCCAGG

GAGATGGAGGTGAGCGGCAGGTGGAGGCCTACCGAAGCCTTCGAAATCT

GGGGCCAGGGCACCCTGGTCACCGTCTCTTCA
```

DF1 light chain variable region
(SEQ ID NO: 14)
```
GAAATAGTGCTAACACAATCCCCTGGCACCCTGAGCCTGAGTCCCGGCG

AACGGGCTACTCTGAGCTGCAGAGCAAGTCAGACAATAAGCAACAACTT

TGTCGCGTGGTACCAGCAGAAGCCTGGCCAGGCACCCCGGCTGCTCATC

TATGGAGCCTCCACCCGGGCCACTGGCATACCAGACAGATTCTCTGAA

GCGGGAGTGGCACGGACTTCACCCTGACGATCAGTAGGCTCGAGCCCGA

AGATTTTGCAGTGTACTACTGCCAACAGTATGGCAGTAGCCCCTACACA

TTCGGTCAGGGGACCAAGCTTGAGATTAAA
```

DF1.1 heavy chain variable region
(SEQ ID NO: 19)
```
CAGGTGCAGCTGGTGCAATCTGGGGCTGAGGTGAAGAAGCCTGGGTCCT

CGGTGAAAGTCTCCTGCAAGACTTCTGGAGGCACCTTCAACAATGTTGC

TATCAACTGGGTGCGCCAAGCCCCTGGACAAGGGCTTGAGTGGATGGGA

GGGATCATCCCTGGCCTTGACACACCAAACTACGCACAGAAGTTCCAGG

GCAGAGTCACTATTACCGCGGACAAATCCACGACTTCGACCTACTTGGA

GTTGAGTAGCCTGAGATCTGACGACACGGCCGTGTATTACTGTAGGCGA

GAGATGGAAGTCAGTGGGCGGTGGCGGCCGACAGAAGCTTTTGAAATCT

GGGGCCAAGGGACAATGGTCACCGTCTCCTCA
```

DF1.1 light chain variable region
(SEQ ID NO: 20)
```
GAAACGACACTCACGCAGTCTCCAGGCACCCTGTCTTTGTCTCCAGGGG

AAAGAGCCACCCTCTCCTGCAGGGCCAGTCAGACTATTAGCAACAACTT

TGTAGCCTGGTATCAGCAGAAACCTGGCCAGGCTCCCAGGCTCCTCATC

TATGGTGCATCCACCAGGGCCACTGGCATCCCAGACAGGTTCAGTGGCA

GTGGGTCTGGGACAGACTTCACTCTCACCATCAGCAGCCTAGAGCCTGA

AGATTTTGCAGTGTATTACTGTGCCCAGTATGGTAGCTCACCGTACACT

TTTGGCCAGGGGACCAAAGTGGATATCAAA
```

Kits

The invention also provides kits comprising any or all of the antibodies described herein. Kits of the invention include one or more containers comprising an alpha-toxin antagonist antibody described herein and instructions for use in accordance with any of the methods of the invention described herein. Generally, these instructions comprise a description of administration of the alpha-toxin antagonist antibody for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In some embodiments, the antibody is a human antibody. In some embodiments, the antibody is a humanized antibody. In some embodiments, the antibody is a monoclonal antibody. The instructions relating to the use of an alpha-toxin antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an alpha-toxin antibody. The container may further comprise a second pharmaceutically active agent.

Kits may optionally provide additional components such as buffers and interpretive information. Normally, the kit comprises a container and a label or package insert(s) on or associated with the container.

The invention also provides diagonistic kits comprising any or all of the antibodies described herein. The diagonistic kits are useful for, for example, detecting the presence of alpha-toxin in a sample. In some embodiments, a diagnostic kit can be used to identify an individual with a latent S. aureus infection that may put them at risk of developing an invasive form of infection. In some embodiments, a diagonistic kit can be used to determine whether an individual is at risk for a staphylococcal disease. In some embodiments, a diagnostic kit can be use to detect the presence of alpha-toxin in an individual suspected of having a staphylococcal disease.

Diagnostic kits of the invention include one or more containers comprising an alpha-toxin antagonist antibody described herein and instructions for use in accordance with any of the methods of the invention described herein. Generally, these instructions comprise a description of use of the alpha-toxin antagonist to detect the presence of alpha-toxin in individuals at risk for, or suspected of having, staphylococcal disease. In some embodiments, an exemplary diagonistic kit can be configured to contain reagents such as, for example, an alpha-toxin antagonist antibody, a negative control sample, a positive control sample, and directions for using the kit.

Biological Deposit

Representative materials of the present invention were deposited in the American Type Culture Collection, 10801 University Boulevard, Manassas, Va. 20110-2209, USA, on Jun. 15, 2012. Vector DF2-VH having ATCC Accession No. PTA-12982 is a polynucleotide encoding the DF2 heavy chain variable region, and vector DF2-VL having ATCC Accession No. PTA-12983 is a polynucleotide encoding the DF2 light chain variable region. The deposits were made under the provisions of the Budapest Treaty on the International Recognition of the Deposit of Microorganisms for the Purpose of Patent Procedure and Regulations thereunder (Budapest Treaty). This assures maintenance of a viable curlture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 8860G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Generating and Screening Alpha-Toxin Antibodies

This example illustrates the generation and screening of alpha-toxin antibodies.

An scFv phage library built from the complete germline diversity of 654 human donor IgM repertoires with an estimated $3.1 \times 10^{10}$ diversity (Glanville et al. 2009) was used as a source from which to select antibodies that specifically bind alpha-toxin from *S. aureus*. Purified alpha-toxin from *S. aureus* (Calbiochem®) was biotinylated using EZ-link® sulfo-NHS-LC-LC-biotin (Pierce) resulting in a biotinylation ratio of approximately 3.4 moles of biotin per mole of alpha-toxin. The scFv phage library was first depleted to remove binders to streptavidin magnetic beads and then incubated with biotinylated alpha-toxin at 500 nM for 1 hr at RT in the presence of 0.5% BSA. Streptavidin magnetic beads were added to capture the alpha-toxin/phage particles and incubated at RT for 30 minutes. The magnetic beads were then washed sequentially with 0.1% Tween®20/PBS, 0.5% BSA/PBS and PBS to wash away unbound phage. After the washes, an enzymatic elution step was performed with trypsin (50 mg/ml trypsin, 5 minutes incubation at 37° C.). The eluted phage was used to infect 10 ml of exponentially growing *E. coli* TG1 cells. Infected cells were grown at 37° C. without shaking for 1 hour, spun down and resuspended in 500 µL of 2YT/2% glucose/carbenicillin, plated on two 15 cm diameter plates (2YT/glucose/carbenicillin) and incubated overnight at 30° C. Colonies were scraped off in 10 ml 2YT/glucose/carbenicillin and glycerol was added to a final concentration of 15% for storage at −70° C. Glycerol stock cultures from the first round of panning selection were superinfected with helper phage and rescued to prepare scFv-expressing phage particles for the second round of panning. A total of three rounds of panning were carried out as described for the first round with the only exception that the concentration of biotinylated alpha-toxin was reduced to 250 nM.

A number of individual clones from the second and third panning were grown in 1.5 ml cultures in 2YT/glucose/carbenicillin for 6-7 hours at 37° C., switched to 2YT/carbenicillin and induced to produce scFv by addition of 0.5 mM IPTG and incubation overnight at 30° C. Crude scFv-containing culture supernatants prepared by three cycles of freeze-thawing and filtration were screened for their ability to bind alpha-toxin by ELISA and block the lytic activity of the toxin on rabbit erythrocytes. *S. aureus* alpha-toxin lyses rabbit erythrocytes with an $EC_{50}$ in the low nM range, releasing hemoglobin that can be measured by absorbance at 405 nm. Inhibition of alpha-toxin lytic activity by the presence of specific scFvs is therefore correlated to a decrease of released hemoglobin. Purified scFv from positive clones were identified, retested and ranked by ELISA, rabbit erythrocytes lysis assay and sequenced leading to the selection of a clone that was converted to a full IgG format for further in vitro and in vivo testing, this mAb was named DF1.1. A germlined version of DF1.1 was generated and named DF1.

The amino acid sequence of alpha-toxin antibody DF1 full-length heavy chain (SEQ ID NO: 21) is shown below:

(SEQ ID NO: 21)
QVQLVQSGAEVKKPGSSVKVSCKASGGTFNNVAINWVRQAPGQGLEWMG

GIIPGLDTPNYAQKFQGRVTITADESTSTAYMELSSLRSEDTAVYYCAR

EMEVSGRWRPTEAFEIWGQGTLVTVSSASTKGPSVFPLAPCSRSTSEST

AALGCLVKDYFPEPVTVSWNSGALTSGVHTFPAVLQSSGLYSLSSVVTV

PSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTK

PREEQFNSTFRVVSVLTVVHQDWLNGKEYKCKVSNKGLPSSIEKTISKT

KGQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHYT

QKSLSLSPGK

The amino acid sequence of alpha-toxin antibody DF1 full-length heavy chain without the C-terminal lysine (SEQ ID NO: 22) is shown below:

(SEQ ID NO: 22)
QVQLVQSGAEVKKPGSSVKVSCKASGGTFNNVAINWVRQAPGQGLEWMG

GIIPGLDTPNYAQKFQGRVTITADESTSTAYMELSSLRSEDTAVYYCAR

EMEVSGRWRPTEAFEIWGQGTLVTVSSASTKGPSVFPLAPCSRSTSEST

AALGCLVKDYFPEPVTVSWNSGALTSGVHTFPAVLQSSGLYSLSSVVTV

PSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTK

PREEQFNSTFRVVSVLTVVHQDWLNGKEYKCKVSNKGLPSSIEKTISKT

KGQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHYT

QKSLSLSPG

The amino acid sequence of alpha-toxin antibody DF1 and DF2 full-length light chain (SEQ ID NO: 23) is shown below:

(SEQ ID NO: 23)
EIVLTQSPGTLSLSPGERATLSCRASQTISNNFVAWYQQKPGQAPRLLI

YGASTRATGIPDRFSGSGSGTDFTLTISRLEPEDFAVYYCQQYGSSPYT

FGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC

The amino acid sequence of alpha-toxin antibody DF2 full-length heavy chain (SEQ ID NO: 72) is shown below:

(SEQ ID NO: 72)
QVQLVQSGAEVKKPGSSVKVSCKASGGTFNNVAINWVRQAPGQGLEWMG

GIIPGLDTPNYAQKFQGRVTITADESTSTAYMELSSLRSEDTAVYYCAR

EVEVSGRWRPTEAFEIWGQGTLVTVSSASTKGPSVFPLAPCSRSTSEST

AALGCLVKDYFPEPVTVSWNSGALTSGVHTFPAVLQSSGLYSLSSVVTV

PSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTK

PREEQFNSTFRVVSVLTVVHQDWLNGKEYKCKVSNKGLPSSIEKTISKT

KGQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHYT

QKSLSLSPGK

The amino acid sequence of alpha-toxin antibody DF2 full-length heavy chain without the C-terminal lysine (SEQ ID NO: 73) is shown below:

(SEQ ID NO: 73)
QVQLVQSGAEVKKPGSSVKVSCKASGGTFNNVAINWVRQAPGQGLEWMG

GIIPGLDTPNYAQKFQGRVTITADESTSTAYMELSSLRSEDTAVYYCAR

EVEVSGRWRPTEAFEIWGQGTLVTVSSASTKGPSVFPLAPCSRSTSEST

AALGCLVKDYFPEPVTVSWNSGALTSGVHTFPAVLQSSGLYSLSSVVTV

PSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTK

PREEQFNSTFRVVSVLTVVHQDWLNGKEYKCKVSNKGLPSSIEKTISKT

KGQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHYT

QKSLSLSPG

Example 2

Sequence Analysis of Alpha-Toxin Antibodies

This example illustrates the analysis of deep sequencing results of the anti-alpha-toxin clones obtained from the panning experiment described in Example 1 above.

TITANIUM™ Roche 454 high-throughput sequencing was used to obtain 83,316 sequences from clones selected during the 2nd and 3rd rounds of panning. Of the sequences observed, a total of 192 distinct clonal variants of DF1.1 VH were observed to be present in the library and enriched during panning. Sequences were confirmed by a minimum of 2-fold sequencing depth, a common V-gene and J-gene, and a maximum CDR-H3 single linkage amino acid Hamming distance of 2 from a confirmed binder (as defined in Glanville et al. PNAS 2011). The sequencing data are represented in Position Frequency Matrices (PFMs), shown in FIGS. 1-5. See, Stormo et al., Nucleic Acids Res, 1982, 10:2997-3012. The PFMs based on the CDR sequences of the clonal variants of DF1.1 can be used to reliably predict additional binding variants. See, e.g., Stormo et al., Bioinformatics, 2000, 16(1):16-23.

Table A in FIG. 1 shows the amino acid frequency for each position in VH CDR3 based on deep sequencing of the positive clones obtained from the anti-alpha-toxin panning described in Example 1. Row 1 of Table A indicates the position in VH CDR3 based on Kabat numbering (positions 95-102). The row labeled "CDR pos" indicates the relative position within VH CDR3 (position 1-16). The row labeled "DF1" shows the amino acid at each position of VH CDR3 of alpha-toxin antagonist antibody DF1, which is included for reference. The next 20 rows indicate the % frequency of each amino acid for each of the positions in VH CDR3. For example, at position 95, an aspartic acid (D) was found in 5.4% of the clones, a glutamic acid (E) was found in 89.1% of the clones, and a glycine (G) was found in 5.4% of the clones. None of the clones had an alanine (A), cysteine (C), phenylalanine (F), histidine (H), isoleucine (I), lysine (K), leucine (L), methionine (M), asparagine (N), proline (P), glutamine (Q), arginine (R), serine (S), threonine (T), valine (V), tryptophan (W), or tyrosine (Y) at position 95.

The sequencing analysis demonstrates that the alpha-toxin antibody VH CDR3 sequence having the most frequently occurring amino acids is EMEVSGQWRPTEAFEI (SEQ ID NO: 24) or EMEVSGRWRPTEAFEI (SEQ ID NO: 10). The analysis further demonstrates that alpha-toxin antagonist antibodies include antibodies comprising the VH CDR3 sequence of EMEVSGRWRPTEAFEI (SEQ ID NO: 10) and variants thereof (SEQ ID NO: 25) wherein the amino acid at position 1 is D, E or G; the amino acid at position 2 is H, L, M, R, V or Y; the amino acid at position 3 is E, G, L or Y; the amino acid at position 4 is A, E, G, V or Y; the amino acid at position 5 is A, I, N, R, S, T or Y; the amino acid at position 6 is G, R, S or Y; the amino acid at position 7 is D, G, Q or R; the amino acid at position 8 is C, D, G, N, R, S, or W; the amino acid at position 9 is G, Q, R, S or Y; the amino acid at position 10 is G, L, P or R; the amino acid at position 11 is A, H, P, Q or T; the amino acid at position 12 is D, E, G, H, K, N or S; the amino acid at position 13 is A, L, P or V; the amino acid at position 14 is F or L; the amino acid at position 15 is D, E or S; and the amino acid at position 16 is F, I, L or V.

Deep sequencing revealed that the alpha-toxin antibodies identified by panning included antibodies comprising VL CDR3s of four different lengths, i.e., 8, 9, 10 or 11 amino acids in length. Tables B-E in FIGS. 2-5 show the amino acid frequency for each position in VL CDR3 based on deep sequencing of the positive clones obtained from the anti-alpha-toxin panning described in Example 1. Table B shows the sequencing analysis for VL CDR3 having 8 amino acids at positions 90, 91, 92, 93, 94, 95, 96 and 97 according to Kabat. Table C shows the sequencing analysis for VL CDR3 having 9 amino acids at positions 90, 91, 92, 93, 94, 95, 95A, 96 and 97 according to Kabat. Table D shows the sequencing analysis for VL CDR3 having 10 amino acids at positions 90, 91, 92, 93, 94, 95, 95A, 95B, 96 and 97 according to Kabat. Table E shows the sequencing analysis for VL CDR3 having 11 amino acids at positions 90, 91, 92, 93, 94, 95, 95A, 95B, 95C, 96 and 97 according to Kabat. The second row of each of Tables B-E, labeled "CDR pos" indicates the relative position with VL CDR3. The row labeled "Ref" shows the most frequently occurring amino acid at each position of VL CDR3. The next 20 rows indicate the % frequency of each amino acid for each of the positions in VL CDR3.

The sequencing analysis demonstrates that the alpha-toxin antibody VL CDR3 sequence 8 amino acids in length having the most frequently occurring amino acids is QQYGSSPT (SEQ ID NO: 26) (FIG. 2). The analysis further demonstrates that alpha-toxin antagonist antibodies include antibodies comprising the VL CDR3 sequence of QQYGSSPT (SEQ ID NO: 26) and variants thereof (SEQ ID NO: 27) wherein the amino acid at position 1 is H, L, M or Q; the amino acid at position 2 is E, H, K, L, Q or R; the amino acid at position 3 is A, F, G, R, S, T or Y; the amino acid at position 4 is A, D, E, G, H, L, N, S, T or Y; the amino acid at position 5 is A, D, F, H, I, N, Q, R, S, T or Y; the amino acid at position 6 is A, D, E, H, L, P, S, T, W or Y; the amino acid at position 7 is D, F, G, H, I, L, P, Q, R, S, V, W or Y; and the amino acid at position 8 is A, D, G, K, L, P, Q, S, T or V.

The sequencing analysis demonstrates that the alpha-toxin antibody VL CDR3 sequence 9 amino acids in length having the most frequently occurring amino acids is QQYGSSPLT (SEQ ID NO: 28) (FIG. 3). The analysis further demonstrates that alpha-toxin antagonist antibodies include antibodies comprising the VL CDR3 sequence of QQYGSSPLT (SEQ ID NO: 28) and variants thereof (SEQ ID NO: 29) wherein the amino acid at position 1 is E, H, L, M or Q; the amino acid at position 2 is E, H, N, Q, R or S; the amino acid at position 3 is A, C, D, F, G, H, L, P, R, S, T, V or Y; the amino acid at position 4 is A, D, E, F, G, H, I, K, L, M, N, R, S, T, V or Y; the amino acid at position 5 is A, D, E, F, G, H, I, K, L, M, N, Q, R, S, T, V, W or Y; the amino acid at position 6 is A, D, F, G, I, K, L, M, N, P, Q, S, T, V, W or Y; the amino acid at position 7 is A, D, E, F, G, H, I, L, M, N, P, Q, R, S, T or V; the amino acid at position 8 is A, E, F, G, H, I, K, L, M, N, P, Q, R, S, T, V, W or Y and the amino acid at position 9 is A, G, I, K, L, N, P, S, T or Y.

The sequencing analysis demonstrates that the alpha-toxin antibody VL CDR3 sequence 10 amino acids in length having the most frequently occurring amino acids is QQYGSSPPYT (SEQ ID NO: 30) (FIG. 4). The analysis further demonstrates that alpha-toxin antagonist antibodies include antibodies comprising the VL CDR3 sequence of QQYGSSPPYT (SEQ ID NO: 30) and variants thereof (SEQ ID NO: 31) wherein the amino acid at position 1 is H or Q; the amino acid at position 2 is H, Q or Y; the amino acid at position 3 is R, S or Y; the amino acid at position 4 is A, D, G, H, K, N, S or T; the amino acid at position 5 is A, D, E, G, N, R, S, T or Y; the amino acid at position 6 is A, R, S, T or W; the amino acid at position 7 is A, I, L, P, Q, S, T or V; and the amino acid at position 8 is E, G, L, P, Q, R, S or T; the amino acid at position 9 is D, F, G, I, L, N, R, T, V, W or Y; and the amino acid at position 10 is A, I, M, P, S, T or V.

The sequencing analysis demonstrates that the alpha-toxin antibody VL CDR3 sequence 11 amino acids in length having the most frequently occurring amino acids is QQYGSSPPGVT (SEQ ID NO: 32) (FIG. 5). The analysis further demonstrates that alpha-toxin antagonist antibodies include antibodies comprising the VL CDR3 sequence of QQYGSSPPGVT (SEQ ID NO: 32) and variants thereof (SEQ ID NO: 33) wherein the amino acid at position 1 is G, Q or S; the amino acid at position 2 is Q, S, T or V; the amino acid at position 3 is R, W or Y; the amino acid at position 4 is D, G, S or T; the amino acid at position 5 is G, N, S or T; the amino acid at position 6 is S or W; the amino acid at position 7 is G, L, P, S or T; and the amino acid at position 8 is D, L, P, R, S or T; the amino acid at position 9 is A, D, G, H, L, M, R or S; the amino acid at position 10 is F, I, L, V or Y; and the amino acid at position 11 is A, T or V.

To evaluate light chain partnering, 129,118 Roche TITANIUM™ 454 long reads spanning the heavy and light chains of the scFv library were obtained. The sequence data demonstrate that antibody DF1.1 is permissive of light chain content, with multiple V-kappa and V-lambda V-gene partners observed, with diverse CDR-L3 lengths and amino acid content. Of 39,622 DF1.1 heterodimers clones observed, 1,085 distinct light chains were found to be in association with DF1.1 heavy chains, including 23 V-kappa and 7 V-lambda segments, and four common CDR-L3 amino acid sequence lengths.

TABLE F

Alpha-toxin Antibody Heavy and Light Chain Gene Representation

| Heavy Chain | Light Chain | Counts | Frequency (%) |
|---|---|---|---|
| IGHV1-69 | IGKV3-20 | 17328 | 78.1% |
| IGHV1-69 | IGKV3-15 | 1879 | 8.5% |
| IGHV1-69 | IGKV1-39 | 976 | 4.4% |
| IGHV1-69 | IGKV3-11 | 364 | 1.6% |
| IGHV1-69 | IGKV2-28 | 289 | 1.3% |
| IGHV1-69 | IGKV1-12 | 242 | 1.1% |
| IGHV1-69 | IGKV1-9 | 157 | 0.7% |
| IGHV1-69 | IGKV4-1 | 148 | 0.7% |
| IGHV1-69 | IGKV3D-20 | 147 | 0.7% |
| IGHV1-69 | IGLV1-40 | 129 | 0.6% |
| IGHV1-69 | IGKV1-5 | 128 | 0.6% |
| IGHV1-69 | IGKV3-NL5 | 120 | 0.5% |
| IGHV1-69 | IGKV1-17 | 42 | 0.2% |
| IGHV1-69 | IGKV3-NL1 | 33 | 0.1% |
| IGHV1-69 | IGKV1-6 | 27 | 0.1% |
| IGHV1-69 | IGKV2-40 | 26 | 0.1% |
| IGHV1-69 | IGKV1-33 | 24 | 0.1% |
| IGHV1-69 | IGKV1-27 | 23 | 0.1% |
| IGHV1-69 | IGLV2-14 | 21 | 0.1% |
| IGHV1-69 | IGLV6-57 | 18 | 0.1% |
| IGHV1-69 | IGLV1-51 | 12 | 0.1% |
| IGHV1-69 | IGKV6-21 | 9 | 0.04% |
| IGHV1-69 | IGLV1-47 | 8 | 0.036% |
| IGHV1-69 | IGLV3-21 | 6 | 0.027% |
| IGHV1-69 | IGLV1-44 | 5 | 0.023% |
| IGHV1-69 | IGKV1D-16 | 5 | 0.023% |
| IGHV1-69 | IGKV1-13 | 5 | 0.023% |
| IGHV1-69 | IGKV3-NL4 | 3 | 0.013% |
| IGHV1-69 | IGKV2-24 | 3 | 0.013% |
| IGHV1-69 | IGKV1-8 | 3 | 0.013% |
| | | Total: 22180 | |

Example 3

Determining Antibody Binding Affinity

This example illustrates the determination of antibody binding affinity for alpha-toxin antibodies.

KinExA® Measurements

The affinities of alpha-toxin antibodies to alpha-toxin were measured on a KinExA® 3000 instrument (Sapidyne® Inc, Boise, Id.). See, Darling, R. J. & Brault, P.-A., 2005. Kinetic Exclusion Assay Technology: Characterization of Molecular Interactions. Assay and Drug Development Technologies, 2(6), pp. 647-657. All experiments were performed at room temperature using PBS pH 7.4 with 0.01% (v/v) Tween-20 as running buffer. For detection of free alpha-toxin, polymethylmethacrylate beads were adsorption-coated with DF1.1 IgG. Per experiment, 200 mg beads were prepared at room temperature by incubating them with 30 μg DF1.1 in 1 mL PBS for 2 h with rocking and blocking them in 10 mg/mL BSA in PBS for a further 1 h with rocking. Blocked beads were stored at 4° C. for up to one week. Alpha-toxin was either purchased (Calbiochem®) or obtained in conditioned media by overnight culture of the respective S. aureus strain USA300 (FPR3757, ATCC number BAA-1556), PFESA0181, PFESA0158, PFESA0140, PFESA0207, PFESA0150, and PFESA0249. Media from *S. aureus* strain PFESA0124 that did not contain an amount of alpha-toxin detectable by KinExA® served as control media. Media samples were diluted twenty-fold or 33-fold into running buffer to obtain suitable, picomolar working concentrations of alpha-toxin. Commercially available, purified alpha-toxin was diluted into running buffer that contained 1 mg/mL BSA.

In each experiment, a series of samples with a fixed concentration of alpha-toxin was titrated with a twelve-membered, twofold dilution series of the antibody to be tested (DF1.1 Fab, DF1.1 IgG, DF1 IgG, or DF2 IgG). The dilution series was prepared such that a full titration range was covered. Thus, the top concentration of antibody was typically at least thirty-fold above the alpha-toxin concentration. A thirteenth alpha-toxin sample without any antibody was used to establish the maximal signal. Volumes and concentrations were optimized per experiment. The samples were equilibrated for up to three days before free alpha-toxin was measured with the KinExA® 3000 instrument. All samples were analyzed in duplicate. Using the KinExA® software, the measured values were fit to a standard bimolecular binding equation to obtain the $K_D$ value of the alpha-toxin-antibody interaction.

The results shown in Table 4 demonstrate these antibodies have picomolar affinities for alpha-toxin, and that these antibodies bind to alpha-toxin variants from a number of different *S. aureus* strains. Best fit and the 95% confidence interval, shown in parentheses in column 3 of Table 4, was determined in the KinExA® analysis software.

TABLE 4

| mAb | alpha-toxin | $K_D$ for alpha-toxin (pM) |
|---|---|---|
| DF1 IgG | Calbiochem ® cat. no. 616385 | 37 (27-51) |
| DF1.1 IgG | Calbiochem ® cat. no. 616385 | 1.7 (1.2-2.2) |
| DF2 IgG | Calbiochem ® cat. no. 616385 | 8.3 (2.8-18) |
| DF1.1 Fab | Calbiochem ® cat. no. 616385, spiked into control media | 2.2 (1.6-3.0) |
| DF1.1 Fab | from *S. aureus* strain FPR3757 in conditioned media | 1.3 (0.9-1.9) |
| DF1.1 Fab | from *S. aureus* strain PFESA0181 in conditioned media | 1.6 (0.9-2.5) |
| DF1.1 Fab | from *S. aureus* strain PFESA0158 in conditioned media | 1.7 (1.3-2.2) |
| DF1.1 Fab | from *S. aureus* strain PFESA0140 in conditioned media | 2.0 (1.5-2.6) |
| DF1.1 Fab | from *S. aureus* strain PFESA0207 in conditioned media | 0.96 (0.33-1.9) |
| DF1.1 Fab | from *S. aureus* strain PFESA0150 in conditioned media | 0.96 (0.66-1.3) |
| DF1.1 Fab | from *S. aureus* strain PFESA0249 in conditioned media | 2.2 (2.0-2.5) |

Biacore™ Measurements

Kinetic measurements of the alpha-toxin antibody/alpha-toxin interactions were performed on a Biacore™ T200 biosensor (GE Healthcare, Piscataway, N.J.) at 37° C. To prepare a capture surface for human antibodies, polyclonal goat F(ab')$_2$ anti-human Fc (Cappel, MP Biomedicals, Solon, Ohio) was immobilized via standard amine coupling at 25° C. on a CM5 sensor chip using 60 ug/mL F(ab')$_2$ in 10 mM sodium acetate pH 5.0 and a running buffer composed of 10 mM HEPES pH 7.4, 150 mM NaCl, and 0.05% (v/v) Tween-20.

DF1, DF1.1 and DF2 were captured each on one flow cell (flow cells 2, 3, and 4) of the prepared chip, and the remaining flow cell served as a reference. Alpha-toxin (Calbiochem®) was injected as an analyte at 30 uL/min for three min. at different concentrations (150 nM, 50 nM, 17 nM, 5.6 nM, 1.9 nM). The dissociation was followed for up to 30 min before the capture surface was regenerated with three twenty-second pulses of 75 mM phosphoric acid. Buffer cycles provided blanks for double-referencing the data, which were then fit to a 1:1 binding model with mass transfer using the Biacore™ T200 evaluation software. This interaction analysis was performed in three different running buffers to test the effect of different pH values: (a) 25 mM sodium phosphate pH 7.3 at 37 C, 150 mM NaCl, 0.05% Tween-20; (b) 25 mM sodium phosphate pH 5.8 at 37 C, 150 mM NaCl, 0.05% Tween-20; (c) 25 mM sodium acetate pH 4.8 at 37 C, 150 mM NaCl, 0.05% Tween-20.

The active concentrations of purified alpha-toxin (Calbiochem) and DF1.1 Fab were determined via calibration-free concentration analysis (CFCA) on the Biacore™ by measuring their binding to an immobilized interaction partner at two different flow rates (5 uL/min and 100 uL/min). See, Sigmundsson K, Másson G, Rice R, Beauchemin N, Obrink B., 2002, *Biochemistry* 41: 8263-8276.

The results shown in Table 4A demonstrate these antibodies retain their affinity to alpha-toxin even at acidic pH.

TABLE 4A

| Biacore ™ T200, 37° C., 3 pH values tested | | | |
|---|---|---|---|
| Ligand | pH | ka (1/Ms) | kd (1/s) | $K_D$ (M) |
| DF1.1 | 4.8 | 1.2E+06 | 1.0E-04 | 8.1E-11 |
| DF1.1 | 5.8 | 9.1E+05 | 2.8E-05 | 3.1E-11 |
| DF1.1 | 7.3 | 8.1E+05 | 3.1E-05 | 3.8E-11 |
| DF1 | 4.8 | 5.7E+05 | 3.3E-04 | 5.8E-10 |
| DF1 | 5.8 | 3.0E+05 | 1.8E-04 | 5.9E-10 |
| DF1 | 7.3 | 2.4E+05 | 1.8E-04 | 7.6E-10 |
| DF2 | 4.8 | 7.4E+05 | 1.1E-04 | 1.5E-10 |
| DF2 | 5.8 | 4.2E+05 | 6.1E-05 | 1.5E-10 |
| DF2 | 7.3 | 3.4E+05 | 7.0E-05 | 2.1E-10 |

All KinExA KD values include a calibrated alpha-toxin concentration (for the purified alpha-toxin) or a calibrated DF1.1 Fab concentration (for the measurements with *S. aureus* conditioned media).

Example 4

Alpha-Toxin Antibodies are Prophylactically Protective in a Mouse Model of Staphylococcal Pneumonia; Challenge Dose-Response This example illustrates the effect of alpha-toxin antibodies in a mouse model for staphylococcal pneumonia. In this example, the effect of the alpha-toxin antibodies in animals inoculated with varying doses of bacteria was studied.

Female, fully immunocompetent Balb/c mice weighing 19-21 g were obtained from Charles River. The animals were 7-8 weeks old at the beginning of the experiment.

*S. aureus* strain USA300 LAC (a methicillin resistant strain, MRSA) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of Trypticase Soy Broth (TSB). An O.D.$_{600}$ measurement was made using a spectrophotometer. The bacterial suspension was incubated in a 37° C. water bath until the culture arrived at the target McFarland forward light scatter range of 0.600-0.650 units, providing a bacterial concentration of approximately $10^8$ colony forming units (CFU)/mL. The culture was centrifuged and the pellet was resuspended in 4 mL Trypticase™ Soy Broth (TSB) to bring the bacterial concentration to approximately $2.0 \times 10^{10}$ CFU/mL, yielding a $1 \times 10^9$ challenge in 50 μL. This concentrated culture was used to prepare dilutions in TSB for the remaining inoculum challenges of $3.16 \times 10^8$, $1 \times 10^8$ and $3.16 \times 10^7$. The inoculums challenges were confirmed by serial dilution, plating and back counting. 10 animals per group were anesthetized through use of isoflourane (induced at 5% in an induction chamber). Each animal was administered an intranasal challenge of the bacterial culture with a total volume of 50 μL. Administration of the bacterial challenge constituted time 0 h for the study.

The alpha-toxin antagonist antibody DF1.1 was formulated in phosphate buffered saline (PBS). Either DF1.1 or vehicle (PBS) treatment was administered in a single intraperitoneal (ip) dose 24 hours prior to the bacterial challenge using a 0.5 ml dosing volume. Mice receiving antibody received a dose of 30 mg/kg.

The primary endpoint used to assess progression of the infection was mortality over a 72 hour period following bacterial challenge. Graphic interpretation of the survival results (Kaplan-Meier) and statistical analysis (Log-rank/Mantel-Cox test) were performed using GraphPad Prism v.5.0 (graphs not shown). Table 5 shows the cumulative survival rate for DF1.1-treated compared to vehicle-treated (control) animals.

TABLE 5

| Challenge USA300 CFU | Treatment i.p. (−24 hr) | Cumulative survival (%) | | | | |
|---|---|---|---|---|---|---|
| | | Day 0 | Day 1 | Day 2 | Day 3 | Study end % survived |
| $1 \times 10^9$ | vehicle | 100 | 0 | 0 | 0 | 0 |
| | DF1.1 30 mg/kg | 100 | 50 | 20 | 20 | 20 |
| $3.16 \times 10^8$ | vehicle | 100 | 10 | 10 | 10 | 10 |
| | DF1.1 30 mg/kg | 100 | 100 | 90 | 90 | 90 |
| $1 \times 10^8$ | vehicle | 100 | 80 | 80 | 80 | 80 |
| | DF1.1 30 mg/kg | 100 | 100 | 100 | 100 | 100 |
| $3.16 \times 10^7$ | vehicle | 100 | 100 | 100 | 100 | 100 |
| | DF1.1 30 mg/kg | 100 | 100 | 100 | 100 | 100 |

Compared to the control, treatment with alpha-toxin antibody reduced mortality in animals challenged with up to $1 \times 10^9$ CFU USA300. As shown in Table 5, for animals challenged with $3.16 \times 10^8$ CFU USA300, treatment with alpha-toxin antagonist antibody resulted in survival rate of 90% at study end. In contrast, for the same challenge dose, the survival rate of vehicle-treated (control) animals at study end was only 10%. These results demonstrate that alpha-toxin antibodies are protective and effective in preventing death and/or reducing disease severity in a mouse model of staphylococcal pneumonia when administered prophylactically.

In another study, the effect of the alpha-toxin antibody DF2 was evaluated in a mouse model of staphylococcal pneumonia. In this study, female, fully immunocompetent Balb/c mice at 6 weeks of age were obtained from Charles River. The animals were 7-8 weeks old at the beginning of the study. S. aureus strain PFESA0140 (MSSA) was stored at −80° C. until initiated for use in the study. The culture was swabbed onto TSA (BBL, Becton Dickinson Laboratories, Franklin Lakes, N.J.), and grown at 37° C., in an ambient atmosphere. The TSA plate was used to grow an overnight liquid culture in TSB (Cellgro, Mediatech, Manassas, Va.), and a subsequent 1:100 subculture was made in TSB where bacteria were grown to an $OD_{600}=0.5$. The culture was centrifuged and the pellet was resuspended in the appropriate volume of PBS to bring the bacterial concentration to the desired concentration. Mice were challenged with an inoculum of S. aureus at approximately $6.5 \times 10^8$ CFU per animal. After serial dilution, plating and back counting the actual challenge was determined to be $7.3 \times 10^8$ CFU per animal. Prior to bacterial challenge, animals were anesthetized through intraperitoneal dose of ketamine (100 mg/kg) and xylazine (10 mg/kg). There were 5 animals in each group. Each animal was administered an intranasal challenge of the bacterial culture with a total volume of 30 μL. Instillation of the bacterial challenge constituted time 0 h for the study. mAb DF2 and isotype control Ab (hIgG) was formulated in PBS. The antibody treatment was administered at 30 mg/kg in a single intraperitoneal dose 24 hours prior to the bacterial challenge using a 0.18 ml dosing volume (average mouse weight 18 g).

The primary endpoint used to assess progression of the infection and activity of the mAb DF2 was mortality over a period of seven days following bacterial challenge. Graphic interpretation of the survival results (Kaplan-Meier) and statistical analysis (Log-rank/Mantel-Cox test) were performed using GraphPad Prism v.5.0. Table 5A shows the cumulative survival rate for DF2-treated compared to vehicle-treated (control) animals.

TABLE 5A

| Challenge PFESA0140 CFU | Treatment i.p. (−24 hr) | Cumulative survival (%) | | | | | | | |
|---|---|---|---|---|---|---|---|---|---|
| | | Day 1 | Day 2 | Day 3 | Day 4 | Day 5 | Day 6 | Day 7 | Study end % survived |
| $7.3 \times 10^8$ | DF2 | 100 | 100 | 100 | 100 | 80 | 80 | 80 | 80 |
| | Control | 20 | 0 | 0 | 0 | 0 | 0 | 0 | 0 |

Compared to the control, treatment with alpha-toxin antibody reduced mortality in animals challenged with S. aureus strain PFESA0140. As shown in Table 5A, for animals challenged with $3.16 \times 10^8$ CFU S. aureus, treatment with alpha-toxin antagonist antibody DF2 resulted in survival rate of 80% at study end. In contrast, for the same challenge dose, the survival rate of vehicle-treated (control) animals at study end was 0%. These results demonstrate that alpha-toxin antibodies are protective and effective in preventing death and/or reducing disease severity in a mouse model of staphylococcal pneumonia when administered prophylactically.

Example 5

Alpha-Toxin Antibodies are Prophylactically Protective in a Mouse Model of Staphylococcal Pneumonia; Antibody Dose-Response This example illustrates the effect of alpha-toxin antibodies in a mouse model for staphylococcal pneumonia. In this example, the dose-response effect of the alpha-toxin antibodies in a mouse model of staphylococcal pneumonia was studied.

Female, fully immunocompetent Balb/c mice weighing 19-21 g were obtained from Charles River. The animals were 7-8 weeks old at the beginning of the experiment.

S. aureus strain USA300 (LAC) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An $O.D._{600}$ measurement was made using a spectrophotometer. The bacterial suspension was incubated in a 37° C. water bath until the culture arrived at the target McFarland forward light scatter range of 0.600-0.650 units, providing a bacterial concentration of approximately $10^8$ CFU/mL. The culture was centrifuged and the pellet was resuspended in 4 mL TSB to bring the bacterial concentration to approximately $2.0 \times 10^{10}$ CFU/mL, yielding a $1 \times 10^9$ challenge in 50 µL. This concentrated culture was diluted in TSB to prepare a challenge of approximately $3.16 \times 10^8$ CFU per animal. After serial dilution, plating and back counting the actual challenge was determined to be $2.5 \times 10^8$ CFU. 10 animals per group were anesthetized through use of isoflourane (induced at 5% in an induction chamber). Each animal was administered an intranasal challenge of the bacterial culture with a total volume of 50 µL. Administration of the bacterial challenge constituted time 0 h for the study.

The alpha-toxin antagonist antibody DF1.1 was formulated in PBS. The antibody or vehicle (PBS) treatment was administered in a single intraperitoneal (ip) dose 24 hours prior to the bacterial challenge using a 0.5 ml dosing volume. Mice receiving antibody received doses of 30, 10, 3, 1, 0.3 and 0.1 mg/kg.

The primary endpoint used to assess progression of the infection and activity of the mAb DF1.1 was mortality over a period of five days following bacterial challenge. Graphic interpretation of the survival results (Kaplan-Meier) and statistical analysis (Log-rank/Mantel-Cox test) were performed using GraphPad Prism v.5.0 (graphs not shown). Table 6 shows the cumulative survival rate for DF1.1-treated compared to vehicle-treated (control) animals.

of 30% at study end. However, a 0.3 mg/kg dose of alpha-toxin antagonist antibody effectively increased the survival rate from 30% to 60%. A 1 mg/kg dose of alpha-toxin antagonist antibody increased the survival rate from 30% to 90%. At doses of 3 mg/kg and higher of alpha-toxin antagonist antibody, the survival rate was 100%. Thus, 100% protection is observed with a dose of 3 mg/kg of alpha-toxin antagonist body, and $PD_{50}$ is aboug 0.26 mg/kg. These results demonstrate that alpha-toxin antagonist antibodies are protective and effective in preventing disease and/or reducing disease severity in a mouse model of staphylococcal pneumonia when administered prophylactically.

Example 6

Alpha-Toxin Antibodies are Therapeutically Protective in a Mouse Model of Staphylococcal Pneumonia This example illustrates the therapeutic effect of alpha-toxin antibodies in a mouse model for staphylococcal pneumonia. In this example, the effect of alpha-toxin antibody treatment after S. aureas challenge was studied.

Female, fully immunocompetent Balb/c mice weighing 19-21 g were obtained from Charles River. The animals were 7-8 weeks old at the beginning of the experiment.

S. aureus strain USA300 (LAC) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An $O.D._{600}$ measurement was made using a spectrophotometer. The bacterial suspension was incubated in a 37° C. water bath until the culture arrived at the target McFarland forward light scatter range of 0.600-0.650 units, providing a bacterial concentration of approximately $10^8$ CFU/mL. The culture was centrifuged and the pellet was resuspended in 4 mL TSB to bring the bacterial concentration to approximately $2.0 \times 10^{10}$ CFU/mL, yielding a $1 \times 10^9$ challenge in 50 µL. This concentrated culture was diluted in TSB to prepare a challenge of approximately $3.16 \times 10^8$ CFU per animal. After serial dilution, plating and back counting the actual challenge was determined to

TABLE 6

| | | Cumulative survival (%) | | | | | | | | |
|---|---|---|---|---|---|---|---|---|---|---|
| | | day 0 | | | | day | day | day | day | day | Study |
| Challenge | Treatment | 2 h | 4 h | 8 h | 12 h | 1 | 2 | 3 | 4 | 5 | end |
| $2.5 \times 10^8$ CFU USA300 | 0.1 mg/kg mAb DF1.1 | 100 | 100 | 100 | 40 | 30 | 10 | 10 | 10 | 10 | 10 |
| | 0.3 mg/kg mAb DF1.1 | 100 | 100 | 100 | 80 | 80 | 60 | 60 | 60 | 60 | 60 |
| | 1 mg/kg mAb DF1.1 | 100 | 100 | 100 | 100 | 100 | 90 | 90 | 90 | 90 | 90 |
| | 3 mg/kg mAb DF1.1 | 100 | 100 | 100 | 100 | 100 | 100 | 100 | 100 | 100 | 100 |
| | 10 mg/kg mAb DF1.1 | 100 | 100 | 100 | 100 | 100 | 100 | 100 | 100 | 100 | 100 |
| | 30 mg/kg mAb DF1.1 | 100 | 100 | 100 | 100 | 100 | 100 | 100 | 100 | 100 | 100 |
| | vehicle | 100 | 100 | 100 | 60 | 60 | 40 | 30 | 30 | 30 | 30 |

Compared to the control, treatment with alpha-toxin antibody significantly reduced mortality in a dose-dependent manner. Vehicle-treated (control) animals had a survival rate be $5 \times 10^8$ CFU. 10 animals per group were anesthetized through use of isoflourane (induced at 5% in an induction chamber). Each animal was administered an intranasal challenge of the bacterial culture with a total volume of 50 μL. Administration of the bacterial challenge constituted time 0 h for the study.

The alpha-toxin antagonist antibody DF1.1 was formulated in Phosphate Buffered Saline (PBS). The antibody or vehicle treatment was administered in a single intravenous (iv) dose using a 0.1 ml dosing volume. Mice receiving antibody received doses of 30 mg/kg. The vehicle was administered 24 hours before the challenge. One group each of animals received mAb DF1.1 24 hours before or at 0, 4, 8 and 12 hours after the bacterial challenge.

The primary endpoint used to assess progression of the infection and activity of the mAb DF1.1 was mortality over a period of five days following bacterial challenge. Graphic interpretation of the survival results (Kaplan-Meier) and statistical analysis (Log-rank/Mantel-Cox test) were performed using GraphPad Prism v.5.0 (graphs not shown). Table 7 shows the cumulative survival rate for DF1.1-treated compared to vehicle-treated (control) animals.

S. aureus strain USA300 (LAC) was stored at −80° C. until initiated for use in the study. The culture was swabbed onto Trypticase™ soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An $O.D._{600}$ measurement was made using a spectrophotometer. The bacterial suspension was incubated in a 37° C. water bath until the culture arrived at the target McFarland forward light scatter range of 0.600-0.650 units, providing a bacterial concentration of approximately $10^8$ CFU/mL. The culture was centrifuged and the pellet was resuspended in 4 mL TSB to bring the bacterial concentration to approximately $2.0 \times 10^{10}$ CFU/mL, yielding a $1 \times 10^9$ challenge in 50 μL. This concentrated culture was diluted in TSB to prepare a challenge of approximately $3.16 \times 10^8$ CFU per animal. After serial dilution, plating and back counting the challenge was confirmed to be

TABLE 7

| Treatment | Time of dosing* | Cumulative survival (%) | | | | | | | | | |
|---|---|---|---|---|---|---|---|---|---|---|---|
| | | day 0 | | | | day 1 | day 2 | day 3 | day 4 | day 5 | Study end |
| | | 2 h | 4 h | 8 h | 12 h | | | | | | |
| vehicle | −24 h | 100 | 100 | 100 | 100 | 20 | 10 | 10 | 10 | 10 | 10 |
| 30 mg/kg mAb DF1.1 | −24 h | 100 | 100 | 100 | 100 | 100 | 100 | 100 | 100 | 100 | 100 |
| | 0 h | 100 | 100 | 100 | 100 | 100 | 100 | 100 | 100 | 100 | 100 |
| | 4 h | 100 | 100 | 100 | 100 | 100 | 100 | 90 | 90 | 90 | 90 |
| | 8 h | 100 | 100 | 100 | 100 | 90 | 80 | 80 | 80 | 80 | 80 |
| | 12 h | 100 | 100 | 100 | 100 | 100 | 80 | 80 | 80 | 80 | 80 |

*Time is relative to time of bacterial inoculation (challenge). Bacterial challenge was $5 \times 10^8$ CFU S. aureus USA300.

Compared to the control, treatment with alpha-toxin antibody significantly reduced mortality when administered therapeutically. Treatment with alpha-toxin antagonist antibody 12 or 8 hours after S. aureus challenge resulted in a survival rate of 80% at study end. In contrast, animals treated with vehicle only had a 10% survival rate at study end. Treatment with alpha-toxin antagonist antibody 4 hours after S. aureus challenge resulted in a survival rate of 90% at study end. Treatment with alpha-toxin antagonist antibody 24 hours before or at the time of S. aureus challenge resulted in a survival rate of 100% at study end. These results demonstrate that alpha-toxin antagonist antibodies are protective and effective in reducing disease severity in a mouse model of staphylococcal pneumonia when administered therapeutically after S. aureus challenge.

Example 7

Alpha-Toxin Antibodies are Therapeutically Protective in a Mouse Model of Staphylococcal Pneumonia; Comparison to Linezolid This example illustrates the therapeutic effect of alpha-toxin antibodies in a mouse model for staphylococcal pneumonia. In this example, the effect of alpha-toxin antibody treatment was studied in comparison to linezolid (an antibiotic) treatment.

Female, fully immunocompetent Balb/c mice weighing 19-21 g were obtained from Charles River. The animals were 7-8 weeks old at the beginning of the experiment.

$3.16 \times 10^8$ CFU. 10 animals per group were anesthetized through use of isoflourane (induced at 5% in an induction chamber). Each animal was administered an intranasal challenge of the bacterial culture with a total volume of 50 μL. Instillation of the bacterial challenge constituted time 0 h for the study.

The alpha-toxin antagonist antibody DF1.1 was formulated in PBS. The antibody or vehicle treatment was administered in a single intravenous (iv) dose using a 0.1 ml dosing volume. The commercial antibacterial chemotherapeutic linezolid was provided by Pfizer and formulated at a dosing concentration of 12 mg/kg in an aqueous solution of 5% polyethylene glycol (PEG200), 0.5% methylcellulose. The linezolid treatment was administered by oral gavage (po) in a single dose using a 0.5 mL dosing volume. Mice receiving antibody received doses of 30 mg/kg. The vehicle was administered 24 hours before the challenge. One group each of animals received mAb DF1.1 24 hours before or at 0, 4, 8, 12 and 18 hours after the bacterial challenge. One group each of animals received linezolid at 0, 4, 8, 12 and 18 hours after the bacterial challenge.

The primary endpoint used to assess progression of the infection and activity of the mAb DF1.1 was mortality over a period of five days following bacterial challenge. Graphic interpretation of the survival results (Kaplan-Meier) and statistical analysis (Log-rank/Mantel-Cox test) were performed using GraphPad Prism v.5.0 (graphs not shown). Table 8 shows the cumulative survival rate for DF1.1-treated and linezolid-treated compared to vehicle-treated (control) animals.

TABLE 8

| Treatment | Time of dosing* | Cumulative survival (%) | | | | | | | | | |
|---|---|---|---|---|---|---|---|---|---|---|---|
| | | day 0 | | | | day 1 | day 2 | day 3 | day 4 | day 5 | Study end |
| | | 2 h | 4 h | 8 h | 12 h | | | | | | |
| vehicle | −24 h | 100 | 100 | 100 | 100 | 60 | 30 | 10 | 10 | 10 | 10 |
| 30 mg/kg mAb DF1.1 | −24 h | 100 | 100 | 100 | 100 | 100 | 100 | 100 | 100 | 100 | 100 |
| | 0 h | 100 | 100 | 100 | 100 | 100 | 100 | 100 | 100 | 100 | 100 |
| | 4 h | 100 | 100 | 100 | 100 | 100 | 100 | 100 | 100 | 100 | 100 |
| | 8 h | 100 | 100 | 100 | 100 | 100 | 100 | 100 | 100 | 100 | 100 |
| | 12 h | 100 | 100 | 100 | 100 | 100 | 100 | 100 | 100 | 100 | 100 |
| | 18 h | 100 | 100 | 100 | 100 | 80 | 50 | 50 | 50 | 50 | 50 |
| 12 mg/kg linezolid | 0 h | 100 | 100 | 100 | 100 | 100 | 100 | 100 | 100 | 100 | 100 |
| | 4 h | 100 | 100 | 100 | 100 | 100 | 100 | 100 | 100 | 100 | 100 |
| | 8 h | 100 | 100 | 100 | 100 | 100 | 100 | 100 | 100 | 100 | 100 |
| | 12 h | 100 | 100 | 100 | 100 | 100 | 100 | 100 | 100 | 100 | 100 |
| | 18 h | 100 | 100 | 100 | 100 | 60 | 40 | 40 | 40 | 40 | 40 |

*Time is relative to time of bacterial inoculation (challenge). Challenge was $3.16 \times 10^8$ CFU S. aureus USA300.

Compared to the control, treatment with alpha-toxin antibody significantly reduced mortality when administered prophylactically or therapeutically in a mouse model of staphylococcal pneumonia. Treatment with alpha-toxin antagonist antibody 18 hours after S. aureus challenge resulted in a survival rate of 50% at study end. In contrast, animals treated with vehicle had a 10% survival rate at study end. Treatment with alpha-toxin antagonist antibody 12, 8 or 4 hours after S. aureus challenge resulted in a survival rate of 100% at study end. Treatment with alpha-toxin antagonist antibody 24 hours before or at the time of S. aureus challenge resulted in a survival rate of 100% at study end.

Treatment with linezolid 18 hours after S. aureus challenge resulted in a survival rate of 40% at study end. Treatment with linezolid 12, 8 or 4 hours after S. aureus challenge resulted in a survival rate of 100% at study end. Treatment with linezolid at the time of S. aureus challenge resulted in a survival rate of 100% at study end. Based on the study results, for at least the dosages tested in the study, treatment with an alpha-toxin antagonist antibody is at least as effective as treatment with linezolid in preventing death and/or reducing disease severity in a mouse model of staphylococcal pneumonia.

Example 8

Alpha-Toxin Antibodies in Combination with Linezolid are Prophylactically Protective in a Mouse Model of Staphylococcal Pneumonia This example illustrates the effect of alpha-toxin antibodies in a mouse model for staphylococcal pneumonia. In this example, the effect of alpha-toxin antibody treatment was studied in combination with linezolid treatment.

Female, fully immunocompetent Balb/c mice weighing 19-21 g were obtained from Harlan. The animals were 7-8 weeks old at the beginning of the experiment.

S. aureus strain USA300 (LAC) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An $O.D._{600}$ measurement was made using a spectrophotometer. The bacterial suspension was incubated in a 37° C. water bath until the culture arrived at the target McFarland forward light scatter range of 0.600-0.650 units, providing a bacterial concentration of approximately $1 \times 10^9$ CFU/mL. The culture was centrifuged and the pellet was resuspended in 4 mL TSB to bring the bacterial concentration to approximately $2.0 \times 10^{10}$ CFU/mL, yielding an approximate challenge of $1 \times 10^9$ organisms in 50 µL. After serial dilution, plating and back counting the challenge was determined to be $1.3 \times 10^9$ CFU. 10 animals per group were anesthetized through use of isoflourane (induced at 5% in an induction chamber). Each animal was administered an intranasal challenge of the bacterial culture with a total volume of 50 µL. Administration of the bacterial challenge constituted time 0 h for the study.

The alpha-toxin antagonist antibody mAb DF1.1 was formulated in PBS. The antibody or vehicle treatment was administered in a single intraperitoneal (ip) dose using a 0.5 ml dosing volume 24 hours before the challenge. Mice receiving antibody received doses of 30 mg/kg. The commercial antibacterial chemotherapeutic linezolid was provided by Pfizer and formulated at a dosing concentration of 12.5 mg/kg in an aqueous solution of 5% polyethylene glycol (PEG200), 0.5% methylcellulose. The linezolid treatment was administered by oral gavage (po) in a single dose using a 0.5 mL dosing volume. Linezolid was administered at the time of the challenge.

The primary endpoint used to assess progression of the infection and activity of the mAb DF1.1 was mortality over a period of five days following bacterial challenge. Graphic interpretation of the survival results (Kaplan-Meier) and statistical analysis (Log-rank/Mantel-Cox test) were performed using GraphPad Prism v.5.0 (graphs not shown). Table 9 shows the cumulative survival rate for DF1.1-treated, linezolid-treated, DF1.1 and linezolid combination-treated, and vehicle-treated (control) animals.

TABLE 9

| Challenge | Treatment | Dose time | Day 0 | Day 1 | Day 2 | Day 3 | Day 4 | Day 5 | Study end |
|---|---|---|---|---|---|---|---|---|---|
| 1.3 × 10⁹ CFU USA300 | vehicle, i.p. | −24 hr | 100 | 0 | 0 | 0 | 0 | 0 | 0 |
| | linezolid, 12.5 mg/kg, p.o. | 0 hr | 100 | 100 | 50 | 40 | 40 | 40 | 40 |
| | DF1.1, 30 mg/kg, i.p. | −24 hr | 100 | 100 | 50 | 50 | 50 | 50 | 50 |
| | DF1.1, 30 mg/kg, i.p. + linezolid, 12.5 mg/kg, p.o. | DF1.1 at −24 hr, linezolid at 0 hr | 100 | 100 | 100 | 90 | 90 | 90 | 90 |

Compared to the control, prophylactic treatment with alpha-toxin antibody in combination with linezolid treatment significantly reduced mortality in a mouse model of staphylococcal pneumonia. Combination treatment with alpha-toxin antagonist antibody and linezolid resulted in a survival rate of 90% at study end. At days 1 and 2 of the study, the combination-treated animals had a cumulative survival of 100%. In contrast, all control animals treated with vehicle died by day 1 of the study. Treatment with either linezolid alone or alpha-toxin antagonist antibody alone resulted in a cumulative survival of 50% by day 2 of the study. Treatment with alpha-toxin antagonist antibody resulted in a survival rate of 50% at study end. Treatment with linezolid resulted in a survival rate of 40% at study end. These results demonstrate that combination treatment with alpha-toxin antagonist antibody and linezolid is protective and effective to prevent death and/or reduce disease severity in a mouse model of staphylococcal pneumonia, and that the protective effect of the combination treatment is at least additive. Furthermore, at the dosages tested, the combination treatment with alpha-toxin antagonist antibody and linezolid was more effective than either linezolid or antibody alone.

Additional endpoints of bacterial burden in lung and kidneys were obtained for animals surviving the full 5 days of observation. Mice were euthanized and lung and kidneys were aseptically removed, weighed and transferred to homogenization vials. All tissue was homogenized through use of a Mini-BeadBeater™ (Bio-Spec™ Products). Ten-fold serial dilutions of each sample were prepared in sterile TSB and cultured on blood agar plates. The plates were incubated at 37° C. at ambient atmosphere overnight and colonies were enumerated. The total lung and kidney bacterial burdens per gram of tissue were calculated for each mouse. Table 10 shows the total lung bacterial burdens for each group of animals, and Table 11 shows the total kidney bacterial burdens for each group of animals.

TABLE 10

| | CFU/g Lung Tissue (log10) | | |
|---|---|---|---|
| Treatment: | Linezolid | mAb DF1.1 | DF1.1 + Linezolid |
| mouse #1 | 3.13 | 7.52 | 3.39 |
| mouse #2 | 7.64 | 8.35 | 3.43 |
| mouse #3 | 4.36 | 5.35 | 3.45 |
| mouse #4 | 3.55 | 6.77 | 3.99 |
| mouse #5 | Dead | 8.33 | 3.64 |
| mouse #6 | Dead | Dead | 5.76 |
| mouse #7 | Dead | Dead | 3.61 |
| mouse #8 | Dead | Dead | 4.32 |
| mouse #9 | Dead | Dead | 3.51 |
| mouse #10 | Dead | Dead | Dead |

TABLE 10-continued

| | CFU/g Lung Tissue (log10) | | |
|---|---|---|---|
| Treatment: | Linezolid | mAb DF1.1 | DF1.1 + Linezolid |
| mean CFU/g | 4.67 | 7.27 | 3.90 |
| n | 4.00 | 5.00 | 9.00 |
| Stdev | 2.05 | 1.25 | 0.76 |
| Std err | 1.02 | 0.56 | 0.25 |

TABLE 11

| | CFU/g Kidney Tissue (log10) | | |
|---|---|---|---|
| Treatment: | Linezolid | mAb DF1.1 | DF1.1 + Linezolid |
| mouse #1 | 0.00 | 4.41 | 0.00 |
| mouse #2 | 5.95 | 6.02 | 0.00 |
| mouse #3 | 3.77 | 3.69 | 0.00 |
| mouse #4 | 3.21 | 3.10 | 0.00 |
| mouse #5 | Dead | 5.02 | 3.15 |
| mouse #6 | Dead | Dead | 0.00 |
| mouse #7 | Dead | Dead | 0.00 |
| mouse #8 | Dead | Dead | 0.00 |
| mouse #9 | Dead | Dead | 0.00 |
| mouse #10 | Dead | Dead | Dead |
| mean CFU/g | 3.23 | 4.45 | 0.35 |
| n | 4.00 | 5.00 | 9.00 |
| Stdev | 2.46 | 1.14 | 1.05 |
| Std err | 1.23 | 0.51 | 0.35 |

As shown in Table 10, the mean CFU/g in lung tissue was 4.67 log 10, 7.27 log 10, and 3.90 log 10 in surving linezolid-treated, alpha-toxin antagonist antibody-treated, and combination linezolid+alpha-toxin antagonist antibody-treated animals, respectively. As shown in Table 11, the mean CFU/g in kidney tissue was 3.23 log 10, 4.45 log 10, and 0.35 log 10 in surviving linezolid-treated, alpha-toxin antagonist antibody-treated, and combination linezolid+alpha-toxin antagonist antibody-treated animals, respectively. These results demonstrate that alpha-toxin antagonist antibody treatment in combination with linezolid treatment effectively reduced the bacterial burden in kidney tissue.

Example 9

Alpha-Toxin Antibodies are Prophylactically Protective in a Mouse Model of Staphylococcal Pneumonia with a Methicillin-Sensitive *S. Aureus* Strain (MSSA)

This example illustrates the effect of alpha-toxin antibodies in a mouse model for staphylococcal pneumonia. In this example, the effect of alpha-toxin antibodies in mice challenged with a methicillin sensitive *S. aureus* strain (MSSA) was studied.

Female, fully immunocompetent Balb/c mice at 6 weeks of age were obtained from Charles River. The animals were 7-8 weeks old at the beginning of the experiment.

The MSSA strain PFESA0140 was stored at −80° C. until initiated for use in the study. The culture was swabbed onto Trypticase™ soy agar plates (TSA) (BBL, Becton Dickinson Laboratories, Franklin Lakes, N.J.), and grown at 37° C., in an ambient atmosphere. The TSA plate was used to grow an overnight liquid culture in TSB, and a subsequent 1:100 subculture was made in TSB where bacteria were grown to an $OD_{600}=0.5$. The culture was centrifuged and the pellet was resuspended in the appropriate volume of PBS to bring the bacterial concentration to the desired concentration. In this experiment mice were challenged with three different inoculums of *S. aureus* at approximately $1\times10^9$, $8\times10^8$, and $4\times10^8$ CFU per animal. After serial dilution, plating and back counting the actual challenge was determined to be $1.3\times10^9$, $7.5\times10^8$, and $4.8\times10^8$ CFU per animal. Prior to bacterial challenge, animals were anesthetized through an intraperitoneal dose of ketamine (100 mg/kg) and xylazine (10 mg/kg). There were 10 to 11 animals in each group. Each animal was administered an intranasal challenge of the bacterial culture with a total volume of 30 μL. Administration of the bacterial challenge constituted time 0 h for the study.

The alpha-toxin antagonist antibody DF1.1 and isotype control Ab (hIgG) were each formulated in PBS. Either DF1.1 or isotype control antibody was administered at 30 mg/kg in a single intraperitoneal dose 24 hours prior to the bacterial challenge using a 0.18 ml dosing volume (average mouse weight 18 g).

The primary endpoint used to assess progression of the infection and activity of the mAb DF1.1 was mortality over a period of five days following bacterial challenge. Graphic interpretation of the survival results (Kaplan-Meier) and statistical analysis (Log-rank/Mantel-Cox test) were performed using GraphPad Prism v.5.0 (graphs not shown). Table 12 shows the cumulative survival rate for DF1.1-treated compared to isotype control-treated animals.

PFESA0140 were dead by day 1 of the study (0% survival rate). The results demonstrate that alpha-toxin antagonist antibodies are protective and effective against challenge with PFESA0140, a methicillin-sensitive strain, to prevent death and/or reduce disease severity in a mouse model of staphylococcal pneumonia.

Example 10

Alpha-Toxin Antibodies are Prophylactically Protective in Neutropenic Animals in a Mouse Model of Staphylococcal Pneumonia This example illustrates the effect of alpha-toxin antibodies in a mouse model for staphylococcal pneumonia. In this example, the effect of alpha-toxin antibodies in neutropenic animals was studied.

Female, fully immunocompetent Balb/c mice weighing 19-21 g were obtained from Charles River. The animals were 7-8 weeks old at the beginning of the experiment.

*S. aureus* strain USA300 (LAC) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An $O.D._{600}$ measurement was made using a spectrophotometer. The bacterial suspension was incubated in a 37° C. water bath until the culture arrived at the target McFarland forward light scatter range of approximately 0.65 units, providing a target bacterial concentration of approximately $2.0\times10^9$ CFU/mL. The undiluted preliminary culture was used as the stock that was diluted to prepare challenge cultures of approximately $1\times10^8$ and $4\times10^7$ per 50 μL volume per mouse. After serial dilution, plating and back counting the actual challenges were determined to be $1.6\times10^7$ and $2.5\times10^7$ per 50 μL volume per mouse. 10 animals per group were anesthetized through use of isoflourane (induced at 5% in an induction chamber). Each animal was administered an intranasal challenge of the bac-

TABLE 12

| Challenge MSSA CFU | mAb treatment at −24 hr | # mice | Cumulative survival (%) | | | | | |
|---|---|---|---|---|---|---|---|---|
| | | | Day 1 | Day 2 | Day 3 | Day 4 | Day 5 | Study end |
| $1.3 \times 10^9$ | 30 mg/kg DF1.1 | 11 | 100 | 91 | 91 | 91 | 91 | 91 |
| $1.3 \times 10^9$ | 30 mg/kg isotype control | 10 | 0 | 0 | 0 | 0 | 0 | 0 |
| $7.5 \times 10^8$ | 30 mg/kg DF1.1 | 10 | 90 | 90 | 90 | 90 | 90 | 90 |
| $7.5 \times 10^8$ | 30 mg/kg isotype control | 10 | 0 | 0 | 0 | 0 | 0 | 0 |
| $4.8 \times 10^8$ | 30 mg/kg DF1.1 | 10 | 100 | 100 | 100 | 100 | 100 | 100 |
| $4.8 \times 10^8$ | 30 mg/kg isotype control | 10 | 100 | 100 | 100 | 100 | 100 | 100 |

Compared to control, treatment with alpha-toxin antibody significantly reduced mortality in animals challenged with $7.5\times10^8$ or $1.3\times10^9$ CFU PFESA0140 in a mouse model of *staphylococcus* pneumonia. As shown in Table 12, treatment with alpha-toxin antagonist antibody resulted in a 90% survival rate for animals challenged with $7.5\times10^8$ CFU PFESA0140. In contrast, for the same challenge dose, all (10 out of 10) isotype control-treated animals died by day 1 of the study (0% survival rate). Treatment with alpha-toxin antagonist antibody resulted in a 91% survival rate for animals challenged with $1.3\times10^9$ CFU PFESA0140. All isotype control-treated animals challenged with $1.3\times10^9$ CFU terial culture with a total volume of 50 μL. Administration of the bacterial challenge constituted time 0 h for the study.

The alpha-toxin antagonist antibody DF1.1 was formulated in PBS. The antibody or vehicle treatment was administered in a single intraperitoneal (ip) dose 24 hours prior to the bacterial challenge using a 0.5 ml dosing volume. Antibody was dosed at 30 mg/kg of body weight. The commercial antibiotic chemotherapeutic linezolid was formulated for oral dosing at a concentration of 12.5 mg/kg in an aqueous solution of 5% polyethylene glycol (PEG200), 0.5% methylcellulose. Linezolid was administered in a single oral dose using a 0.5 mL dosing volume immediately following the bacterial challenge.

All mice were rendered neutropenic through a series of injections with cyclophosphamide. On study Day −4 all mice received an intraperitoneal (ip) injection of 150 mg/kg cyclophosphamide followed by a second 100 mg/kg ip administration on Day −1.

The primary endpoint used to assess progress of the infection and therapeutic efficacy of mAb DF1.1, linezolid or the combination of DF1.1 and linezolid was bacterial mediated death. Deaths were closely monitored over 5 days to accurately capture mortality. Graphic interpretation of the survival results (Kaplan-Meier) and statistical analysis (Log-rank/Mantel-Cox test) were performed using GraphPad Prism v.5.0 (graphs not shown). The median day of survival was also calculated within the Kaplan-Meier analyses. The median survival time is calculated as the smallest survival time for which the survival function is less than or equal to 0.5. Median survival times are calculated as undefined where the value is larger than the largest observed time (5 days). Table 13 shows the cumulative survival rate for DF1.1-treated, linezolid-treated, DF1.1 and linezolid combination-treated and vehicle-treated neutropenic animals.

TABLE 13

| Challenge USA300 CFU | Treatment | Dose time | Cumulative survival (%) | | | | | | |
|---|---|---|---|---|---|---|---|---|---|
| | | | Day 0 | Day 1 | Day 2 | Day 3 | Day 4 | Day 5 | Study end |
| $1.6 \times 10^7$ | Vehicle | −24 h | 100 | 80 | 20 | 0 | 0 | 0 | 0 |
| $1.6 \times 10^7$ | 12.5 mg/kg linezolid | 0 h | 100 | 100 | 100 | 100 | 90 | 90 | 90 |
| $1.6 \times 10^7$ | 30 mg/kg DF1.1 | −24 h | 100 | 100 | 80 | 50 | 50 | 50 | 50 |
| $2.5 \times 10^7$ | Vehicle | −24 h | 100 | 30 | 0 | 0 | 0 | 0 | 0 |
| $2.5 \times 10^7$ | 12.5 mg/kg linezolid | 0 h | 100 | 100 | 60 | 20 | 20 | 20 | 20 |
| $2.5 \times 10^7$ | 30 mg/kg DF1.1 | −24 h | 100 | 100 | 50 | 20 | 10 | 10 | 10 |
| $2.5 \times 10^7$ | 30 mg/kg DF1.1 + 12.5 mg/kg linezolid | DF1.1 at −24 h; linezolid at 0 h | 100 | 100 | 100 | 80 | 40 | 40 | 40 |

Table 14 shows the median survival time in days for DF1.1-treated, linezolid-treated, DF1.1 and linezolid combination-treated and vehicle-treated neutropenic animals.

TABLE 14

| Challenge USA300 CFU | Treatment | Median survival time (days) |
|---|---|---|
| $1.6 \times 10^7$ | Vehicle | 2 |
| $1.6 \times 10^7$ | 12.5 mg/kg linezolid | 4 |
| $1.6 \times 10^7$ | 30 mg/kg DF1.1 | >5 |
| $2.5 \times 10^7$ | Vehicle | 1 |
| $2.5 \times 10^7$ | 12.5 mg/kg linezolid | 2.5 |
| $2.5 \times 10^7$ | 30 mg/kg DF1.1 | 3 |
| $2.5 \times 10^7$ | 30 mg/kg DF1.1 + 12.5 mg/kg linezolid | 4 |

Compared to control, treatment with alpha-toxin antibody significantly reduced mortality in neutropenic animals challenged with $1.6 \times 10^7$ or $2.5 \times 10^7$ CFU USA300 in a mouse model of staphylococcal pneumonia. As shown in Table 13, treatment with alpha-toxin antagonist antibody resulted in a 50% survival rate for neutropenic animals challenged with $1.6 \times 10^7$ CFU USA300, and treatment with linezolid resulted in a 90% survival rate for neutropenic animals challenged with $1.6 \times 10^7$ CFU USA300. In contrast, for the same challenge dose, all vehicle-treated neutropenic animals died by day 3 of the study (0% survival rate). As shown in Table 14, compared to the vehicle control, treatment with 30 mg/kg alpha-toxin antagonist antibody increased the median survival time from 2 days to >5 days in animals challenged with neutropenic animals challenged with $1.6 \times 10^7$ CFU USA300.

Cumulative survival for alpha-toxin antagonist antibody-treated neutropenic animals challenged with $2.5 \times 10^7$ CFU USA300 was 100% at day 1, 50% at day 2, 20% at day 3, and 10% at days 4 and 5. Cumulative survival for linezolid-treated neutropenic animals challenged with $2.5 \times 10^7$ CFU USA300 was 100% at day 1, 60% at day 2, and 20% at days 3, 4 and 5. Cumulative survival for alpha-toxin antagonist antibody and linezolid combination-treated neutropenic animals challenged with $2.5 \times 10^7$ CFU USA300 was 100% at days 1 and 2, 80% at day 3, and 40% at days 4 and 5. In contrast, cumulative survival for vehicle-treated neutropenic animals challenged with $2.5 \times 10^7$ CFU USA300 was 30% at day 1, 0% at days 2, 3, 4 and 5. As shown in Table 14, compared to the vehicle control, treatment with 30 mg/kg alpha-toxin antagonist antibody increased the median survival time from 1 day to 3 days in neutropenic animals challenged with $1.5 \times 10^7$ CFU USA300. Treatment with 30 mg/kg alpha-toxin antagonist antibody in combination with linezolid increased the median survival time to 4 days. These results demonstrate that alpha-toxin antagonist antibody treatment is protective and effective against *S. aureas* challenge to reduce disease severity in neutropenic mice in a mouse model of staphylococcal pneumonia, and that at the doses tested, the combination of alpha-toxin antagonist antibody and linezolid is more efficacious that either treatment alone.

Example 11

Alpha-Toxin Antibodies are Prophylactically Protective in a Mouse Model of Staphylococcal Bacteremia; Challenge Dose-Response This example illustrates the effect of alpha-toxin antibodies in a mouse model for staphylococcal bacteremia.

Female, fully immunocompetent Balb/c mice weighing 19-21 g were obtained from Charles River. The animals were 7-8 weeks old at the beginning of the experiment.

*S. aureus* strain USA300 (LAC) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An $O.D._{600}$ measurement was made using a spectrophotometer. The bacterial suspension was incubated in a 37° C. water bath until the culture arrived at the target McFarland forward light scatter range of 0.600-0.650 units, providing a bacterial concentration of approximately $1 \times 10^9$ CFU/mL. The culture was centrifuged and the pellet was resuspended in 4 mL TSB to bring the bacterial concentration to approximately $2.0 \times 10^{10}$ CFU/mL, yielding a $1 \times 10^9$ challenge in 100 µL. This concentrated culture was used to prepare dilutions in TSB for the study, namely approximately $1.6 \times 10^8$, $4 \times 10^7$, $1.6 \times 10^7$ and $4 \times 10^6$ in 100 µL. After serial dilution, plating and back counting the actual challenges were determined to be $1.6 \times 10^8$, $3.2 \times 10^8$, $1 \times 10^7$ and $3.2 \times 10^6$ CFU in 100 µL. 10 animals per group were anesthetized through use of isoflourane (induced at 5% in an induction chamber). Each animal was administered the intravenous challenge of the appropriate bacterial culture with a total volume of 100 µL in the lateral tail vain. Administration of the bacterial challenge constituted time 0 h for the study.

The alpha-toxin antagonist antibody DF1.1 was formulated in PBS. The antibody or vehicle treatment was administered in a single intraperitoneal (ip) dose 24 hours prior to the bacterial challenge using a 0.5 ml dosing volume. Mice receiving antibody received a dose of 30 mg/kg.

The primary endpoint used to assess progression of the infection and activity of the mAb DF1.1 was mortality over a 10 day period following bacterial challenge. Graphic interpretation of the survival results (Kaplan-Meier) and statistical analysis (Log-rank/Mantel-Cox test) were performed using GraphPad Prism v.5.0 (graphs not shown). Table 15 shows the cumulative survival rate for DF1.1-treated and vehicle-treated animals. Table 16 shows the median survival time in days for DF1.1-treated and vehicle-treated animals.

TABLE 15

| CFU | treatment | Cumulative survival (%) | | | | | | | | | | |
|---|---|---|---|---|---|---|---|---|---|---|---|---|
| | | day 1 | day 2 | day 3 | day 4 | day 5 | day 6 | day 7 | day 8 | day 9 | day 10 | Study end |
| $1.6 \times 10^8$ | vehicle | 100 | 0 | 0 | 0 | 0 | 0 | 0 | 0 | 0 | 0 | 0 |
| | DF1.1 | 100 | 0 | 0 | 0 | 0 | 0 | 0 | 0 | 0 | 0 | 0 |
| $3.2 \times 10^7$ | vehicle | 100 | 30 | 0 | 0 | 0 | 0 | 0 | 0 | 0 | 0 | 0 |
| | DF1.1 | 100 | 100 | 70 | 10 | 0 | 0 | 0 | 0 | 0 | 0 | 0 |
| $1 \times 10^7$ | vehicle | 100 | 100 | 100 | 100 | 80 | 50 | 40 | 40 | 40 | 40 | 40 |
| | DF1.1 | 100 | 100 | 100 | 100 | 100 | 100 | 100 | 100 | 100 | 90 | 90 |
| $3.2 \times 10^6$ | vehicle | 100 | 100 | 100 | 100 | 100 | 90 | 90 | 90 | 80 | 80 | 80 |
| | DF1.1 | 100 | 100 | 100 | 100 | 100 | 100 | 100 | 100 | 100 | 100 | 100 |

TABLE 16

| Challenge | $1.6 \times 10^8$ | $3.2 \times 10^7$ | $1 \times 10^7$ | $3.2 \times 10^6$ |
|---|---|---|---|---|
| P value | 1 | 0.0001 | 0.0049 | 0.1464 |
| DF1.1 median survival (days) | 1 | 3 | >10 | >10 |
| Vehicle median survival (days) | 1 | 1 | 5.5 | >10 |

Compared to control, treatment with alpha-toxin antibody significantly reduced mortality in animals challenged with $1 \times 10^7$ CFU USA300 in a mouse model of staphylococcal bacteremia. As shown in Table 15, cumulative survival for alpha-toxin antagonist antibody-treated animals challenged with $1 \times 10^7$ CFU USA300 was 100% at days 1-9, and 90% at day 10. Cumulative survival for vehicle-treated animals challenged with $1 \times 10^7$ CFU USA300 was 100% at days 1-4, 80% at day 5, 50% at day 6, and 40% at days 7-10. Cumulative survival for alpha-toxin antagonist antibody-treated animals challenged with $3.2 \times 10^7$ CFU USA300 was 100% at days 1 and 2, 70% at day 3, and 10% at day 4. Cumulative survival for vehicle-treated animals challenged with $3.2 \times 10^7$ CFU USA300 was 100% at day 1, 30% at day 2, and 0% by day 3. As shown in Table 16, treatment with alpha-toxin antagonist antibody resulted in a longer median survival time for animals challenged with $3.2 \times 10^7$ or $1 \times 10^7$ CFU USA300. These results demonstrate that alpha-toxin antagonist antibody treatment is protective and effective against S. aureus challenge to prolong survival and/or reduce disease severity in a mouse model of staphylococcal bacteremia. These results further demonstrate that alpha-toxin antagonist antibody treatment extends median survival time with a $3.2 \times 10^7$ CFU challenge and significantly increases survival rates with a $1 \times 10^7$ or $3.2 \times 10^6$ CFU challenge in a mouse model of staphylococcal bacteremia.

Example 12

Alpha-toxin Antibodies Are Prophylactically Protective in a Mouse Model of Staphylococcal Bacteremia; Comparison to Linezolid This example illustrates the effect of alpha-toxin antibodies in a mouse model for staphylococcal bacteremia. In this example, the effect of alpha-toxin antibody treatment was studied in comparison to linezolid treatment.

Female, fully immunocompetent Balb/c mice weighing 19-21 g were obtained from Charles River. The animals were 7-8 weeks old at the beginning of the experiment.

S. aureus strain USA300 (LAC) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An $O.D._{600}$ measurement was made using a spectrophotometer. The bacterial suspension was incubated in a 37° C. water bath until the culture arrived at the target McFarland forward light scatter range of 0.600-0.650 units, providing a bacterial concentration of approximately $1 \times 10^9$ colony forming units (CFU)/mL. This culture was used as the inoculum challenge stock and diluted to provide approximately $1.6 \times 10^7$ bacteria in 100 µL. After serial dilution, plating and back counting the actual challenge was determined to be $2 \times 10^7$ CFU in 100 µL. 10 animals per group were anesthetized through use of isoflourane (induced at 5% in an induction chamber). Each animal was administered the intravenous challenge with a total volume of 100 μL in the lateral tail vain. Administration of the bacterial challenge constituted time 0 h for the study.

The alpha-toxin antagonist antibody DF1.1 and the hIgG control were each formulated in PBS. The antibodies and the vehicle treatment were each administered in a single intraperitoneal (ip) dose 24 hours prior to the bacterial challenge using a 0.5 mL dosing volume. Mice receiving antibody (either DF1.1 or hIgG control) received a dose of 30 mg/kg. The commercial antibacterial chemotherapeutic linezolid was provided by Pfizer and formulated at a dosing concentration of 6.25 mg/kg in an aqueous solution of 5% polyethylene glycol (PEG200), 0.5% methylcellulose. The linezolid treatment was administered by oral gavage (po) in a single dose using a 0.5 mL dosing volume.

The primary endpoint used to assess progression of the infection and activity of the mAb DF1.1 was mortality over a 14 day period following bacterial challenge. Graphic interpretation of the survival results (Kaplan-Meier) and statistical analysis (Log-rank/Mantel-Cox test, median survival time) were performed using GraphPad Prism v.5.0 (graphs not shown). Table 17 shows the cumulative survival rate for DF1.1-treated, linezolid-treated, hIgG control-treated and vehicle-treated animals.

TABLE 17

| Treatment (dose, route, time) | Cumulative survival (%) | | | | | | |
|---|---|---|---|---|---|---|---|
| | Day 1 | Day 2 | Day 3 | Day 4 | Day 5 | Day 6 | Day 7 |
| vehicle, i.p., −24 hr | 100 | 100 | 90 | 90 | 90 | 80 | 70 |
| Linezolid, 6.25 mg/kg, p.o., 0 hr | 100 | 100 | 100 | 100 | 80 | 80 | 70 |
| DF1.1, 30 mg/kg, i.p., −24 hr | 100 | 100 | 100 | 100 | 90 | 90 | 90 |
| hIgG control, 30 mg/kg, i.p., −24 hr | 100 | 100 | 100 | 100 | 90 | 70 | 50 |

| Treatment (dose, route, time) | Day 8 | Day 9 | Day 10 | Day 11 | Day 12 | Day 13 | Day 14 |
|---|---|---|---|---|---|---|---|
| Vehicle, i.p., −24 hr | 70 | 30 | 30 | 30 | 30 | 30 | 30 |
| Linezolid, 6.25 mg/kg, p.o., 0 hr | 70 | 70 | 70 | 70 | 70 | 70 | 70 |
| DF1.1, 30 mg/kg, i.p., −24 hr | 80 | 70 | 70 | 70 | 70 | 70 | 70 |
| hIgG control, 30 mg/kg, i.p., −24 hr | 40 | 40 | 40 | 40 | 40 | 40 | 40 |

Compared to the control, treatment with alpha-toxin antibody significantly reduced mortality when administered prophylactically in a mouse model of staphylococcal bacteremia. Treatment with alpha-toxin antagonist antibody 24 hours prior to S. aureus challenge resulted in 90% cumulative survival at day 7 and a survival rate of 70% at day 14 (study end). In contrast, animals treated with vehicle had 70% cumulative survival at day 7 and a 30% survival rate at study end, and animals treated with the hIgG control had 50% cumulative survival at day 7 and a 40% survival rate at study end. Treatment with linezolid at the time of S. aureus challenge resulted in 70% cumulative survival at day 7 and a 70% survival rate at study end. These results demonstrate that treatment with an alpha-toxin antagonist antibody (30 mg/kg) is at least as effective as treatment with linezolid (6.25 mg/kg) in preventing death and/or reducing disease severity in a mouse model of staphylococcal bacteremia.

Example 13

Alpha-Toxin Antibodies in Combination with Linezolid are Prophylactically Protective in a Mouse Model of Staphylococcal Bacteremia This example illustrates the effect of alpha-toxin antibodies in a mouse model for staphylococcal bacteremia. In this example, the effect of alpha-toxin antibody treatment was studied in combination with linezolid treatment.

Female, fully immunocompetent Balb/c mice weighing 19-21 g were obtained from Harlan. The animals were 7-8 weeks old at the beginning of the experiment.

S. aureus strain USA300 (LAC) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An $O.D._{600}$ measurement was made using a spectrophotometer. The bacterial suspension was incubated in a 37° C. water bath until the culture arrived at the target McFarland forward light scatter range of 0.600-0.650 units, providing a bacterial concentration of approximately $10^9$ CFU/mL. This culture was used as the inoculum challenge stock and diluted to provide approximately $1.6 \times 10^7$ bacteria in 100 μL. After serial dilution, plating and back counting the challenge was confirmed to be $1.6 \times 10^7$ CFU in 100 μL. 10 animals per group were anesthetized through use of isoflourane (induced at 5% in an induction chamber). Each animal was administered the intravenous challenge with a total volume of 100 μL in the lateral tail vain. Instillation of the bacterial challenge constituted time 0h for the study.

The alpha-toxin antagonist antibody DF1.1 was formulated in PBS. The antibody and the vehicle treatment were each administered in a single intraperitoneal (ip) dose 24 hours prior to the bacterial challenge using a 0.5 mL dosing volume. Mice receiving antibody, received a dose of 30 mg/kg. The commercial antibacterial chemotherapeutic linezolid was provided by Pfizer and formulated at a dosing concentration of 6.25 mg/kg in an aqueous solution of 5% polyethylene glycol (PEG200), 0.5% methylcellulose. The linezolid treatment was administered by oral gavage (po) in a single dose using a 0.5 mL dosing volume.

The primary endpoint used to assess progression of the infection and activity of the mAb DF1.1 was mortality over a 14 day period following bacterial challenge. Graphic interpretation of the survival results (Kaplan-Meier) and statistical analysis (Log-rank/Mantel-Cox test, median survival time) were performed using GraphPad Prism v.5.0 (graphs not shown). Table 18 shows the cumulative survival rate for DF1.1-treated, linezolid-treated, DF1.1 and linezolid combination-treated, and vehicle-treated animals.

TABLE 18

| Treatment (dose, route, time) | Cumulative survival (%) | | | | | | |
|---|---|---|---|---|---|---|---|
| | Day 1 | Day 2 | Day 3 | Day 4 | Day 5 | Day 6 | Day 7 |
| Vehicle, i.p., −24 hr | 100 | 100 | 90 | 90 | 90 | 50 | 40 |
| Linezolid, 6.25 mg/kg, p.o., 0 hr | 100 | 100 | 100 | 100 | 100 | 70 | 70 |
| DF1.1, 30 mg/kg, i.p., −24 hr | 100 | 100 | 100 | 100 | 90 | 80 | 70 |
| DF1.1, 30 mg/kg, i.p., −24 hr + Linezolid, 6.25 mg/kg, p.o., 0 hr | 100 | 100 | 100 | 100 | 100 | 90 | 90 |

| Treatment (dose, route, time) | Day 8 | Day 9 | Day 10 | Day 11 | Day 12 | Day 13 | Day 14 |
|---|---|---|---|---|---|---|---|
| Vehicle, i.p., −24 hr | 30 | 30 | 30 | 30 | 30 | 30 | 30 |
| Linezolid, 6.25 mg/kg, p.o., 0 hr | 60 | 60 | 60 | 60 | 60 | 60 | 60 |
| DF1.1, 30 mg/kg, i.p., −24 hr | 60 | 50 | 50 | 50 | 50 | 50 | 50 |
| DF1.1, 30 mg/kg, i.p., −24 hr + Linezolid, 6.25 mg/kg, p.o., 0 hr | 80 | 80 | 80 | 80 | 80 | 80 | 80 |

Compared to the control, prophylactic treatment with alpha-toxin antibody in combination with linezolid treatment significantly reduced mortality in a mouse model of staphylococcal bacteremia. Combination treatment with alpha-toxin antagonist antibody and linezolid resulted in a survival rate of 80% at study end. At day 7, cumulative survival of the combination-treated animals was 90%. In contrast, control animals treated with vehicle had a survival rate of 30% at study end, and at day 7, the cumulative survival was 40%. Animals treated with alpha-toxin antagonist antibody had a survival rate of 50% at study end, and at day 7, the cumulative survival was 70%. Animals treated with linezolid had a survival rate of 60% at study end, and at day 7, the cumulative survival was 70%. These results demonstrate that combination treatment with alpha-toxin antagonist antibody and linezolid is protective and effective to prevent death and/or reduce disease severity in a mouse model of staphylococcal bacteremia. These results also demonstrate that, for at least the doses tested, the combination treatment is more effective in reducing mortality than either linezolid or alpha-toxin antagonist antibody alone.

Example 14

Alpha-Toxin Antibodies are Effective to Reduce Disease Severity in a Mouse Model of Staphylococcal Skin Abscess/Dermonecrosis This example illustrates the effect of alpha-toxin antibodies in a mouse model for staphylococcal skin abscess/dermonecrosis.

Female, fully immunocompetent Balb/c mice weighing 19-21 g were obtained from Harlan. The animals were 7-8 weeks old at the beginning of the experiment. On Day −1 each mouse was anesthetized using Isoflurane anesthetic. An area of approximately 2.0 cm×2.0 cm of skin on the dorsal area of each mouse was cleared of hair using the depilatory agent Nair®.

*Staphylococcus aureus* strain USA300 (LAC) was stored at −80° C. until initiated for use in the study. The culture was swabbed onto trypticase soy agar plates supplemented with 5% sheep blood cells (BBL, Becton Dickinson Laboratories, Franklin Lakes, N.J.), and grown at 37° C., in an ambient atmosphere. Cultures were removed from the incubator and scrapings of the organism were transferred to 200 mL of TSB. An O.D.600 measurement was made using a spectrophotometer. The bacterial suspension was incubated in a 37° C. water bath until the culture arrived at the target McFarland forward light scatter range of 0.600-0.650 units, providing a bacterial concentration of approximately $1\times10^9$ CFU/mL. This parent culture was diluted with TSB to provide a challenge concentration of approximately $1\times10^7$ CFU per mouse. A challenge volume of 0.05 mL was used for each intra-dermal (id) administration. Administration of the bacterial challenge constituted time 0 h for the study. The delivered bacterial challenge was confirmed by plate counts following challenge.

The final count of the challenge inoculum demonstrated a delivered burden of $1.3 \times 10^7$ organisms per mouse in a volume of 50 μl.

The alpha-toxin antagonist antibody DF1.1 was formulated in PBS. The antibody and the vehicle treatment were each administered in a single intraperitoneal (ip) dose 24 hours prior to the bacterial challenge using a 0.5 mL dosing volume. Mice receiving antibody received a dose of 50 mg/kg. The commercial antibacterial chemotherapeutic linezolid was provided by Pfizer and formulated at a dosing concentration of 50 mg/kg in an aqueous solution of 5% polyethylene glycol (PEG200), 0.5% methylcellulose. The linezolid treatment was administered by oral gavage (po) in a 0.5 mL dosing volume immediately following the bacterial challenge and again at 24 hours post challenge.

Mice were individually numbered and monitored daily for evaluation of abscess formation, signs of necrosis and mortality. Progression of abscess formation was tracked by measuring the length and width of the abscess daily. Table 19 shows the average area of the abscess (Area=$(\pi/2) \times$length$\times$width) in mm$^2$, and the standard error of the mean (SEM) for each group of animals. Abnormal clinical signs were recorded if observed.

TABLE 19

Average area of abscess (mm$^2$)

| Treatment | Day 0 | Day 1 | Day 2 | Day 3 | Day 4 |
|---|---|---|---|---|---|
| Vehicle | 0.0 mm$^2$ | 114.1 mm$^2$ | 120.0 mm$^2$ | 101.4 mm$^2$ | 78.7 mm$^2$ |
|  | SEM = 0.00 | SEM = 19.51 | SEM = 20.42 | SEM = 17.34 | SEM = 12.98 |
| 50 mg/kg | 0.0 mm$^2$ | 19.1 mm$^2$ | 23.6 mm$^2$ | 21.4 mm$^2$ | 21.6 mm$^2$ |
| DF1.1 | SEM = 0.00 | SEM = 2.31 | SEM = 2.16 | SEM = 2.50 | SEM = 4.33 |
| 50 mg/kg | 0.0 mm$^2$ | 0.0 mm$^2$ | 6.6 mm$^2$ | 4.9 mm$^2$ | 3.7 mm$^2$ |
| linezolid | SEM = 0.00 | SEM = 0.00 | SEM = 0.29 | SEM = .48 | SEM = 0.39 |
| TSB control | 0.0 mm$^2$ | 0.0 mm$^2$ | 0.0 mm$^2$ | 0.0 mm$^2$ | 0.0 mm$^2$ |
|  | SEM = 0.00 | SEM = 0.00 | SEM = 0.00 | SEM = 0.00 | SEM = 0.00 |
| No ID control | 0.0 mm$^2$ | 0.0 mm$^2$ | 0.0 mm$^2$ | 0.0 mm$^2$ | 0.0 mm$^2$ |
|  | SEM = 0.00 | SEM = 0.00 | SEM = 0.00 | SEM = 0.00 | SEM = 0.00 |

The primary endpoint used to assess progression of the infection and treatment activity was mean colony forming unit (CFU) burden per gram of excised skin. On study Day 4, mice were humanely euthanized by $CO_2$ asphyxiation and the skin was aseptically excised. Skin samples from each animal were weighed and placed in a homogenation vial. All tissue was homogenized through use of a Mini-BeadBeater™. Ten-fold serial dilutions of each sample were prepared in sterile TSB and cultured on blood agar plates. The plates were incubated at 37° C. at ambient atmosphere overnight and colonies were enumerated. Total CFU/g was determined along with geometric means and standard errors through use of Microsoft Excel. Statistical analysis was performed using a Student's t-Test for comparison of means, assuming unequal variance. Table 20 shows the bacterial burden for DF1.1-treated, linezolid-treated, and vehicle-treated animals. Graphic interpretation of the results was performed using GraphPad Prism v.5.0 (graphs not shown), by plotting mean CFU±SEM over time for bacterial burden and abscess/dermonecrosis area (mm$^2$, using the formula for the area of an ellipse) over time.

TABLE 20

| | Day 4 CFU/g tissue (log10) | | |
|---|---|---|---|
| | Vehicle | DF1.1 | Linezolid |
| mouse #1 | 8.1 | 5.2 | 4.5 |
| mouse #2 | 7.9 | 4.4 | 4.8 |
| mouse #3 | 7.6 | 4.1 | 5.1 |
| mouse #4 | 7.9 | 7.7 | 5.4 |
| mouse #5 | 8.2 | 7.1 | 4.9 |
| mouse #6 | 8.2 | 7.4 | 5.7 |
| mouse #7 | 7.6 | 7.8 | 5.2 |
| mouse #8 | 7.8 | 6.1 | 6.0 |
| Mean CFU/g | 7.9 | 6.2 | 5.2 |
| St. dev. | 0.220 | 1.500 | 0.481 |
| n | 8 | 8 | 8 |
| SEM | 0.078 | 0.530 | 0.170 |
| median | 7.9 | 6.6 | 5.1 |

Compared to the control, treatment with alpha-toxin antibody treatment significantly ameliorated disease symptoms in a mouse model of staphylococcal skin abscess/dermonecrosis. The area of skin abscess in mice treated with alpha-toxin antagonist antibody was significantly smaller than the area of skin abscess in control mice, i.e., mice treated with vehicle. As shown in Table 19 above, the mean area of skin abscess in mice treated with alpha-toxin antibody was about 19.1 mm$^2$ on day 1, about 23.6 mm$^2$ on day 2, about 21.4 mm$^2$ on day 3, and about 21.6 mm$^2$ on day 4. In contrast, the mean area of skin abscess in mice treated with vehicle was about 114.1 mm$^2$, 120.0 mm$^2$, 101.4 mm$^2$, and 78.7 mm$^2$ on days 1, 2, 3, and 4, respectively. The mean area of skin abscess in mice treated with linezolid was about 0.0 mm$^2$, 6.6 mm$^2$, 4.9 mm$^2$, and 3.7 mm$^2$ on days 1, 2, 3, and 4, respectively.

The bacterial burden in mice treated with alpha-toxin antagonist antibody was significantly lower than the bacterial burden in control mice. As shown in Table 20, the bacterial burden in the infected area of mice treated with alpha-toxin antagonist antibody was about 6.2 log 10 CFU/g on average. The bacterial burden in the infected area of mice treated with vehicle was about 7.9 log 10 CFU/g on average. The bacterial burden in the infected area of mice treated with linezolid was about 5.2 log 10 CFU/g on average.

These results demonstrate that treatment with antagonist alpha-toxin antibody is effective in reducing disease severity in a mouse model of staphylococcal skin abscess/dermonecrosis.

Example 15

Alpha-Toxin Variants

This example illustrates the sequence variation in alpha-toxin from various *S. aureus* strains.

To determine whether there are amino acid sequence differences in alpha-toxin from different *S. aureus* strains, genomic DNA samples were isolated from two hundred twenty-four different *S. aureus* strains. The alpha-toxin gene from each strain was PCR amplified from each sample of genomic DNA, purified, and sequenced. The DNA sequencing results were aligned for each *S. aureus* strain and a nucleotide consensus sequence was obtained. The nucleotide consensus sequence for each strain was translated and the amino acid sequences were aligned.

The sequencing results demonstrate that the sequences of the alpha-toxins from the different *S. aureus* strains are highly conserved. Only 20 amino acid positions out of the 293 amino acids in mature alpha-toxin have variability. The variations occurred at amino acid positions 9, 14, 19, 38, 52, 54, 79, 87, 129, 175, 194, 197, 208, 218, 239, 243, 246, 275, 278, 288 of the mature alpha-toxin (alpha-toxin without the leader sequence; the mature alpha-toxin sequence from USA300 is shown in SEQ ID NO: 74). From the genetic analysis of the two hundred twenty-four *S. aureus* strains, seventeen different alpha-toxin variants were identified. The sequence information for each alpha-toxin variant from is summarized in the table shown in FIG. 6. In the table, the *S. aureus* strain is provided in the first column, followed by the identity of the amino acid at each indicated amino acid position for the alpha-toxin variant from the indicated strain. All amino acid positions not shown in the table are identical to the corresponding amino acid position in the *S. aureus* USA300 mature alpha-toxin sequence, shown below:

```
                                        (SEQ ID NO: 74)
ADSDINIKTGTTDIGSNTTVKTGDLVTYDKENGMHKKVFYSFIDDKNHN

KKLLVIRTKGTIAGQYRVYSEEGANKSGLAWPSAFKVQLQLPDNEVAQI

SDYYPRNSIDTKEYMSTLTYGFNGNVTGDDTGKIGGLIGANVSIGHTLK

YVQPDFKTILESPTDKKVGWKVIFNNMVNQNWGPYDRDSWNPVYGNQLF

MKTRNGSMKAADNFLDPNKASSLLSSGFSPDFATVITMDRKASKQQTNI

DVIYERVRDDYQLHWTSTNWKGTNTKDKWIDRSSERYKIDWEKEEMTN.
```

Example 16

Epitope Mapping/Binding of Antibodies Using the Crystal Structure of the DF1.1:Alpha-toxin Complex The epitope residues for DF1.1 antibody on the *S. aureus* alpha-toxin protein were identified based on the crystal structure of DF1.1:alpha-toxin complex. The residues were identified by calculating the difference in accessible surface area between the DF1.1:alpha-toxin crystal structure and alpha-toxin structure alone. Alpha-toxin residues that show buried surface area upon complex formation with DF1.1 antibody were included as a part of the epitope. The solvent accessible surface of a protein was defined as the locus of the centre of a probe sphere (representing a solvent molecule of 1.4 Å radius) as it rolls over the Van der Waals surface of the protein. The solvent accessible surface area was calculated by generating surface points on an extended sphere about each atom (at a distance from the atom centre equal to the sum of the atom and probe radii), and eliminating those that lie within equivalent spheres associated with neighboring atoms as implemented in program AREAIMOL (Briggs, P. J. et al., 2000, CCP4 Newsletter No. 38, CCLRC, Daresbury).

The results of the crystal structure analysis are shown in FIG. 7. FIG. 7A shows the crystal structure of the alpha-toxin (light gray surface representation) bound to the DF1.1 antibody (black cartoon representation). The epitope for DF1.1 binding to alpha-toxin involves residues 30-32, 64-72, 78-79, 205, 207-208, 210-213, 253, 274, and 276 of mature alpha-toxin. Alpha-toxin residue R66 is at the center of the DF1.1 epitope. Alpha-toxin residues R66, E70, R200, D255 and D276 are important for interaction with the cell membrane (see, Walker et al., 1995, J. Biol. Chem. 270: 23065-23071). DF1.1 antibody binds directly to, or immediately adjacent to alpha-toxin residues R66, E70, D255 and D276, thereby making these positions unavailable to interact with the membrane. Results from membrane binding experiments demonstrate that alpha-toxin is not detected on the membrane when DF1.1 antibody is mixed with alpha-toxin prior to membrane binding. In contrast, in the absence of DF1.1 antibody, alpha-toxin binding to membrane is observed. The results of the membrane binding experiments are shown in FIG. 8A. The graph in FIG. 8A shows binding of alpha-toxin to the membrane on the left ("alpha-toxin"), and as shown on the right ("alpha-toxin+DF1.1"), this binding is completely abolished when the alpha-toxin is preincubated with DF1.1. These data demonstrate that DF1.1 can block alpha-toxin from binding to the cell membrane.

The DF1.1 epitope does not become occluded upon alpha-toxin heptamer formation (data not shown).

The interaction between DF1.1 and alpha-toxin is mediated predominantly by the DF1.1 heavy chain (FIG. 8B). Alpha-toxin binds to a cleft created by DF1.1 heavy chain CDR1 and CDR2 loops on one side, and CDR3 on the opposite side. The surface area of alpha-toxin buried by DF1.1 Fab is approximately 965 $Å^2$, while the surface area of DF1.1 buried by alpha-toxin is approximately 881 $Å^2$. The DF1.1 heavy chain contributes 90.1% (794 $Å^2$) of buried surface area. In contrast, the DF1.1 light chain contributes only 9.9% (87 $Å^2$).

Example 17

Alpha-Toxin Antibodies Block Lytic Activity of Alpha-Toxin In Vitro

This example illustrates the effect of alpha-toxin antibodies in an in vitro rabbit erythrocyte assay. In this example, the effect of the alpha-toxin antibodies in vitro using a rabbit erythrocyte lysis assay was measured.

A serial dilution of alpha-toxin (Calbiochem) was incubated with a suspension of 1% rabbit erythrocytes (Innovative Research) in a total volume of 0.2 ml at 37° C. for 1 h in a 96-well plate. The plate was subsequently spun at 2,400 rpm for 5 minutes to pellet intact and lysed erythrocytes. 0.1 ml of the supernatant was transferred to a new plate and the absorbance (hemoglobin released from lysed cells) was read at 405 nm. This provided a dose response of alpha-toxin lytic activity on rabbit erythrocytes.

Serial dilutions of alpha-toxin antibodies DF1, DF1.1, DF2 and DF19 were incubated with 0.5 nM *S. aureus* alpha-toxin (approximately EC50) at RT for 30 minutes in a 0.1 ml volume before being added to 0.1 ml of a suspension of 1% rabbit erythrocytes and incubated at 37° C. for 1 h in a 96-well plate. For a negative control and to measure maximum lysis under the experimental conditions, a sample with no antibody was incubated with 0.5 nM *S. aureus* alpha-toxin. To measure background lysis, a sample with no antibody and no alpha-toxin was used. The 96-well plate was subsequently spun at 2,400 rpm for 5 minutes and 0.1 ml of the supernatant from each sample transferred to a new plate and the absorbance read at 405 nm.

After background subtraction and normalization to maximum lysis with 0.5 nM alpha-toxin, nonlinear ergression curve fit and EC50 calculations were performed using GraphPad Prism v.5.0. EC50 for each anti-toxin antibody is shown below in Table 21, and the dose-dependent effect of each antibody on blocking the lytic activity of alpha-toxin on rabbit erythrocytes is shown in the graph in FIG. 9.

TABLE 21

| log(inhibitor) vs. response -- Variable slope | DF1.1 | DF1 | DF2 | DF19 |
|---|---|---|---|---|
| IC50 | 0.07483 nM | 0.4081 nM | 0.2388 nM | 0.3886 nM |

The alpha-toxin antibodies blocked alpha-toxin mediated lysis of rabbit erythrocytes in a dose-dependent manner (FIG. 9). As shown in Table 21, the EC50 of DF1.1, DF1, DF2 and DF19 was 0.07483 nM, 0.4081 nM, 0.2388 nM and 0.3886 nM, respectively. These results demonstrate that alpha-toxin antibodies are effective in blocking lytic activity of alpha-toxin in an in vitro rabbit erythrocyte lysis assay.

Example 18

Alpha-Toxin Antibodies Reduce Bacterial Burden in the Lungs in a Mouse Model of *S. aureus* Pneumonia This example illustrates the effect of alpha-toxin antibodies in an in mouse model of *S. aureus* pneumonia. In this example, the effect of the alpha-toxin antibodies on bacterial burden in vivo was measured.

Female, fully immunocompetent Balb/c mice at 6 weeks of age were obtained from Charles River. The animals were 7-8 weeks old at the beginning of the experiment. *S. aureus* strain USA300 FPR3757 (MRSA) was stored at −80° C. until initiated for use in the study. The culture was swabbed onto TSA plates (BBL, Becton Dickinson Laboratories, Franklin Lakes, N.J.), and grown at 37° C., in an ambient atmosphere. The TSA plate was used to grow an overnight liquid culture in TSB (Cellgro, Mediatech, Manassas, Va.), and a subsequent 1:100 subculture was made in TSB where bacteria were grown to an OD600=0.5. The culture was centrifuged and the pellet was resuspended in the appropriate volume of PBS to bring the bacterial concentration to the desired concentration. In this experiment mice were challenged with an inoculum of *S. aureus* at approximately $4 \times 10^8$ CFU per animal. After serial dilution, plating and back counting the actual challenge was determined to be $5.2 \times 10^8$ CFU per animal. Prior to bacterial challenge, animals were anesthetized through intraperitoneal dose of ketamine (100 mg/kg) and xylazine (10 mg/kg). There were 5 animals in each group. Each animal was administered an intranasal challenge of the bacterial culture with a total volume of 30 µL. Instillation of the bacterial challenge constituted time 0 h for the study.

mAb DF1.1 and isotype control Ab (hIgG) was formulated in PBS. The antibody treatment was administered at 30 mg/kg in a single intraperitoneal dose 24 hours prior to the bacterial challenge using a 0.18 ml dosing volume (average mouse weight 18 g).

One day after inoculation the mice were euthanized. The lungs were aseptically removed, transferred to Omni Bead Ruptor tubes containing 6 zirconium oxide 2.88 mm beads and 1 ml PBS+0.1% Triton X-100. The lungs were homogenized at 3.55 m/s three times for 30 seconds each with a 10 seconds pause between pulses. Ten-fold serial dilutions of each sample were prepared in sterile TSB and cultured on blood agar plates. The plates were incubated at 37° C. at ambient atmosphere for 1-2 days and colonies were enumerated. The total lung bacterial burdens were calculated for each mouse (Table 22). Statistical analysis (Man Whitney t-test, two-tailed P value) was performed using GraphPad Prism v.5.0.

TABLE 22

| | CFU/Lungs | |
|---|---|---|
| Treatment: | hIgG (control) | DF1 |
| mouse #1 | 2.50E+08 | 7.90E+07 |
| mouse #2 | 3.30E+08 | 3.70E+07 |
| mouse #3 | 1.10E+08 | 5.50E+07 |
| mouse #4 | 4.50E+08 | 3.50E+07 |
| mouse #5 | 8.10E+08 | 6.70E+07 |
| average | 3.90E+08 | 5.46E+07 |
| n | 5 | 5 |
| Stdev | 2.65E+08 | 1.90E+07 |
| Std err | 1.19E+08 | 8.49E+06 |

The bacterial burden in mice treated with alpha-toxin antagonist antibody was significantly lower than the bacterial burden in control mice. As shown in Table 22, the bacterial burden in the lungs of mice treated with alpha-toxin antagonist antibody was about 5.46E+07 CFU/lungs on average. The bacterial burden in the lungs of mice treated with control hIgG was about 3.90E+08 CFU/lungs on average.

These results demonstrate that treatment with antagonist alpha-toxin antibody is effective in reducing bacterial burden and disease severity in a mouse model of staphylococcal pneumonia.

Example 19

Characterization of Alpha-Toxin Antibodies

DF1.1 antibody variants were created at each position on the CDR3 region of both the heavy and light chain. Their affinity for alpha-toxin and their capacity to block the lytic activity of alpha-toxin on rabbit erythrocytes in vitro were determined establishing positions important for binding and blocking, and positions permissive of variation.

Binding affinity of each DF1.1 variant was measured using Biacore™ analysis. EC50 of each DF1.1 variant was measured in an in vitro rabbit erythrocyte lysis assay (method described above in Example 17, except that the concentration of alpha-toxin used was 2 nM). Results are shown in Tables 23 and 24. In Tables 23 and 24, the antibody name (left column) describes the mutated position in DF1.1. For example, "HCDR3-R2A" indicates that the antibody is a variant of DF1.1 having a substitution at position 2 of heavy chain CDR3 from arginine (R) to alanine (A); "LCDR3-Q1A" indicates that the antibody is a variant of DF1.1 having a substitution at position 1 of light chain CDR3 from glutamine (Q) to alanine (A); and "HCDR3-W10A/LCDR3-Y8A" indicates that the antibody is a variant of DF1.1 having a substitution at position 10 of heavy chain CDR3 from tryptophan (W) to alanine (A) and a substitution at position 8 of light chain CDR3 from tyrosine (Y) to alanine (A).

TABLE 23

| Antibody | Affinity KD (nM) | REL* EC50 (nM) |
|---|---|---|
| DF1.1 | <0.19** | 0.30 |
| HCDR3-R2A | 0.79 | 0.88 |
| HCDR3-M4R | 0.43 | 0.44 |
| HCDR3-E5A | 0.40 | 0.30 |
| HCDR-V6R | 0.22 | 0.26 |
| HCDR3-S7R | 0.30 | 0.22 |
| HCDR3-G8R | 0.40 | 0.25 |
| HCDR3-R9A | 0.40 | 0.33 |
| HCDR3-W10A | 3.40 | 12.02 |
| HCDR3-R11A | 0.80 | 0.55 |
| HCDR3-P12A | 1.30 | 2.14 |
| HCDR3-E14A | 0.34 | 0.14 |
| HCDR3-A15R | 37.00 | 246.80 |
| HCDR3-F16A | 0.67 | 0.57 |
| HCDR3-E17A | 0.33 | 0.25 |
| HCDR3-I18R | 0.23 | 0.25 |
| LCDR3-Q1A | <0.14** | 0.29 |
| LCDR3-Q2A | 0.13 | 0.29 |
| LCDR3-Y3A | 1.60 | 3.21 |
| LCDR3-G4R | <0.14** | 0.16 |
| LCDR3-S5R | 0.25 | 0.17 |
| LCDR3-S6R | 18.00 | 26.99 |
| LCDR3-P7A | <0.14** | 0.31 |
| LCDR3-Y8A | 1.20 | 1.47 |
| LCDR3-T9R | <0.14** | 0.35 |

**KD estimate: Off-rate too slow to be accurately determined in the Biacore assay used

TABLE 24

| Antibody | Affinity KD (nM) | REL* EC50 (nM) |
|---|---|---|
| HCDR3-A1R | no detectable binding | no detectable blocking |
| HCDR3-E3A | no detectable binding | no detectable blocking |
| HCDR3-T13R | no detectable binding | no detectable blocking |
| HCDR3-W10A/LCDR3-Y3A | 440 | 2093.00 |
| HCDR3-W10A/LCDR3-Y8A | 440 | 1679.00 |
| HCDR3-P12A/LCDR3-Y3A | 190 | 807.10 |
| HCDR3-P12A/LCDR3-S6R | 330 | 1067.00 |
| HCDR3-P12A/LCDR3-Y8A | 37 | 76.64 |
| HCDR3-A15R/LCDR3-Y3A | 280 | 871.70 |

Each of DF1.1 antibody variants listed in Table 23 retains nanomolar or sub-nanomolar affinity to alpha-toxin, indicating that the variant amino residue is at a position permissive of mutation. In contrast, each of DF1.1 antibody variants listed in Table 24 show substantially decreased affinity, or lack of binding, to alpha-toxin, indicating that the variant amino residue(s) is at a position important for binding. The corresponding EC50 values are consistent with antibody affinity being important for blocking alpha-toxin lytic activity.

Example 20

DF1.1 Alpha-Toxin Antibody Blocks Alpha-Toxin-Induced ADAM10 Activity

This example illustrates the effect of DF1.1 antibody on alpha-toxin-induced ADAM10 activity.

Alpha-toxin binds the zinc-dependent metalloprotease ADAM10 on the cell surface, resulting in E-cadherin cleavage and disruption of intercellular adherens junctions (Inoshima et al., 2011, Nat. Med. 17:1310-1314; Powers et al., 2012, J. Infect. Dis. 206:352-356; Wilke and Bubeck Wardenburg, 2010, Proc. Natl. Acad. Sci. U.S.A. 107:13473-13478).

To test whether DF1.1 can block alpha-toxin-induced ADAM10 activity, an ADAM10 metalloprotease assay was conducted. For the assay, A549 cells were plated at density of $1.5\times10^4$ cells/well in 96 well plates. The following day, 300 nM alpha-toxin, with or without prior incubation with serial dilutions of DF1.1 antibody or an IgG control antibody, was added to the cells and incubated for 60 min. An unstimulated sample (no alpha-toxin) sample was included to measure the amount of ADAM10 activity in the absence of alpha-toxin. Cells were washed once in 25 mM Tris, pH 8.0 buffer and incubated for 30 min at 37° C. with 10 μM fluorogenic peptide substrate (R&D Systems cat #ES003). Fluorescence intensity was read on a FlexStation instrument (Molecular Devices) and expressed as relative fluorescence units (RFU).

The results of the ADAM10 metalloprotease assay are shown in FIG. 10. Incubation with alpha-toxin (a-hemolysin) resulted in about a twofold increase in ADAM10 activity compared with the unstimulated sample (FIG. 10). Pre-incubation of alpha-toxin with IgG control antibody did not result in a reduction of the alpha-toxin-induced increase in ADAM10 activity (FIG. 10). In contrast, pre-incubation of alpha-toxin with DF1.1 antibody blocked the alpha-toxin-induced increase in ADAM10 activity in a dose-dependent manner (FIG. 10). These results demonstrate that the alpha-toxin antibody DF1.1 blocks alpha-toxin-induced increase in ADAM10 activity.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated antagonist antibody that specifically binds to S. aureus alpha-toxin and comprises: a heavy chain variable region (VH) comprising a VH complementarity determining region one (CDR1), VH CDR2, and VH CDR3 of the VH sequence of SEQ ID NO: 35; and a light chain variable region (VL) comprising a VL CDR1, VL CDR2, and VL CDR3 of the VL sequence of SEQ ID NO: 3.

2. The isolated antagonist antibody of claim 1, wherein the VH CDR1 comprises the amino acid sequence of SEQ ID NO: 5, 6 or 7, the VH CDR2 comprises the amino acid sequence of SEQ ID NO: 8 or 9, the VH CDR3 comprises the amino acid sequence of SEQ ID NO: 54, the VL CDR1 comprises the amino acid sequence of SEQ ID NO: 15, the VL CDR2 comprises the amino acid sequence of SEQ ID NO: 16, and the VL CDR3 comprises the amino acid sequence of SEQ ID NO: 17.

3. The isolated antagonist antibody of claim 2, wherein the VH comprises the amino acid sequence of SEQ ID NO: 35 or a variant thereof with one or several conservative amino acid substitutions in residues that are not within a CDR, and the VL comprises the amino acid sequence of SEQ ID NO: 3 or a variant thereof with one or several amino acid substitutions in amino acids that are not within a CDR.

4. The isolated antagonist antibody of claim 2, wherein the antibody comprises a heavy chain comprising the amino acid sequence of SEQ ID NO: 72 or 73 and a light chain comprising the amino acid sequence of SEQ ID NO: 23.

5. The isolated antagonist antibody of claim 1, wherein the antibody further comprises an immunologically inert constant region.

6. The isolated antagonist antibody of claim 5, wherein the antibody has an isotype that is selected from the group consisting of $IgG_2$, $IgG_{2\Delta a}$, $IgG_4$, $IgG_{4\Delta b}$, $IgG_{4\Delta c}$, $IgG_4$ S228P, $IgG_{4\Delta b}$ S228P and $IgG_{4\Delta c}$ S228P.

7. The isolated antagonist antibody of claim 5, wherein the constant region is aglycosylated Fc.

8. An isolated antagonist antibody that specifically binds to S. aureus alpha-toxin, wherein the antibody recognizes an epitope comprising amino acid residues 30-32, 64-72, 78-79, 205, 207-208, 210-213, 253, 274, and 276 of the alpha-toxin amino acid sequence shown in SEQ ID NO: 74.

9. The isolated antagonist antibody of claim 8, wherein the antibody blocks alpha-toxin from binding to a cell membrane.

10. The isolated antagonist antibody of claim 8, wherein the antibody binds to alpha-toxin with an equilibrium dissociation constant of about 20 pM or less.

11. The isolated antagonist antibody of claim 8, wherein the antibody comprises a heavy chain variable region (VH) complementarity determining region three (CDR3) sequence of SEQ ID NO: 54 or variants thereof wherein the amino acid at position 1 is D, E or G; the amino acid at position 2 is H, L, M, R, V or Y; the amino acid at position 3 is E, G, L or Y; the amino acid at position 4 is A, E, G, V or Y; the amino acid at position 5 is A, I, N, R, S, T or Y; the amino acid at position 6 is G, R, S or Y; the amino acid at position 7 is D, G, Q or R; the amino acid at position 8 is C, D, G, N, R, S, or W; the amino acid at position 9 is G, Q, R, S or Y; the amino acid at position 10 is G, L, P or R; the amino acid at position 11 is A, H, P, Q or T; the amino acid at position 12 is D, E, G, H, K, N or S; the amino acid at position 13 is A, L, P or V; the amino acid at position 14 is F or L; the amino acid at position 15 is D, E or S; and the amino acid at position 16 is F, I, L or V.

12. The isolated antagonist antibody of claim 11, wherein the antibody comprises: a VH CDR1 comprising the amino acid sequence of SEQ ID NO: 5, 6 or 7; and a VH CDR2 comprising the amino acid sequence of SEQ ID NO: 8 or 9.

13. The isolated antagonist antibody of claim 11, wherein the antibody comprises: a light chain variable region (VL) complementarity determining region three (CDR3) sequence of SEQ ID NO: 17 or variants thereof wherein the amino acid at position 1 is E, H, L, M or Q; the amino acid at position 2 is E, H, N, Q, R or S; the amino acid at position 3 is A, C, D, F, G, H, L, P, R, S, T, V or Y; the amino acid at position 4 is A, D, E, F, G, H, I, K, L, M, N, R, S, T, V or Y; the amino acid at position 5 is A, D, E, F, G, H, I, K, L, M, N, Q, R, S, T, V, W or Y; the amino acid at position 6 is A, D, F, G, I, K, L, M, N, P, Q, S, T, V, W or Y; the amino acid at position 7 is A, D, E, F, G, H, I, L, M, N, P, Q, R, S, T or V; the amino acid at position 8 is A, E, F, G, H, I, K, L, M, N, P, Q, R, S, T, V, W or Y; and the amino acid at position 9 is A, G, I, K, L, N, P, S, T or Y.

14. A pharmaceutical composition comprising the antagonist antibody of claim 1.

15. A pharmaceutical composition comprising the antagonist antibody of claim 11.

* * * * *